US006068982A

United States Patent [19]
Rolfe et al.

[11] Patent Number: 6,068,982
[45] Date of Patent: *May 30, 2000

[54] UBIQUITIN CONJUGATING ENZYMES

[75] Inventors: Mark Rolfe, Newton Upper Falls; Maria Isabel Chiu, Boston; Guillaume Cottarel, West Roxbury; Vivian Berlin, Dunstable; Veronique Damagnez, Cambridge; Giulio Draetta, Winchester, all of Mass.

[73] Assignee: Mitotix, Inc., Cambridge, Mass.

[ * ] Notice: This patent is subject to a terminal disclaimer.

[21] Appl. No.: 08/767,942

[22] Filed: Dec. 17, 1996

Related U.S. Application Data

[63] Continuation of application No. 08/486,663, Jun. 7, 1995, and a continuation-in-part of application No. 08/250,795, May 27, 1994, and application No. 08/305,520, Sep. 13, 1994, Pat. No. 5,774,343, which is a continuation-in-part of application No. 08/247,904, May 23, 1994, which is a continuation-in-part of application No. 08/176,937, Jan. 4, 1994, abandoned.

[51] Int. Cl.⁷ .................................................. G01N 33/53
[52] U.S. Cl. .............................. 435/7.21; 435/29; 435/4; 435/6; 435/7.1; 435/23; 435/69.1; 435/7.2; 435/193; 530/350
[58] Field of Search ........................ 435/4, 6, 7.1, 7.21, 435/23, 29, 69.1, 193, 7.2; 530/350

[56] References Cited

U.S. PATENT DOCUMENTS

| 5,384,255 | 1/1995 | Ciechanover et al. | 435/193 |
| 5,532,348 | 7/1996 | Huibregtse et al. | 536/23.5 |

FOREIGN PATENT DOCUMENTS

| WO 89/09829 | 10/1989 | WIPO . |
| WO 89/12678 | 12/1989 | WIPO . |
| WO 91/17245 | 11/1991 | WIPO . |
| WO 92/20804 | 11/1992 | WIPO . |
| WO 93/09235 | 5/1993 | WIPO . |

OTHER PUBLICATIONS

Adams et al. (1993) "Rapid cDNA sequencing (expressed sequence tags) from a directionally cloned human infant brain cDNA library", Nature Genetics 4:373–380.
Band et al. (1991) "Loss of p53 Protein in Human Papillomarvirus Type 16 E6–Immortalized Human Mammary Epithelial Cells", J. Virol., 65(12):6671–6676–87.
Berleth et al. (1992) "Inhibition of Ubiquitin–Protein Ligase (E3) by Mono–and Bifunctional Phenylarsenoxides" J.Biol. Chem. 267(23):16403–16411.
Bissonnette et al. (1992) "Apoptotic cell death induced by c–myc is inhibited by bcl–2", Nature 359:552–554.
Chen et al (1993) "Multiple Ubiquitin–Conjugating Enzymes Participate in the In Vivo Degradation of the Yeast MAT 2 Repressor", Cell 74:357–369. (1993).
Ciechanover et al. (1991) "Degradation of Nuclear Oncoproteins by the Ubiquitin System in Vitro", Proc. Natl. Acad. Sci. USA 88:139–143.

Cook et al. (1993) "Tertiary Structures of Class I Ubiquitin–Conjugating Enzymes Are Highly Conserved: Crystal Structure of Yeast Ubc4", Biochemistry 32(50):13809–13817.
Cook et al. (1192) "Structure of a Diubiquitin Conjugate and a Model for Interaction with Ubiquitin Conjugating Enzyme (E2)", J. Biol. Chem. 267(23);16467–16471.
Wilkinson (1990) Methods in Enzymology 185: 387–397.
Hershko et al. (1983) J. Biol. Chem. 258: 8206–8214.
Ciechanover et al. (1991) Proc. Natl. Acad. Sci. USA 88: 139–143.
Hochstrasser et al. (1991) Proc. Natl. Acad. Sci. USA 88: 4606–4610.
Huibregtse et al. (1993) Mol. Cell. Biol. 13: 4918–4927.
Glotzer et al. (1991) Nature 349: 132–138.
Crook et al. (1991) "Degradation of p53 Can Be Targeted by HPV E6 Sequences Distinct from Those Required for p53 Binding and Trans–Activation", Cell 67:547–556.
Dohmen et al. (1991) "The N–end rule is mediated by the UBC2(RAD6) ubiquitin–conjugating enzyme", Proc. Natl. Acad. Sci. 88:7351–7355.
Ellison et al. (1991) "Epitope–tagged Ubiquitin", J. Biol Chem 266(31):21150–21157.
Evan et al. (1992) "Induction fo Apoptosis in Fibroblasts by c–myc Protein", Cell 69:119–128.
Girod et al. (1993) "Homologs of the essential ubiquitin––conjugating enzymes UBC1, 4, and 5 yeast are encoded by a multigene family in Arabidopsis thaliana", The Plant Journal 3(4):545–552.
Glotzer et al. (1991) "Cyclin is degraded by the ubiquitin pathway", Nature 349:132–138.
Hartwell et al. (1992) "Defects in a Cell Cycle Checkpoint May Be Responsible for the Genomic Instability of Cancer Cells", Cell 71:543–546.
Hershko et al. (1993) "Components of Ubiquitin–Protein Ligase System", J. Biol. Chem. 258(13):8206–8214.
Hochstrasser et al. (1990) "In Vivo Degradation of a Transcriptional Regulator: The Yeast 2 Repressor", Cell 61:697–708.
Hochstrasser et al. (1991) "The Short–lived MAT 2 Transcriptional Regulator if Ubiquitinated in Vivo", Proc. Natl. Acad. Sci. USA 88:4606–4610.
Hoefer et al. (1991) "Purification and partial characterization of ubiquitin–activating enzyme from Saccharomyces cerevisiae", FEBS Letters 289(1):54–58.
Holloway et al. (1993) "Anaphase Is Initiated by Proteolysis Rather Than by the Inactivation of Maturation–Promoting Factor", Cell 73:1393–1402.

(List continued on next page.)

*Primary Examiner*—Robert A. Wax
*Assistant Examiner*—Enrique D. Longton
*Attorney, Agent, or Firm*—Foley, Hoag & Eliot LLP

[57] ABSTRACT

The present invention relates to drug screening assays which provide a systematic and practical approach for the identification of candidate agents able to inhibit ubiquitin-mediated degradation of a cell-cycle regulatory protein, such as p53, p27, myc, fos, MATα2, or cyclins. The invention further relates to novel ubiquitin-conjugating enzymes, and uses related thereto.

34 Claims, 6 Drawing Sheets

OTHER PUBLICATIONS

Huibregtse et al. (1993) "Cloning and Expression of the cDNA for E6–AP, a Protein That Mediates the Interaction of the Human Papillomavirus E6 Oncoprotein with p53", Mol Cell Biol 13(2):775–784.

Huibregtse et al. (1993) "Localization of the E6–AP Regions That Direct Human Papillomavirus E6 Binding, Association with p53, and Ubiquitination of Associated Proteins ", Mol Cell Biol 13(8):4918–4927.

Huibregtse et al. (1995) "A Family of Proteins Structurally and Functionally Related to the E6–AP Ubiquitin–protein Ligase", Proc. Natl. Acad. Sci. USA 92:2563–2567.

Huibregtse et al. (1991) "A cellular protein mediates association of p53 with the E6 oncoprotein of human papillomavirus types 16 or 18", EMBO J. 10(13):4129–4135.

Hupp et al. (1992) "Regulation of the Specific DNA Binding Function of p53", Cell 71:875–886.

Jacobs et al. (1993) "Rapid Assessment of Drug Susceptibilities of Mycobacterium tuberculosis by Means of Luciferase Reporter Phages", Science 260:819–822.

Jentsch (1992) "The Ubiquitin–conjugation System", Ann Rev Genet 26:179–207.

Klemperer et al. (1989) "A Novel, Arsenite–Sensitive E2 of the Ubiquitin Pathway: Purification and Properties", Biochemistry 28:6035–6041.

Koken et al. (1991) "Structural and Functional Conservation of Two Human Homologs of the Yeast DNA Repair Gene RAD6", Proc. Natl. Acad. Sci. 88:8865–8869.

Kumar et al. (1992) "Identification of a set of genes with developmentally down–regulated expression in the mouse brain", Biochem. Biophys. Res. Comm. 185:1155–1161.

Milner et al. (1990) "p53 Is Associated with $p34^{cdc2}$ In Transformed Cells", EMBO J. 9(9):2885–2889.

Münger et al. (1989) "The E6 and E7 Genes of the Human Papillomavirus Type 16 Together Are Necessary and Sufficient for Transformation of Primary Human Keratinocytes", J. Virol. 63(10):4417–4421.

Nefsky et al. (1996) "Pub1 acts as an E6–AP–like protein ubiquitin ligase in the degradation of cdc25", EMBO J. 15(16):1301–1312.

Nepveu et al. (1987) "Alternative modes of c–myc regulation in growth factor–stimulated and differentiating cells", Oncogene 1:243–250.

Rechsteiner et al. (1991) "Natural Substrates of the Ubiquitin Proteolytic Pathway", Cell 66:615–618.

Schärer et al. (1992) "Mammalian p53 can function as a transcription factor in yeast", Nucleic Acids Research 20(7):1539–1545.

Scheffner et al. (1992) "Interaction fo the Human Papillomavirus Type 16 E6 Oncoprotein with Wild–Type and Mutant Human p53 Proteins", J. Virol. 66(8):5100–5105.

Scheffner et al. (1990) "The E6 Oncoprotein Encoded by Human Papillomavirus Types 16 and 18 Promotes the Degradation of p53", Cell 63:1129–1136.

Scheffner et al. (1992) "Targeted degradation of the retinoblastoma protein by human papillomavirus E7–E6 fusion proteins", EMBO J. 11(7):2425–2431.

Scheffner et al. (1993) "The HPV–16 E6 and E6–AP Complex Functions as a Ubiquitin–Protein Ligase in the Ubiquitination of p53", Cell 75:495–505.

Seufert and Jentsch (1990) "Ubiquitin–conjugating enzymes UBC4 and UBC5 mediate selective degradation of short––lived and abnormal proteins", EMBO J. 9(2):543–550.

Treier et al. (1992) "Drosophila UbcD1 encodes a highly conserved ubiquitin–conjugating enzyme involved in selective protein degradation", EMBO J. 11(1):367–372.

Tyers et al. (1992) "The Cin3–Cdc28 kinase complex of S. cerevisiae is regulated by proteolysis and phosphorylation ", EMBO J. 11(5):1773–1784.

Watanabe et al. (1989) "Human Papillomavirus Type 16 Transformation of Primary Human Embryonic Fibroblasts Requires Expression of Open Reading Frames E6 and E7", J. Virol. 63(2):965–969.

Wilkinson (1990) "Detection and Inhibition of Ubiquitin––Dependent Proteolysis", Methods in Enzymology 185:387–397.

Zhen et al. (1993) "The ubc–2 Gene of Caenorhabditis elegans Encodes a Ubiquitin–Conjugating Enzyme Involved in Selective Protein Degradation", Mol Cell Biol 13(3):1371–1377.

```
Human       Met Ala Leu Lys Arg Ile His Lys Glu Leu Ala Asn Asp Leu Ala Arg Asp Pro Pro Ala Gln Cys Ser Ala Gly Pro Val Gly
S Pombe     Met Ala Leu Lys Arg Ile Asn Arg Glu Leu Ala Asp Lys Leu Gly Arg Asp Pro Pro Ser Cys Ser Cys Ser Ala Gly Pro Val Gly
C Albicans  Met Ser Leu Lys Arg Ile Asn Lys Glu Leu Ala Ser Asp Leu Ser Arg Asp Pro Pro Ser Cys Ser Cys Ser Ala Gly Pro Val Gly Asp Met Phe His Trp Gln Ala Thr Ile Met Gly Pro Asn Asp Ser Pro Tyr Gln Gly Gly Val Phe Phe Leu Thr Ile
            Asp Asp Phe His Trp Gln Ala Thr Ile Met Gly Pro Ala Asp Ser Pro Tyr Ala Gly Gly Val Phe Leu Leu Ser Ile
            Asp Leu Phe His Trp Gln Ala Ser Ile Met Gly Pro Pro Asp Ser Pro Tyr Ala Gly Gly Val Phe Leu Ser Ile His Phe Pro Thr Asp Tyr Pro Phe Lys Pro Pro Lys Val Ala Phe Thr Thr Arg Ile Tyr His Pro Asn Ile Asn Ser Asn
            His Phe Pro Thr Asp Tyr Pro Phe Lys Pro Pro Lys Val Asn Phe Thr Thr Arg Ile Tyr His Pro Asn Ile Asn Ser Asn
            His Phe Pro Thr Asp Tyr Pro Lys Pro Pro Leu Lys Ile Ala Leu Thr Thr Lys Ile Tyr His Pro Asn Ile Asn Ser Asn Gly Ser Ile Cys Leu Asp Ile Leu Arg Ser Gln Trp Ser Pro Ala Leu Thr Ile Ser Lys Val Leu Leu Ser Ile Cys Ser
            Gly Ser Ile Cys Leu Asp Ile Leu Arg Asp Gln Trp Ser Pro Ala Leu Thr Ile Ser Lys Val Leu Leu Ser Ile Cys Ser
            Gly Asn Ile Cys Leu Asp Ile Leu Lys Asp Gln Trp Ser Pro Ala Leu Thr Ile Ser Lys Val Leu Leu Ser Ile Cys Ser Leu Leu Cys Asp Pro Asn Pro Asp Asp Pro Leu Val Pro Glu Ile Ala Arg Ile Tyr Gln Thr Asp Arg Glu Lys Tyr Asn
            Leu Leu Thr Asp Pro Asn Pro Asp Asp Pro Leu Val Pro Glu Ile Ala His Val Tyr Lys Thr Asp Arg Ala Arg Tyr Glu
            Leu Leu Thr Asp Ala Asn Pro Asp Asp Pro Leu Val Pro Glu Ile Ala His Ile Tyr Lys Gln Asp Arg Lys Tyr Glu Arg Ile Ala ArgGlu Trp Thr Gln Lys Tyr Ala Met
            Leu Ser Ala ArgGlu Trp Thr Arg Lys Tyr Ala Ile
            Ala Thr Ala LysGlu Trp Thr Lys Lys Tyr Ala Val
```

FIG. 1 p53 binding site:  5'-TCGACGGACATGCCCGGGCATGTCCC-3'
                   3'-GCCTGTACGGGCCCGTACAGGGACGCT-5' myc binding site:  5'-TCGACCACGTGGC-3'
                   3'-GGTGCACCGAGCT-5'

Sp1 binding site:  5'-TCGACGGGGCGGGC-3'
                   3'-GCCCCGCCCGAGCT-5'

UBIQUITIN CONJUGATING ENZYMES

Related Applications

This application is a continuation application of Ser. No. 08/486,663 filed on Jun. 7, 1995, pending. The contents of the aforementioned application is hereby incorporated by reference.

This application is a continuation-in-part of U.S. Ser. No. 08/250,795, entitled "Immunosuppressant Target Proteins", filed on May 27, 1994 and is a continuation-in-part of U.S. Ser. No. 08/305,520, now U.S. Pat. No. 5,744,343 entitled "Ubiquitin Conjugating Enzymes", filed on Sep. 13, 1994 which is a continuation-in-part of U.S. Ser. No. 08/247,904, entitled "Human Ubiquitin Conjugating Enzyme", which is a continuation-in-part of U.S. Ser. No. 08/176,937 now abandoned, entitled "Assay and Reagents for Detecting Inhibitors of Ubiquitin-dependent Degradation of Cell Cycle Regulatory Proteins", filed on Jan. 4, 1994 the specification of which are incorporated by reference herein.

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

For instance, the p53 protein is a key regulator of mammalian cell growth and its gene is frequently mutated in a wide range of human tumors (Hollstein et al. (1991) *Science* 253:49–53). Furthermore, many DNA tumor viruses encode viral antigens that inactivate p53 (e.g., see Vogelstein et al. (1992) *Cell* 70:523–526). The high risk human papillomaviruses, such as HPV-16 and -18, are strongly implicated in the pathogenesis of cervical carcinoma (zur Hansen et al. (1991) *Science* 254:1167–1173). These viruses encode two transforming proteins, E6 and E7, that target the cellular growth regulators p53 and pRb respectively. The mode of inactivation of p53 by E6 is apparently mediated by a ubiquitin-dependent pathway. Viral E6 and a cellular E6-associated protein (E6AP) combine to stimulate the ubiquitination of p53, thus targeting p53 for degradation (Scheffner et al. (1990) *Cell* 63:1129–1136. In this reaction, E6 and E6 AP are thought to be providing a ubiquitin ligase, or E3-like activity (Scheffner et al. (1993) *Cell* 75:495–505). However, the ubiquitin-conjugating enzyme (E2) involved in p53 ubiquitination has not previously been characterized.

SUMMARY OF THE INVENTION

The present invention relates to the discovery of novel ubiquitin conjugating enzymes (hereinafter UBC's, e.g., UbCE's or rapUBC).

One aspect of the present invention relates to the discovery in eukaryotic cells, particularly human cells and certain yeast cells, of a novel ubiquitin conjugating enzyme (hereinafter "UbCE"). In human cells, the enzyme can function to mediate ubiquitination of cell check regulatory proteins, e.g. p53, and is therefore involved in regulating cell cycle progression, e.g. cell growth.

Another aspect of the present invention relates to the discovery in human cells of novel ubiquitin conjugating enzyme (rapUBC), which was discovered based on its ability to bind FKBP/rapamycin complexes. This enzyme can function to mediate ubiquitination of cell check regulatory proteins, e.g. p53, and is therefore involved in regulating eucaryotic cell cycle progression, e.g. cell growth.

Another aspect of the invention features a substantially pure preparation of a human UbCE polypeptide ("hUbCE"), or a fragment thereof, which can function as a ubiquitin conjugating enzyme. In a preferred embodiment: the polypeptide has an amino acid sequence at least 90% homologous to the amino acid sequence of SEQ ID No. 2; the polypeptide has an amino acid sequence at least 95% homologous to the amino acid sequence of SEQ ID No. 2; the polypeptide has an amino acid sequence at least 97% homologous to the amino acid sequence of SEQ ID No. 2; the polypeptide has an amino acid sequence identical to the amino acid sequence of SEQ ID No. 2. In a preferred embodiment: the fragment comprises at least 5 contiguous amino acid residues of SEQ ID No. 2; the fragment comprises at least 20 contiguous amino acid residues of SEQ ID No. 2; the fragment comprises at least 50 contiguous amino acid residues of SEQ ID No. 2. In a preferred embodiment, the fragment comprises at least a portion of amino acid residues Cys-107 through Met-147, e.g. 5 amino acid residues, e.g. 15 amino acid residues, e.g. 25 amino acid residues.

Another aspect of the invention features a substantially pure preparation of a Candida UbCE polypeptide ("caUbCE"), or a fragment thereof, which can function as a ubiquitin conjugating enzyme. In a preferred embodiment: the polypeptide has an amino acid sequence at least 90% homologous to the amino acid sequence of SEQ ID No. 4; the polypeptide has an amino acid sequence at least 95% homologous to the amino acid sequence of SEQ ID No. 4; the polypeptide has an amino acid sequence at least 97% homologous to the amino acid sequence of SEQ ID No. 4; the polypeptide has an amino acid sequence identical to the amino acid sequence of SEQ ID No. 4. In a preferred embodiment: the fragment comprises at least 5 contiguous amino acid residues of SEQ ID No. 4; the fragment comprises at least 20 contiguous amino acid residues of SEQ ID No. 4; the fragment comprises at least 50 contiguous amino acid residues of SEQ ID No. 4. In a preferred embodiment, the fragment comprises at least a portion of amino acid residues Cys-107 through Val-147, e.g. 5 amino acid residues, e.g. 15 amino acid residues, e.g. 25 amino acid residues.

Another aspect of the invention features a substantially pure preparation of a Schizosaccharomyces UbCE polypeptide ("spUbCE"), or a fragment thereof, which can function as a ubiquitin conjugating enzyme. In a preferred embodiment: the polypeptide has an amino acid sequence at least 90% homologous to the amino acid sequence of SEQ ID No. 6; the polypeptide has an amino acid sequence at least 95% homologous to the amino acid sequence of SEQ ID No. 6; the polypeptide has an amino acid sequence at least 97% homologous to the amino acid sequence of SEQ ID No. 6; the polypeptide has an amino acid sequence identical to the amino acid sequence of SEQ ID No. 6. In a preferred embodiment: the fragment comprises at least 5 contiguous amino acid residues of SEQ ID No. 6; the fragment comprises at least 20 contiguous amino acid residues of SEQ ID No. 6; the fragment comprises at least 50 contiguous amino acid residues of SEQ ID No. 6. In a preferred embodiment, the fragment comprises at least a portion of amino acid residues Cys-107 through Ile-147, e.g. 5 amino acid residues, e.g. 15 amino acid residues, e.g. 25 amino acid residues.

Another aspect of the invention features a substantially pure preparation of a human UBC polypeptide ("rapUBC"), or a fragment thereof, which can function as a ubiquitin conjugating enzyme. In a preferred embodiment: the polypeptide has an amino acid sequence at least 90% homologous to the amino acid sequence of SEQ ID No. 13; the polypeptide has an amino acid sequence at least 95% homologous to the amino acid sequence of SEQ ID No. 13; the polypeptide has an amino acid sequence at least 97% homologous to the amino acid sequence of SEQ ID No. 13; the polypeptide has an amino acid sequence identical to the amino acid sequence of SEQ ID No. 13. In a preferred embodiment: the fragment comprises at least 5 contiguous amino acid residues of SEQ ID No. 13; the fragment comprises at least 20 contiguous amino acid residues of SEQ ID No. 13; the fragment comprises at least 50 contiguous amino acid residues of SEQ ID No. 13.

Another aspect of the present invention features an hUbCE polypeptide which functions in one of either role of an agonist of cell-cycle regulation or an antagonist of cell-cycle regulation. In a preferred embodiment the hUbCE polypeptide has: an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. The biological activity can further include the ability to bind and conjugate ubiquitin, as well as bind and transfer ubiquitin to E6AP.

Another aspect of the present invention features a rapUBC polypeptide which functions in one of either role of an agonist of cell-cycle regulation or an antagonist of cell-cycle regulation. In a preferred embodiment the rapUBC polypeptide has: an ability to bind a FKBP/rapamycin complex, an ability to mediate ubiquitination of cellular proteins, e.g. cell-cycle regulatory proteins, e.g. p53 or p27; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in cancerous cells. Given that rapamycin causes a block in the cell-cycle during G1 phase, it is probable that the spectrum of biological activity of the subject rapUBC enzyme includes control of half-lives of certain cell cycle regulatory proteins, particularly relatively short lived proteins (e.g. proteins which have half-lives on the order of 30 minutes to 2 hours). For example, the subject rapUBC may have the ability to mediate ubiquitination of, for example, p53, p27, myc and/or cyclins, and therefore affects the cellular half-life of a cell-cycle regulatory protein in proliferating cells. The binding of the rapUBC to the FKBP/rapamycin complex may result in sequestering of the enzyme away from its substrate proteins. Thus, rapamycin may interfere with the ubiquitin-mediated degradation of p53 in a manner which causes cellular p53 levels to rise which in turn inhibits progression of the G1 phase.

Yet another aspect of the present invention concerns an immunogen comprising an UBC polypeptide, or a fragment thereof, in an immunogenic preparation, the immunogen being capable of eliciting an immune response specific for the UBC polypeptide; e.g. a humoral response, eg. an antibody response; e.g. a cellular response.

A still further aspect of the present invention features an antibody preparation specifically reactive with an epitope of the UBC immunogen, e.g., reactive with rapUBC, e.g. reactive with hUbCE, e.g. reactive with caUbC, e.g. reactive with spUbCE.

Another aspect of the present invention features recombinant hUbCE polypeptide, or a fragment thereof, having an amino acid sequence preferably: at least 90% homologous to SEQ ID No. 2; at least 95% homologous to SEQ ID No: 2; at least 97% homologous to SEQ ID No. 2. In a preferred embodiment, the recombinant hUbCE protein functions in one of either role of an agonist of cell cycle regulation or an antagonist of cell cycle regulation. In a more preferred embodiment: the hUbCE polypeptide mediates ubiquitination of cellular proteins, e.g. cell-cycle regulatory proteins, e.g. p53; the hUbCE polypeptide mediates ubiquitin-dependent degradation of cellular proteins, e.g. cell-cycle regulatory proteins, e.g. p53; the hUbCE polypeptide affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

Another aspect of the present invention features recombinant caUbCE polypeptide, or a fragment thereof, having an amino acid sequence preferably: at least 90% homologous to SEQ ID No. 4; at least 95% homologous to SEQ ID No. 4; at least 97% homologous to SEQ ID No. 4. In a preferred embodiment, the recombinant caUbCE protein functions in one of either role of an agonist of cell cycle regulation or an antagonist of cell cycle regulation. In a more preferred embodiment the caUbCE polypeptide mediates ubiquitination of cellular proteins of candida cells.

Another aspect of the present invention features recombinant spUbCE polypeptide, or a fragment thereof, having an amino acid sequence preferably: at least 90% homologous to SEQ ID No. 6; at least 95% homologous to SEQ ID No. 6; at least 97% homologous to SEQ ID No. 6. In a preferred embodiment, the recombinant spUbCE protein functions in one of either role of an agonist of cell cycle regulation or an antagonist of cell cycle regulation. In a more preferred embodiment the spUbCE polypeptide mediates ubiquitination of cellular proteins of Schizosaccharomyces cells.

Another a frag of the present invention features recombinant rapUBC polypeptide, or a fragment thereof, having an amino acid sequence preferably: at least 90% homologous to SEQ ID No. 13; at least 95% homologous to SEQ ID No: 13; at least 97% homologous to SEQ ID No. 13. In a preferred embodiment, the recombinant rapUBC protein functions in one of either role of an agonist of cell cycle regulation or an antagonist of cell cycle regulation. In a more preferred embodiment: the rapUBC polypeptide mediates ubiquitination of cellular proteins, e.g. cell-cycle regulatory proteins, e.g. p53; the rapUBC polypeptide mediates ubiquitin-dependent degradation of cellular proteins, e.g. cell-cycle regulatory proteins, e.g. p53; the rapUBC polypeptide affects the cellular half-life of a cell-cycle regulatory protein, e.g. a cell-cycle checkpoint protein, e.g. p53, e.g. in normal cells, e.g. in cancerous cells.

In yet other preferred embodiments, the recombinant UBC protein is a fusion protein further comprising a second polypeptide portion having an amino acid sequence from a protein unrelated the protein of SEQ ID No. 2, 4, 6 or 13. Such fusion proteins can be functional in a two-hybrid assay.

Another aspect of the present invention provides a substantially pure nucleic acid having a nucleotide sequence which encodes an hUbCE polypeptide, or a fragment thereof, having an amino acid sequence at least 90% homologous to SEQ ID NO. 2. In a more preferred embodiment, the nucleic acid encodes a protein having an amino acid sequence at least 95% homologous to SEQ ID No. 2; and more preferably at least 97% homologous to SEQ ID No. 2. The nucleic preferably encodes: a hUbCE polypeptide which mediates ubiquitination of cellular proteins, e.g. cell-cycle regulatory proteins, e.g. p53; a hUbCE polypeptide which mediates ubiquitin-dependent degradation of cellular proteins, e.g. cell-cycle regulatory proteins, e.g. p53; a hUbCE polypeptide which affects the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells.

Another aspect of the present invention provides a substantially pure nucleic acid having a nucleotide sequence which encodes a caUbCE polypeptide, or a fragment thereof, having an amino acid sequence at least 90% homologous to SEQ ID NO. 4. In a more preferred embodiment, the nucleic acid encodes a protein having an amino acid sequence at least 95% homologous to SEQ ID No. 4; and more preferably at least 97% homologous to SEQ ID No. 4.

Another aspect of the present invention provides a substantially pure nucleic acid having a nucleotide sequence which encodes an spUbCE polypeptide, or a fragment thereof, having an amino acid sequence at least 90% homologous to SEQ ID NO. 4. In a more preferred embodiment, the nucleic acid encodes a protein having an amino acid sequence at least 95% homologous to SEQ ID No. 4; and more preferably at least 97% homologous to SEQ ID No. 4.

Another aspect of the present invention provides a substantially pure nucleic acid having a nucleotide sequence which encodes a rapUBC polypeptide, or a fragment thereof, having an amino acid sequence at least 90% homologous to SEQ ID NO. 13. In a more preferred embodiment, the nucleic acid encodes a protein having an amino acid sequence at least 95% homologous to SEQ ID No. 13; and more preferably at least 97% homologous to SEQ ID No. 13. The nucleic acid preferably encodes: a rapUBC polypeptide which mediates ubiquitination of cellular proteins, e.g. cell-cycle regulatory proteins, e.g. p53; a rapUBC polypeptide which mediates ubiquitin-dependent degradation of cellular proteins, e.g. cell-cycle regulatory proteins, e.g. p53; a rapUBC polypeptide which affects the cellular half-life of a cell-cycle regulatory protein, e.g. a cell-cycle checkpoint protein, e.g. p53, e.g. in normal cells, e.g. in cancerous cells.

In yet a further preferred embodiment, the nucleic acid which encodes a UBC polypeptide of the present invention, or a fragment thereof, hybridizes under stringent conditions to a nucleic acid probe corresponding to at least 12 consecutive nucleotides of one of SEQ ID Nos. 1, 3, 5 or 12; more preferably to at least 20 consecutive nucleotides of said sequences; more preferably to at least 40 consecutive nucleotides. In yet a further preferred embodiment, the UbCE encoding nucleic acid hybridizes to a nucleic acid probe corresponding to a subsequence encoding at least 4 consecutive amino acids between residues 107 and 147 of SEQ ID No. 2, 4 or 6, more preferably at least 10 consecutive amino acid residues, and even more preferably at least 20 amino acid residues. In yet a preferred embodiment the nucleic acid encodes an hUbCE polypeptide which includes Cys-107 through Cys-111.

Furthermore, in certain preferred embodiments, UBC encoding nucleic acid will comprise a transcriptional regulatory sequence, e.g. at least one of a transcriptional promoter or transcriptional enhancer sequence, operably linked to the UBC gene sequence so as to render the UBC gene sequence suitable for use as an expression vector. In one embodiment, the UBC gene is provided as a sense construct. In another embodiment, the UBC gene is provided as an anti-sense construct.

The present invention also features transgenic non-human animals, e.g. mice, which either express a heterologous hUbCE or rapUBC gene, e.g. derived from humans, or which mis-express their own homolog of the subject human gene, e.g. expression of the mouse hUbCE or rapUBC homolog is disrupted. Such a transgenic animal can serve as an animal model for studying cellular disorders comprising mutated or mis-expressed hUbCE opr rapUBC alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No. 1 or SEQ ID No:12, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a hUbCE or a rapUBC nucleic acid in a sample of cells isolated from a patient; e.g. measuring the hUbCE or rapUBC mRNA level in a cell; e.g. determining whether the genomic hUbCE or rapUBC gene has been mutated or deleted.

The present invention also provides a method for treating an animal having unwanted cell growth characterized by a loss of wild-type p53 function, comprising administering a therapeutically effective amount of an agent able to inhibit a ubiquitin conjugating activity of the subject hUbCE or rapUBC protein.

The present invention also provides a method for treating an animal having an unwanted mycotic infection, comprising administering a therapeutically effective amount of an agent able to inhibit a ubiquitin conjugating activity of a fungal ubiquitin-conjugating enzyme, such as the subject caUbCE protein or spUBC protein, without substantially inhibiting the hUbCE protein.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by SEQ ID No. 2 or SEQ ID No:13, or a homolog thereof; or (ii) the mis-expression of the hUbCE or rapUBC gene. In preferred embodiments: detecting the genetic lesion comprises ascertaining the existence of at least one of a deletion of one or more nucleotides from the gene, an addition of one or more nucleotides to the gene, an substitution of one or more nucleotides of the gene, a gross chromosomal rearrangement of the gene, a gross alteration in the level of a messenger RNA transcript of the gene, the presence of a non-wild type splicing pattern of a messenger RNA transcript of the gene, or a non-wild type level of the protein. For example, detecting the genetic lesion can comprise (i) providing a probe/primer comprising an oligonucleotide containing a region of nucleotide sequence which hybridizes to a sense or antisense sequence of SEQ ID No. 1 or SEQ ID No:12, or naturally occurring mutants thereof or 5' or 3' flanking sequences naturally associated with the gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the hUbCE or rapUBC gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of the protein is detected in an immunoassay.

The present invention also provides a systematic and practical approach for the identification of candidate agents able to inhibit ubiquitin-mediated degradation of a cell-cycle regulatory protein, such as p53, p27, myc, fos, MATα2, or cyclins. One aspect of the present invention relates to a method for identifying an inhibitor of ubiquitin-mediated proteolysis of a cell-cycle regulatory protein by (i) providing a ubiquitin-conjugating system that includes the regulatory protein and ubiquitin under conditions which promote the ubiquitination of the target protein, and (ii) measuring the level of ubiquitination of the subject protein brought about by the system in the presence and absence of a candidate agent. A decrease in the level of ubiquitin conjugation is indicative of an inhibitory activity for the candidate agent. The level of ubiquitination of the regulatory protein can be measured by determining the actual concentration of protein:ubiquitin conjugates formed; or inferred by detecting some other quality of the subject protein affected by ubiquitination, including the proteolytic degradation of the protein. In certain embodiments, the present assay comprises an in vivo ubiquitin-conjugating system, such as a cell able to conduct the regulatory protein through at least a portion of a ubiquitin-mediated proteolytic pathway. In other embodiments, the present assay comprises an in vitro ubiquitin-conjugating system comprising a reconstituted protein mixture in which at least the ability to transfer ubiquitin to the regulatory protein is constituted. Moreover, the present assay may further comprise auxiliary proteins which influence the level of ubiquitin-mediated degradation, including viral oncogenic proteins, such as the E6 protein of high-risk HPVs, which influence the level of the regulatory protein in an infected cell by enhancing or otherwise altering the proteolysis of the protein.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE FIGURES

FIG. 1 is a sequence alignment of hUbCE ("human") (SEQ ID NO 12), spUbCE ("S pombe") and caUbCE ("C albicans")(SEQ ID NO:4).

DETAILED DESCRIPTION OF THE INVENTION

Figure 2:
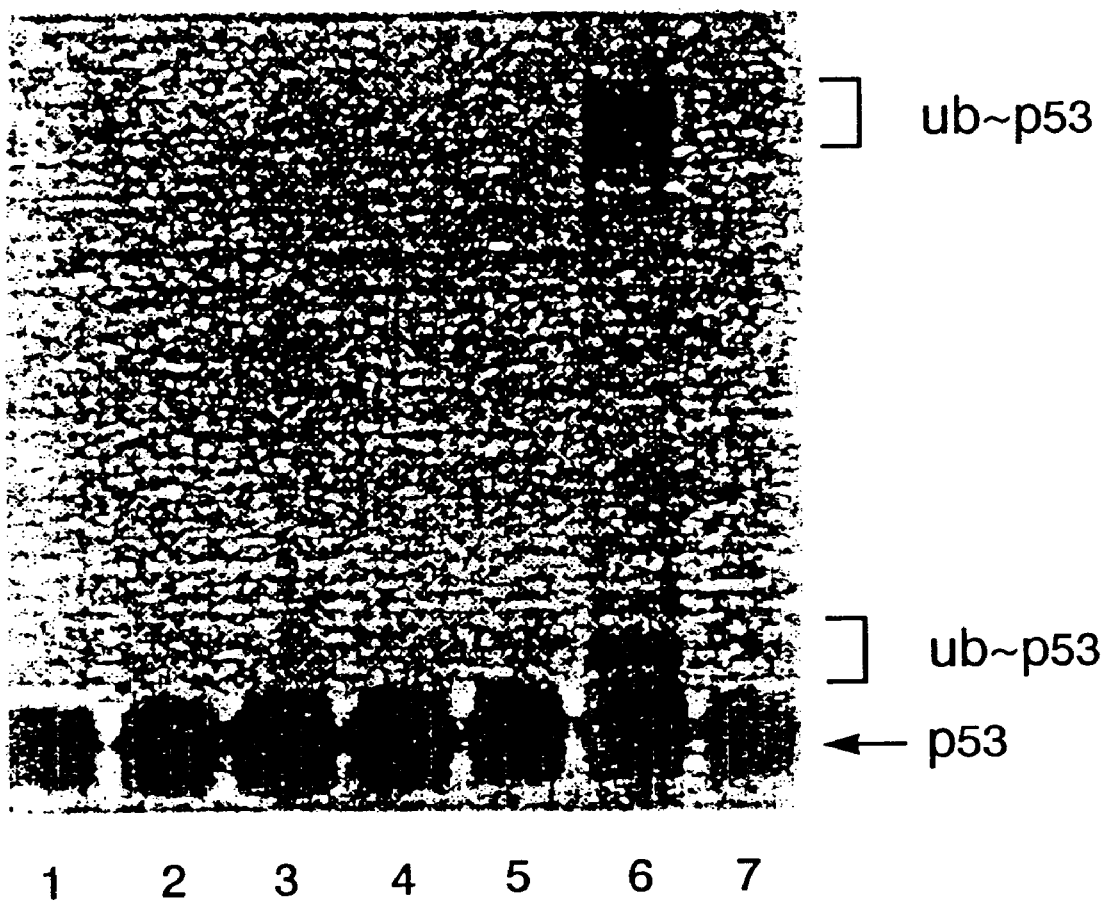
FIG. 2 illustrates the hUbCE dependent ubiquitination of p53 in an in vitro ubiquitination reaction. A complete ubiquitination reaction shown in lane 6 contained E1, hUbCE, E6, E6AP, p53 and ubiquitin. The following changes were made in lanes 1–5: lane 1 no E6, lane 2 no E6AP, lane 3 UBC2 replaces hUbCE, lane 4 no E1, lane 5 no ubiquitin. In lane 7 mutant hUbCE (Cys85→Ser) replaces wild-type hUbCE.

The ubiquitin system is essential for a wide spectrum of cellular phenomena, and is a component of many biological regulatory mechanisms, including aspects of growth control, metabolic regulation, tissue differentiation and development, and cell-cycle progression.

The present invention relates to the discovery of ubiquitin-conjugating enzymes (UBC's) involved in regulating cell cycle progression.

One aspect of the present invention relates to the discovery of a family of related ubiquitin-conjugating enzymes ("UbCE"?). In particular, members of this family have been cloned from various eukaryotic sources, and include, for example, a human ubiquitin-conjugating enzyme ("hUbCE"), a C. albican ubiquitin-conjugating enzyme ("caUbCE"), and an S. pombe ubiquitin-conjugating enzyme ("spUbCE"). The nucleotide sequences for the human UbCE, the C. albican UbCE, and the S. pombe UbCE coding sequences are provided in SEQ ID Nos. 1, 3 and 5, respectively. The corresponding amino acid sequences are represented in SEQ ID Nos. 2, 4 and 6.

Another aspect of the invention relates to the discovery of a novel human ubiquitin-conjugating enzyme ("rapUBC"). rapUBC has been cloned based on its ability to bind FKBP/rapamycin complexes. The human rapUBC coding sequence is provided in SEQ ID No:12. The corresponding amino acid sequence is represented in SEQ ID No:13.

The biological activity of the UBCE (e.g., UbCE and rapUBC) proteins of the present invention is evidently to be important in a number of basic cellular functions, such as regulation of gene expression, regulation of the cell-cycle, modification of cell surface receptors, biogenesis of ribosomes, and DNA repair. An apparent function of these enzymes in ubiquitin-mediated systems is to control the cellular half-lives of vasrious proteins. For instance, as demonstrated in the Examples, hUbCE is implicated in the ubiquitin-mediated inactivation of cell-cycle regulatory proteins, particularly p53. As is generally known, p53 is a checkpoint protein that plays an important role in sensing DNA damage or regulating cellular response to stress. Moreover, lesions in the p53 gene have been shown to be associated with a wide variety of proliferative diseases. Consequently, the present invention identifies a potential molecular target, e.g., hUbCE, for regulating the cellular half-life of p53 and thereby modulating, for instance, cell proliferation, apoptosis and cellular sensitivity to chemotherapeutics and DNA damaging agents.

Accordingly, the present invention makes available diagnostic and therapeutic assays, reagents and kits for detecting and treating proliferative disorders arising from, for example, tumorogenic transformation of cells, or other hyperplastic or neoplastic transformation processes. For example, the present invention makes available reagents, such as antibodies and nucleic acid probes, for detecting altered complex formation, and/or altered levels of hUbCE or rapUBC expression, and/or hUbCE or rapUBC-gene deletion or mutation, in order to identify transformed cells. Moreover, the present invention provides a method of treating wide variety of pathological cell proliferative conditions, such as by gene therapy utilizing recombinant gene constructs encoding the subject UBC proteins, by providing peptidomimetics which either inhibit or potentiate the interaction between the UBC and other cellular proteins, or by providing inhibitors of the catalytic activity of the enzyme. Such methods can also be used in cell and tissue culture, such as to regulate the transformation of cells in vitro.

In similar fashion, the present invention also makes available diagnostic and therapeutic assays for detecting and treating yeast/fungal infections, where such infections occur in an animal, e.g. humans, or on a non-living object, such as food or medical instruments. For example, given the apparent role of the subject UbCEs, namely caUbCE and spUbCE, in regulation of proteins involved in growth, mating and proliferation of yeast, inhibitors of the subject ubiquitin conjugating enzyme can be used to treat mycotic infections, as disinfectants, or as food preservatives.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a UBC polypeptide of the present invention, including both exon and (optionally) intron sequences. In preferred embodiments, the nucleic acid is DNA or RNA. Exemplary recombinant genes include nucleic acids which encode all or a catalytically active portion of the hUbCE protein represented in SEQ ID No. 2, the caUbCE protein represented in SEQ ID No. 4, the spUbCE protein represented in SEQ ID No. 6, or the rapUBC protein represented in SEQ ID No: 13. The term "intron" refers to a DNA sequence present in a given UBC-gene which is not translated into protein and is generally found between exons.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous nucleic acid, and, for example, the transformed cell expresses a recombinant form of one of the subject UBC proteins.

"Cells" or "cell cultures" or "recombinant host cells" or "host cells" are often used interchangeably as will be clear from the context. These terms include the immediate subject cell which expresses a ubiquitin-conjugating enzyme of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant UBC-protein.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/or expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant UBC-gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of an epithelial lineage, e.g. cervical squamous cells. In an illustrative embodiment of epithelial-specific promoters, gene constructs can be used as a part of gene therapy to deliver, for example, genes encoding a domaint negative hUbCE or rapUBC mutant, in order to inhibit degradation of p53 required for the pathogenesis of certain papillomavirus-mediated disorders, e.g. papillomas, or to direct expression of an antisense construct of the subject ubiquitin-conjugating enzyme in only epithelial tissue. The term also covers so-called "leaky" promoters, which regulate expression of a selected DNA primarily in one tissue, but cause expression in other tissues as well.

As used herein, a "transgenic animal" is any animal, preferably a non-human mammal in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject UBC protein, e.g. either agonistic or antagonistic forms, or in which the endogenous UBC gene has been disrupted. However, transgenic animals in which the recombinant UBC gene is silent are also contemplated, as for example, the FLP or CRE recombinase dependent constructs described below. The "non-human animals" of the invention include vertebrates such as rodents, non-human primates, sheep, dog, cow, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant UBC gene is present and/or expressed in some tissues but not others.

As used herein, the term "transgene" means a nucleic acid sequence (encoding, e.g., a UBC polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "evolutionarily related to", with respect to nucleic acid sequences encoding the subject ubiquitin-conjugating enzymes, refers to nucleic acid sequences which have arisen naturally in an organism, including naturally occurring mutants. The term also refers to nucleic acid sequences which, while derived from a naturally occurring enzymes, have been altered by mutagenesis, as for example, combinatorial mutagenesis described below, yet still encode polypeptides which have at least one activity of a UBC protein.

As described below, one aspect of this invention pertains to an isolated nucleic acid comprising a nucleotide sequence encoding one of the subject UBC proteins, fragments thereof encoding polypeptides having at least one biological activity of the UBC protein, and/or equivalents of such nucleic acids. The term "nucleic acid" as used herein is intended to include such fragments and equivalents. The term "equivalent" is understood to include nucleotide sequences encoding functionally equivalent UBC proteins or functionally equivalent peptides having an activity of a ubiquitin-conjugating enzyme such as described herein. Equivalent nucleotide sequences will include sequences that differ by one or more nucleotide substitutions, additions or deletions, such as allelic variants; and will also include sequences that differ from the nucleotide sequence encoding the hUbCE gene shown in SEQ ID No: 1, the caUbCE gene shown in SEQ ID No: 3, the spUbCE gene shown in SEQ ID No: 5, or the rapUBC gene shown in SEQ ID No: 12, due to the degeneracy of the genetic code. Equivalents will also include nucleotide sequences which hybridize under stringent conditions (i.e., equivalent to about 20–27° C. below the melting temperature ($T_m$) of the DNA duplex formed in about 1M salt) to the nucleotide sequence represented in at least one of SEQ ID Nos: 1, 3, 5 or 12. In one embodiment, equivalents will further include nucleic acid sequences derived from and evolutionarily related to the nucleotide sequences shown in any of SEQ ID Nos: 1, 3, 5 or 12.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding on of the subject UBC-proteins preferably includes no more than 10 kilobases (kb) of nucleic acid sequence which naturally immediately flanks the UBC gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Polypeptides referred to herein as possessing the activity of a ubiquitin-conjugating enzyme (UBC), e.g. are UBC agonists, are understood to have an amino acid sequence identical to or homologous with the amino acid sequences shown in any on of SEQ ID Nos: 2, 4, 6 or 13, and which are capable of forming a thiol ester adduct with the C-terminal carboxyl group of ubiquitin and transferring the ubiquitin to an i-amino group in an acceptor protein by formation of an isopeptide bond. The biological activity of the subject UBC proteins can include participation in degradative pathways for selective proteolysis of constitutively or conditionally short-lived proteins as well as abnormal proteins. Antagonistic forms of the subject UBC proteins are defined as proteins that are homologous, but not identical, to the UBC proteins represented in SEQ ID Nos: 2, 4, 6 or 13, or that are fragments of the wild-type proteins, which inhibit the transfer of ubiquitin by the naturally occurring form of the ubiquitin-conjugating enzyme. For instance, as described below, mutations in the active site of the enzyme, e.g. Cys-85, can produce dominant negative forms of the subject UbCEs which antagonize the action of the wild-type form of the protein.

Polypeptides referred to in particular as having an activity of an hUbCE protein are defined as peptides that have an amino acid sequence corresponding to all or a portion of the amino acid sequence of the human ubiquitin conjugating enzyme shown in SEQ ID No: 2 and which have at least one biological activity of an hUbCE protein: such as an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in normal proliferating cells, e.g. in virally-infected cells, e.g. in papillomavirus infected cells, e.g. in HPV-infected cells, e.g. in HPV-16, HPV-18, HPV-31, or HPV-33 infected cells, e.g. in cells expressing a papillomavirus E6 protein, e.g. in transformed cells, e.g. in cancerous cells. Other biological activities of the subject hUbCE proteins are described herein or will be reasonably apparent to those skilled in the art.

Polypeptides referred to in particular as having an activity of a rapUBC protein are defined as peptides that have an amino acid sequence corresponding to all or a portion of the amino acid sequence of the human ubiquitin conjugating enzyme shown in SEQ ID No:13 and which have at least one biological activity of a rapUBC protein: such as an ability to bind a FKBP/rapamycin complex, an ability to mediate ubiquitination of cellular proteins, e.g. cell-cycle regulatory proteins, e.g. p53; an ability to mediate ubiquitin-dependent degradation of cellular proteins, e.g. cell-cycle regulatory proteins, e.g. p53; an ability to affect the cellular half-life of a cell-cycle regulatory protein, e.g. a cell-cycle checkpoint protein, e.g. p53, e.g. in normal cells, e.g. in cancerous cells. Given that rapamycin causes a block in the cell-cycle during G1 phase, the spectrum of biological activity of the subject rapUBC enzyme is believed to include control of half-lives of certain cell cycle regulatory proteins, particularly relatively short lived proteins (e.g. proteins which have half-lives on the order of 30 minutes to 2 hours). For example, the subject rapUBC may mediate ubiquitination of, for example, p53, myc, p27 and/or cyclins, and therefore affects the cellular half-life of a cell-cycle regulatory protein in proliferating cells. The binding of the rapUBC to the FKBP/rapamycin complex may result in sequestering of the enzyme away from its substrate proteins. Thus, rapamycin may interfere with the ubiquitin-mediated degradation of p53 in a manner which causes cellular p53 levels to rise which in turn inhibits progression of the G1 phase.

Moreover, it will be generally appreciated that, under certain circumstances, it will be advantageous to provide homologs of naturally-occurring forms of the subject UBC proteins which are either agonists or antagonists of only a subset of that protein's biological activities. Thus, specific biological effects can be elicited by treatment with a homolog of limited function, and with fewer side effects relative to treatment with agonists or antagonists which are directed to all of the biological activities of that protein. For example, hUbCE and rapUBC homologs can be generated which bind to and inhibit activation of other proteins in the ubiquitin pathway of p53 without substantially interfering with the ubiquitination of other cellular proteins.

In one embodiment, the nucleic acid of the invention encodes a polypeptide which is either an agonist or antagonist the human UBC protein and comprises an amino acid sequence represented by SEQ ID No: 2. Preferred nucleic acids encode a peptide having an hUbCE protein activity, or which is an antagonist thereof, and being at least 90% homologous, more preferably 95% homologous and most preferably 97% homologous with an amino acid sequence shown in SEQ ID No: 2. Nucleic acids which encode agonist or antagonist forms of an hUbCE protein and having at least about 98–99% homology with a sequence shown in SEQ ID No: 2 are also within the scope of the invention. Preferably, the nucleic acid is a cDNA molecule comprising at least a portion of the nucleotide sequence encoding an hUbCE protein shown in SEQ ID No. 1. A preferred portion of the cDNA molecule shown in SEQ ID No. 1 includes the coding region of the molecule.

In another embodiment, the nucleic acid of the invention encodes a polypeptide which is either an agonist or antagonist a Candida UbCE protein, e.g. a *C. albican* UbCE, and comprises an amino acid sequence represented by SEQ ID No: 4. Preferred nucleic acids encode a peptide having an caUbCE protein activity, or which is an antagonist thereof, and being at least 90% homologous, more preferably 95% homologous and most preferably 97% homologous with an amino acid sequence shown in SEQ ID No: 4. Nucleic acids which encode agonist or antagonist forms of an caUbCE protein and having at least about 98–99% homology with a sequence shown in SEQ ID No: 4 are also within the scope of the invention. Preferably, the nucleic acid is a cDNA molecule comprising at least a portion of the nucleotide sequence encoding an caUbCE protein shown in SEQ ID No. 3. A preferred portion of the cDNA molecule shown in SEQ ID No. 3 includes the coding region of the molecule. The present invention contemplates closely related homologs (orthologs) from other species of Candida, e.g. *Candida stellatoidea, Candida tropicalis, Candida parapsilosis, Candida krusei, Candida pseudotropicalis, Candida quillermondii,* or *Candida rugosa.*

In yet another embodiment, the nucleic acid of the invention encodes a polypeptide which is either an agonist or antagonist of a Schizosaccharomyces UbCE protein, e.g. an *S. pombe* UbCE, and comprises an amino acid sequence represented by SEQ ID No: 6. Preferred nucleic acids encode a peptide having an spUbCE protein activity, or which is an antagonist thereof, and being at least 90% homologous, more preferably 95% homologous and most preferably 97% homologous with an amino acid sequence shown in SEQ ID No: 6. Nucleic acids which encode agonist or antagonist forms of an spUbCE protein and having at least about 98–99% homology with a sequence shown in SEQ ID No: 6 are also within the scope of the invention. Preferably, the nucleic acid is a cDNA molecule comprising at least a portion of the nucleotide sequence encoding an spUbCE protein shown in SEQ ID No. 5. A preferred portion of the cDNA molecule shown in SEQ ID No. 5 includes the coding region of the molecule.

In yet another embodiment, the nucleic acid of the invention encodes a polypeptide which is either an agonist or antagonist of the human UBC protein and comprises an amino acid sequence represented by SEQ ID No:13. Preferred nucleic acids encode a peptide having a rapUBC protein activity, or which is an antagonist thereof, and being at least 90% homologous, more preferably 95% homologous and most preferably 97% homologous with an amino acid sequence shown in SEQ ID No:13. Nucleic acids which encode agonist or antagonist forms of a rapUBC protein and having at least about 98–99% homology with a sequence shown in SEQ ID No: 13 are also within the scope of the invention. Preferably, the nucleic acid is a cDNA molecule comprising at least a portion of the nucleotide sequence encoding a rapUBC protein shown in SEQ ID No:12. A preferred portion of the cDNA molecule shown in SEQ ID No: 12 includes the coding region of the molecule.

Another aspect of the invention provides a nucleic acid which hybridizes under high or low stringency conditions to a nucleic acid which encodes a peptide having all or a portion of an amino acid sequence shown in one of SEQ ID Nos: 2, 4, 6 or 13. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which differ in sequence from the nucleotide sequences represented in SEQ ID Nos: 1, 3, 5 or 12 due to degeneracy in the genetic code are also within the scope of the invention. Such nucleic acids can encode functionally equivalent peptides (i.e., a peptide having a biological activity of a UBC protein) but differ in sequence from the sequence shown in SEQ ID No: 1, 3, 5 or 12 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the subject UBC protein. However, it is expected that DNA sequence polymorphisms that do lead to changes in the amino acid sequences of the present hUbCE or rapUBC proteins will exist from one human subject to the next. One skilled in the art will appreciate that these variations in one or more nucleotides (up to about 3–4% of the nucleotides) of the nucleic acids encoding peptides having an activity of, for example, an hUbCE or a rapUBC protein may exist among individuals due to natural allelic variation. Any and all such nucleotide variations and resulting amino acid polymorphisms are within the scope of this invention.

Fragments of the nucleic acid encoding an active portion of one of the subject ubiquitin-conjugating enzymes are also within the scope of the invention. As used herein, a fragment of the nucleic acid encoding an active portion of a UBC protein refers to a nucleotide sequence having fewer nucleotides than the nucleotide sequence encoding the entire amino acid sequence of the protein but which encodes a peptide which possess agonistic or antagonistic activity relative to a naturally occurring form of the enzyme.

Nucleic acid fragments within the scope of the invention also include those capable of hybridizing under high or low stringency conditions with nucleic acids from other species for use in screening protocols to detect UBC homologs.

Nucleic acids within the scope of the invention may also contain linker sequences, modified restriction endonuclease sites and other sequences useful for molecular cloning, expression or purification of recombinant peptides having at least one biological activity of the subject UbCE ubiquitin-conjugating enzymes. In a preferred embodiment, the nucleic acid fragment comprises at least a portion of the nucleic acid sequence represented by nucleotide residues 319 through 441 of SEQ ID No. 1, corresponding to amino acid residues Cys-107 through Met-147. In preferred embodiments, the nucleic acid encodes an hUbCE polypeptide which includes Cys-107 through Cys-111, and more preferably includes Cys-107 through Asp-117. As apparent from our computer modeling, certain of the residues from Cys-107 to Asp-111 are important members of the ubiquitin-binding site of hUbCE. Correspondingly, nucleic acid encoding caUbCE or spUbCE preferably include Cys-107 through Val-147 and Cys-107 through Ile-107, respectively.

As indicated by the examples set out below, a nucleic acid encoding a peptide having an activity of the subject ubiquitin-conjugating enzymes may be obtained from mRNA or genomic DNA present in any of a number of eukaryotic cells in accordance with protocols described herein, as well as those generally known in the art. A cDNA encoding a homolog of one of the human UBC proteins, for example, can be obtained by isolating total mRNA from a cell, e.g. a mammalian cell. Double stranded cDNAs can then be prepared from the total mRNA, and subsequently inserted into a suitable plasmid or bacteriophage vector using any one of a number of known techniques. A gene encoding a UBC protein can also be cloned using established polymerase chain reaction techniques in accordance with the nucleotide sequence information provided herein.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a UBC protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes one of the subject UBC-proteins, e.g. the human hUbCE gene represented in SEQ ID No. 1 or the rapUBC gene represented in SEQ ID No:12. Alternatively, the antisense construct can be an oligonucleotide probe which is generated ex vivo and which, when introduced into the cell causes inhibition of expression by hybridizing with the mRNA and/or genomic sequences encoding one of the UBC proteins. Such oligonucleotide probes are preferably modified oligonucleotide which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

This invention also provides expression vectors containing a nucleic acid encoding the subject UBC proteins, operably linked to at least one transcriptional regulatory sequence. Operably linked is intended to mean that the nucleic acid is linked to a transcriptional regulatory sequence in a manner which allows expression of the enzyme encoded by the nucleic acid, and that expression is, for example, either constitutively or inducibly controlled by the transcriptional regulatory sequence. Regulatory sequences are art-recognized. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990).

For instance, any of a wide variety of expression control sequences-sequences that control the expression of a DNA sequence when operatively linked to it may be used in these vectors to express DNA sequences encoding the UBC proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast alpha-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In one embodiment, the expression vector includes DNA encoding one of the subject hUbCE proteins, e.g. a recombinant hUbCE protein. Similar expression vectors for producing recombinant forms of the rapUBC protein are also contemplated. Such expression vectors can be used to transfect cells to thereby produce proteins or peptides, including fusion proteins or peptides, encoded by nucleic acids as described herein.

Moreover, hUbCE or rapUBC-expression vectors can be used as a part of a gene therapy protocol to reconstitute hUbCE or rapUBC function in a mammalian cell in which hUbCE or rapUBC is misexpressed, or alternatively, to provide an antagonist of the naturally-occurring hUbCE or rapUBC, or an antisense construct—such as to inhibit hUbCE or rapUBC-mediated degradation of a cell-cycle regulatory protein. For instance, expression constructs of the subject hUbCE or rapUBC-proteins may be administered in any biologically effective carrier, e.g. any formulation or composition capable of effectively transfecting cells in vivo with a recombinant hUbCE or rapUBC-gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject hUbCE or rapUBC-proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include $\psi$Crip, $\psi$Cre, $\psi$2 and $\psi$Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has also been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079–9083; Julan et al. (1992) *J Gen Virol* 73:3251–3255; and Goud et al. (1983) *Virology* 163:251–254); or coupling cell surface ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue or cell-specific transcriptional regulatory sequences which control expression of the hUbCE or rapUBC-gene of the retroviral vector.

Another viral gene delivery system useful in the present invention utilitizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) *BioTechniques* 6:616; Rosenfeld et al. (1991) *Science* 252:431–434; and Rosenfeld et al. (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biolo*, E. J. Murray, Ed. (Humana, Clifton, N.J., 1991) vol. 7. pp. 109–127). Expression of the inserted hUbCE or rapUBC-gene can be under control of, for example, the E1A promoter, the major late promoter (MLP) and associated leader sequences, the E3 promoter, or exogenously added promoter sequences.

Yet another viral vector system useful for delivery of the subject hUbCE or rapUBC-genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant hUbCE or rapUBC-genes in cells of the central nervous system and occular tissue (Pepose et al. (1994) *Invest Ophthalmol Vis Sci* 35:2662–2666).

In addition to viral transfer methods, such as those illustrated above, non-viral methods can also be employed to cause expression of an hUbCE or rapUBC-protein, or an hUbCE or a rapUBC antisense molecule, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject hUbCE or rapUBC-gene by the targeted cell. Exemplary gene delivery systems of this type include liposomal derived systems, poly-lysine conjugates, and artificial viral envelopes.

In a representative embodiment, a gene encoding one of the subject ubiquitin-conjugating enzymes can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of papilloma-virus infected epithelial cells can be carried out using liposomes tagged with monoclonal antibodies against, for example, squamous cells.

In similar fashion, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject UBC-gene construct can be used to transfect HPV-infected squamous cells in vivo using a soluble polynucleotide carrier comprising an HPV viral caot protein conjugated to a polycation, e.g. poly-lysine (see U.S. Pat. No. 5,166,320). It will also be appreciated that effective delivery of the subject nucleic acid constructs via—mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al. (1992) *PNAS* 89:7934; and Christiano et al. (1993) PNAS 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91:3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. The generation of such implants is generally known in the art. See, for example, *Concise Encyclopedia of Medical & Dental Materials*, ed. by David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; Sefton U.S. Pat. No. 4,353,888; and Aebischer et al. (1991) *Biomaterials* 12:50–55).

This invention also pertains to a host cell transfected or transformed to express a recombinant forms of the subject UBC proteins. The host cell may be any prokaryotic or eukaryotic cell. For example, an hUbCE or rapUBC polypeptide of the present invention may be expressed in bacterial cells such as E. coli, insect cells (baculovirus), yeast, or mammalian cells. Other suitable host cells are known to those skilled in the art.

The term "recombinant protein" refers to a protein of the present invention which is produced by recombinant DNA techniques, wherein generally DNA encoding the UBC protein is inserted into a suitable expression vector which is in turn used to transform a host cell to produce the heterologous protein. Moreover, the phrase "derived from", with respect to a recombinant gene encoding the recombinant UBC, is meant to include within the meaning of "recombinant protein" those proteins having an amino acid sequence of a native UBC, e.g. hUbCE, caUbCE, spUbCE, or rapUBC, or an amino acid sequence similar thereto which is generated by mutations including substitutions and deletions of a naturally occurring form of the protein. Recombinant proteins preferred by the present invention, in addition to native proteins, are at least 90% homologous, more preferably 95% homologous and most preferably 97% homologous with an amino acid sequence shown in one of SEQ ID Nos: 2, 4, 6 or 13. Polypeptides having an activity of a UBC protein, or which are antagonistic thereto, and which are at least about 90%, more preferably at least about 95%, and most preferably at least about 98–99% homologous with a sequence shown in SEQ ID No: 2, 4, 6 or 13 are also within the scope of the invention.

The present invention further pertains to recombinant UBC homologs which are encoded by genes derived from other non-human mammals, e.g. mouse, rat, rabbit, or pig, and which have amino acid sequences evolutionarily related to an hUbCE or rapUBC protein. As described above, such recombinant UBC or rapUBC proteins preferably are capable of functioning in one of either role of an agonist or antagonist of at least one biological activity of an hUbCE or rapUBC. The term "evolutionarily related to", as set out above, refers to ubiquitin-conjugating enzymes having amino acid sequences which have arisen naturally, or which are mutationally derived, for example, by combinatorial mutagenesis or scanning mutagenesis, but which proteins are homologous to either the hUbCE protein represented in SEQ ID No: 2 or rapUBC protein represented in SEQ ID No:13.

The present invention further pertains to methods of producing the subject proteins. For example, a host cell transfected with an expression vector encoding one of the subject UBC proteins can be cultured under appropriate conditions to allow expression of the polypeptide to occur. The peptide may be secreted (e.g. through use of recombinantly added signal sequence) and isolated from a mixture of cells and medium containing the secreted protein. Alternatively, the peptide may be retained cytoplasmically, as it presumably is its naturally occurring form, and the cells harvested, lysed and the protein isolated. A cell culture includes host cells, media and other byproducts. Suitable media for cell culture are well known in the art. The subject UBC polypeptides can be isolated from cell culture medium, host cells, or both using techniques known in the art for purifying proteins including ion-exchange chromatography, gel filtration chromatography, ultrafiltration, electrophoresis, and immunoaffinity purification with antibodies raised against the protein. In a preferred embodiment, the UBC protein is a fusion protein containing a domain which facilitates its purification, such as the hUbCE-GST fusion protein described below.

Thus, a nucleotide sequence derived from the cloning of a UBC protein of the present invention, encoding all or a selected portion of the protein, can be used to produce a recombinant form of the enzyme via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. p53, C-myc, cyclins, cdks and the like. Similar procedures, or modifications thereof, can be employed to prepare recombinant proteins, or portions thereof, by microbial means or tissue-culture technology in accord with the subject invention.

The recombinant protein can be produced by ligating the cloned gene, or a portion thereof, into a vector suitable for expression in either prokaryotic cells, eukaryotic cells, or both. Expression vehicles for production of recombinant UBCs include plasmids and other vectors. For instance, suitable vectors for the expression of the subject proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant UBc by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the 13-gal containing pBlueBac III).

When expression of a portion of the ubiquitin-conjugating enzyme is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing UBC-derived polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a UBC protein. In an exemplary embodiment, the VP6 capsid protein of rotavirus can be used as an immunologic carrier protein for portions of the hUbCE or rapUBC polypeptide, either in the monomeric form or in the form of a viral particle. The nucleic acid sequences corresponding to the portion of the hUbCE or rapUBC protein to which antibodies are to be raised can be incorporated into a fusion gene construct which includes coding sequences for a late vaccinia virus structural protein to produce a set of recombinant viruses expressing fusion proteins comprising a portion of the protein hUbCE or rapUBC as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an UBC protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized, wherein a desired portion of a UBC protein is obtained directly from organochemical synthesis of the peptide onto an oligomeric branching lysine core (see, for example, Posnett et al. (1988) *J Biol Chem* 263:1719 and Nardelli et al. (1992) *J. Immunol.* 148:914). Antigenic determinants of the UBC proteins can also be expressed and presented by bacterial cells.

In addition to utilizing fusion proteins to enhance immunogenicity, it is widely appreciated that fusion proteins can also facilitate the expression of proteins, such as the UBC proteins of the present invention. For example, as described below, the hUbCE protein can be generated as a glutathione-S-transferase (GST) fusion protein. Such GST fusion proteins can enable purification of the hUbCE protein, such as by the use of glutathione-derivatized matrices (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351). In another embodiment, a fusion gene coding for a purification leader sequence, such as a poly-(His)/enterokinase cleavage site sequence at the N-terminus of the desired portion of the hUbCE protein, can allow purification of the expressed hUbCE -fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972). Similar constructs can be generated for expression of rapUBC, caUbCE, or spUbCE.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Various modifications of the hUbCE protein to produce these and other functionally equivalent peptides are described in detail herein. In similar fashion, homologs of the subject rapUBC, caUBC and spUBC polypeptides are contemplated, including both agonistic and antagonistic forms. The term peptide, as used herein, refers to peptides, proteins, and polypeptides.

The present invention also makes available isolated UBC proteins, which proteins are isolated from or otherwise substantially free of other extracellular proteins, especially other proteins of the ubiquitin conjugating system (i.e. other E1 or E2 enzymes, as well as E3 proteins or ubiquitin) normally associated with the ubiquitin-conjugating enzyme in the cellular milleau. The term "substantially free of other extracellular proteins" (also referred to herein as "contaminating proteins") is defined as encompassing preparations of the subject UBC protein comprising less than 20% (by dry weight) contaminating protein, and preferably comprising less than 5% contaminating protein. Functional forms of the subject UBC proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other enzymes of the ubiquitin system such as other E1 or E2 proteins, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins or chromatography reagents such as denaturing agents and polymers, e.g. acrylamide or agarose) substances or solutions.

Isolated peptides having an activity of an UBC protein, or which can function as antagonists of a naturally occurring form of the UBC protein described herein can also be obtained by screening peptides recombinantly produced from the corresponding fragment of the nucleic acids encoding such peptides. In addition, fragments can be chemically synthesized using techniques known in the art such as conventional Merrifield solid phase f-Moc or t-Boc chemistry. For example, the hUbCE protein may be arbitrarily divided into fragments of desired length with no overlap of the fragments, or preferably divided into overlapping fragments of a desired length. The fragments can be produced (recombinantly or by chemical synthesis) and tested to identify those peptides having an hUbCE protein activity or alternatively to identify antagonists. Similar manipulation of the rapUBC, caUbCE and soUbCE proteins can be carried out.

Furthermore, it is also possible to modify the structure of a UBC polypeptide for such purposes as enhancing therapeutic or prophylactic efficacy, or stability (e.g., shelf life ex vivo and resistance to proteolytic degradation in vivo). Such modified peptides are considered functional equivalents of peptides having an activity of, or which antagonize, a UBC protein as defined herein. A modified polypeptide can be produced in which the amino acid sequence has been altered, such as by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed, Ed. by L. Stryer, WH Freeman and Co.: 1981). Whether a change in the amino acid sequence of a peptide results in a functional UBC homolog can be readily determined by assessing the ability of the variant peptide to, for instance, mediate ubiquitination in a fashion similar to the wild-type UBC. Peptides in which more than one replacement has taken place can readily be tested in the same manner.

The invention also includes a method of generating sets of combinatorial mutants of the subject UBC proteins, as well as truncation and fragmentation mutants, and is especially useful for identifying potential variant sequences which are functional in ubiquitinating cellular proteins. One purpose for screening such combinatorial libraries is, for example, to isolate novel UBC homologs which act as antagonist of the wild-type ("authentic") UBC activity, e.g. an hUbCE homolog which inhibits p53 ubiquitination, or alternatively, possess novel activities all together. Such proteins, when expressed from recombinant DNA constructs, can be used in gene therapy protocols.

Likewise, mutagenesis can give rise to UBC homologs which have intracellular half-lives dramatically different than the corresponding wild-type protein. For example, the altered protein can be rendered either more stable or less stable to proteolytic degradation or other cellular process which result in destruction of, or otherwise inactivation of, a naturally occurring form of the subject hUbCE or rapUBC proteins. Such hUbCE or rapUBC homologs (either agonist or antagonist homologs), and the genes which encode them, can be utilized to alter the envelope of recombinant hUbCE or rapUBC expression by modulating the half-life of the protein. For instance, a short half-life for the recombinant hUbCE or rapUBC can give rise to more transient biological effects associated with that homolog and, when part of an inducible expression system, can allow tighter control of recombinant hUbCE or rapUBC levels within the cell. As above, such proteins, and particularly their recombinant nucleic acid constructs, can be used in gene therapy protocols.

In one aspect of this method, the amino acid sequences for a population of UBC homologs or other related proteins are aligned, preferably to promote the highest homology possible. Such a population of variants can include, for example, hUbCE or rapUBC homologs from one or more species, or UBC homologs from the same species but which differ due to mutation. Amino acids which appear at each position of the aligned sequences are selected to create a degenerate set of combinatorial sequences. For instance, alignment of the hUbCE, caUbCE and spUbCE sequences provided in the appended sequence listing (see also FIG. 1) can be used to generate a degenerate library of UbCE proteins represented by the general formula:

Met Xaa(1) Leu Lys Arg Ile Xaa(2) Xaa(3) Glu Leu Xaa(4) Asp Leu Xaa(5)

Xaa(6) Asp Pro Pro Xaa(7) Xaa(8) Cys Ser Ala Gly Pro Val Gly Asp Asp Xaa(9)

Xaa(10) His Trp Gln Ala Xaa(11) Ile Met Gly Pro Asn Asp Ser Pro Tyr Xaa(12) Gly Gly Val Phe Phe Leu Xaa(13) Ile His Phe Pro Thr Asp Tyr Pro Xaa(14)

Lys Pro Pro Lys Xaa(15) Xaa(16) Xaa(17) Thr Thr Xaa(18) Ile Tyr His Pro Asn Ile Asn Ser Asn Gly Xaa(19)

Ile Cys Leu Asp Ile Leu Xaa(20) Xaa(21) Gln Trp Ser Pro Ala Leu Thr Ile Ser Lys Val Leu Leu Ser Ile Cys Ser Leu Leu Xaa(22)

Asp Xaa(23) Asn Pro Asp Asp Pro Leu Val Pro Glu Ile Ala Xaa(24)

Xaa(25) Tyr Xaa(26) Xaa(27) Asp Arg Xaa(28) Xaa(29) Tyr Xaa(30) Xaa(31) Xaa(32) Ala Xaa(33) Glu Trp Thr Xaa(34) Lys Tyr Ala Xaa(35) (SEQ ID No. 7)

wherein Xaa(1) represents Ala or Ser; Xaa(2) represents His or Asn; Xaa(3) represents Lys or Arg; Xaa(4) represents Ala, Ser or Asn; Xaa(5) represents Gly or Ala; Xaa(6) represents Arg or Lys; Xaa(7) represents Ala or Ser; Xaa(8) represents Gln or Ser; Xaa(9) represents Leu or Met; Xaa(10) represents Phe or Tyr; Xaa(11) represents Ser or Thr; Xaa(12) represents Gln or Ala; Xaa(13) represents Ser or Thr; Xaa(14) represents Leu or Phe; Xaa(15) represents Val or Ile; Xaa(16) represents Ala or Asn; Xaa(17) represents Leu or Phe; Xaa(18) represents Arg or Lys; Xaa(19) represents Ser or Asn; Xaa(20) represents Arg or Lys; Xaa(21) represents Ser or Asp; Xaa(22) represents Thr or Cys; Xaa(23) represents Ala or Pro; Xaa(24) represents Arg or His; Xaa(25) represents Val or Ile; Xaa(26) represents Lys or Gln; Xaa(27) represents Thr or Gln; Xaa(28) represents Ser, Lys or Glu; Xaa(29) represents Arg or Lys; Xaa(30) represents Asn or Gln; Xaa(31) represents Ala, Leu or Arg; Xaa(32) represents Ile, Ser or Thr; Xaa(33) represents Arg or Lys; Xaa(34) represents Arg, Lys or Gln; Xaa(35) represents Val, Ile or Met.

To further expand the library, each of the degenerate positions (Xaa) can be rendered even more degenerate by including other amino acid residues which are of the same "family" as the residues which appear in each of the UbCEs, e.g. Xaa(1) can be Gly, Ala, Val, Leu, Ile Ser or Thr (e.g. aliphatic), Xaa(22) can be Ser, Thr, Cys or Met (aliphatic-hydroxyl and sulfur-containing), etc. Alternatively, isosteric substitutions can be made without regard to, for example, charge or polarity of the amino acid sidechain. For instance, Xaa(17) can be Leu, Ile, Asn, Met, Phe or Tyr, as the sidechains of Ile, Asn and Met each occupy approximately the same steric space as Leu, and Tyr is isosteric for Phe. Likewise, where the degeneracy is conserved from the human and yeast homologs, the degenerate library can, at that position, only include, for example, the amino acid residue which occurs in the human UbCE. To illustrate, Xaa(3) is a Lysine in hUbCE and caUbCE, and Arginine in spUbCE. In a library which rejects conservative mutations of the human UbCE as equivalent, Xaa(3) would be Lys.

In a preferred embodiment, the combinatorial UBC library is produced by way of a degenerate library of genes encoding a library of polypeptides which each include at least a portion of potential UBC sequences. A mixture of synthetic oligonucleotides can be enzymatically ligated into gene sequences such that the degenerate set of potential UBC sequences are expressible as individual polypeptides, or alternatively, as a set of larger fusion proteins (e.g. for phage display) containing the set of UBC sequences therein.

There are many ways by which the library of potential UBC homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential UBC sequences. The synthesis of degenerate oligonucleotides is well known in the art (see, for example, Narang, SA (1983) *Tetrahedron* 39:3; Itakura et al. (1981) *Recombinant DNA, Proc 3rd Cleveland Sympos. Macromolecules*, ed. A. G. Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of UBC homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of, for example, degenerate UBC sequences created by combinatorial mutagenesis techniques.

In one illustrative screening assay, the candidate hUbCE or rapUBC gene products are displayed on the surface of a cell or viral particle, and the ability of particular cells or viral particles to bind other components of the ubiquitin pathway, such as E1 or E3 proteins (e.g. E6AP or E6AP complexes), ubiquitin, or a cell-cycle regulatory protein, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hUbCE or rapUBC can be used to score for potentially functional hUbCE or rapUBC homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening hUbCE or rapUBC combinatorial libraries. For instance, the pCANTAB 5 phagemid of the RPAS kit contains the gene which encodes the phage gIII coat protein. The hUbCE or rapUBC combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hUbCE or rapUBC gene insert. The resulting recombinant phage contain phagemid DNA encoding a specific candidate hUbCE or rapUBC, and display one or more copies of the corresponding fusion coat protein. The phage-displayed candidate hUbCE or rapUBC which are capable of binding a particular target protein, such as an E1 enzyme, an E3 protein (i.e. E6 or E6-AP), or a particular regulatory protein (such as p53 or p27), are selected or enriched by panning. For instance, the phage library can be panned on glutathione immobilized p53-GST fusion proteins or E6-GST or E6-AP-GST fusion proteins and unbound phage washed away from the cells. The bound phage is then isolated, and if the recombinant phage express at least one copy of the wild type gIII coat protein, they will retain the ability to infect *E. coli*. Thus, successive rounds of reinfection and panning can be employed to greatly enrich for UBC homologs that retain some ability to interact with normal targets of the wild-type enzyme and which can then be screened for further biological activities in order to differentiate agonists and antagonists. In an exemplary embodiment, by use of two or more target proteins in sequential panning steps, the phage display library can be used to isolate hUbCE or rapUBC homologs which are candidate antagonists of the normal cellular function of the naturally occurring UBC. For instance, isolating from the library those variants which retain the ability to bind, for example, either the papillomavirus E6 protein or the cellular E6-AP protein, but which are unable to bind p53, provides a set of hUbCE or rapUBC homologs some of which may be capable of antagonizing the ability of the corresponding wild-type enzyme to mediate ubiquitination of p53.

In yet another illustrative embodiment, the p53-dependent reporter construct described in the 08/176,937 application can be used to identify antagonists through their ability to enhance expression of the reporter gene by inhibiting the degradation of p53 wild-type hUbCE or rapUBC. Thus, a combinatorial library can screened by a detecting expression of the reporter gene, and appropriate clones isolated for further manipulation.

Other forms of mutagenesis can also be utilized to generate a combinatorial library from the subject UBC proteins. For example, hUbCE or rapUBC homologs (both agonist and antagonist forms) can be generated and isolated from a library by screening using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

An important goal of the present invention is to provide reduction of the UBC proteins to small functional units that can be ultimately used to generate UBC mimetics, e.g. peptide or non-peptide agents, which are able to disrupt binding of UBC with other cellular and/or viral proteins. Thus, such mutagenic techniques as described herein are particularly useful to map the determinants of the hUbCE or rapUBC protein which participate in protein-protein interactions involved in, for example, binding of the subject hUbCE or rapUBC to other proteins of the ubiquitin-conjugating system (both cellular and viral), as well as the target protein itself (e.g. a cell-cycle regulatory protein). To illustrate, the critical residues of hUbCE involved in molecular recognition of E6 and/or E6-AP can be determined and used to generate hUbCE-derived peptidomimetics which competitively inhibit hUbCE binding. By employing, for example, scanning mutagenesis to map the amino acid residues of hUbCE involved in binding E6AP, peptidomimetic compounds can be generated which mimic those residues in binding to E6AP, and which therefore can inhibit binding of the hUbCE to E6AP and interfere with the function of E6AP in regulating the cellular half-life of p53. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffinan et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71). Such peptidomimetics can serve as drugs which prevent the action of hUbCE in the destruction of, for example, p53. In like manner, peptidomimetics of caUbCE and spUbCE can be derived which may be useful in, for example, the generation of anti-mycotic agents.

Another aspect of the invention pertains to an antibody specifically reactive with the subject UBC proteins. For example, by using immunogens derived from the hUbCE or rapUBC protein of the present invention, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., the whole UBC protein or an antigenic fragment which is capable of eliciting an antibody response). Techniques for conferring immunogenicity on a protein or peptide include conjugation to carriers or other techniques well known in the art. An immunogenic portion of the subject UBC protein can be administered in the presence of adjuvant. The progress of immunization can be monitored by detection of antibody titers in plasma or serum. Standard ELISA or other immunoassays can be used with the immunogen as an antigen to assess the levels of antibodies. In a preferred embodiment, the subject antibodies are immunospecific for hUbCE antigenic determinants, e.g. antigenic determinants of a protein represented by SEQ ID No. 2 or a closely related human or non-human mammalian homolog (e.g. 90 percent homologous to SEQ ID No. 2, preferably at least 95 percent homologous and more preferably at least 97 percent homologous to SEQ ID No.2). In yet a further preferred embodiment of the present invention, the anti-hUbCE antibodies does not substantially cross react with a protein which is: e.g. less than 90 percent homologous with SEQ ID No. 2; e.g. less than 95 percent homologous with SEQ ID No. 2; e.g. less than 98–99 percent homologous with SEQ ID No.2. By "does not substantially cross-react", it is meant that: the antibody has a binding affinity for a non-homologous E2 enzyme which is less than 10 percent, more preferably less than 5 percent, and most preferably less than about 1–2 percent of the binding affinity of that antibody for the protein of SEQ ID No. 2; the antibody does not specifically bind a protein which is non-homologous to SEQ ID No. 2. Preferred antibodies against the subject caUbCE, spUbCE and rapUBC proteins have similar criteria, e.g., antibodies specific for caUbCE, spUbCE or rapUBC do not specifically bind proteins which do not share high sequence homology with SEQ ID No. 4, 6, or 13 respectively.

Following immunization, antisera selectively reactive with one or more of the subject UBCs can be obtained and, if desired, polyclonal anti-UBC antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256:495–497), the human B cell hybridoma technique (Kozbar et al., (1983) *Immunology Today,* 4:72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with the subject proteins and monoclonal antibodies isolated from a culture comprising such hybridoma cells.

The term antibody as used herein is intended to include fragments thereof which are also specifically reactive with the UBC proteins of the present invention. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-UBC portion.

Both monoclonal and polyclonal antibodies (Ab) directed against the subject ubiquitin conjugating enzymes, and antibody fragments such as Fab' and F(ab')$_2$, can be used as specialty chemicals to block the action of the enzyme and allow the study of, for example, the cell cycle or cell proliferation when the subject UBC is inhibited, e.g. by microinjection of anti-UBC antibodies.

Antibodies which specifically bind hUbCE or rapUBC epitopes can also be used in immunohistochemical staining of tissue samples in order to evaluate the abundance and pattern of expression of hUbCE or rapUBC. Anti-hUbCE or anti-rapUBC antibodies can be used diagnostically in immuno-precipitation and immuno-blotting to detect and evaluate hUbCE or rapUBC levels in tissue or bodily fluid as part of a clinical testing procedure. For instance, such measurements can be useful in predictive valuations of the onset or progression of tumors. Likewise, the ability to monitor hUbCE or rapUBC levels in an individual can allow determination of the efficacy of a given treatment regimen for an individual afflicted with such a disorder. The level of each of the subject UBCs can be measured in cells isolated from bodily fluid, such as in samples of cerebral spinal fluid or blood, or can be measured in tissue, such as produced by biopsy. Diagnostic assays using anti-hUbCE or anti-rapUBC antibodies can include, for example, immunoassays designed to aid in early diagnosis of a neoplastic or hyperplastic disorder, e.g. the presence of cancerous cells in the sample, e.g. to detect cells in which a lesion of the hUbCE or rapUBC gene has occurred.

Another application of anti-UBC antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of UBc can then be detected with antibodies, as, for example, reacting nitrocellulose filters lifted from infected plates with anti-UBC antibodies. Phage, scored by this assay, can then be isolated from the infected plate. Thus, the presence of hUbCE or rapUBC homologs can be detected and cloned from other human sources, i.e. to identify other closely homologous human isoforms, as well as to identify hUbCE or rapUBC homologs in other mammals.

Moreover, the nucleotide sequence determined from the cloning of the subject hUbCE or rapUBC from a human cell line will further allow for the generation of probes designed for use in identifying hUbCE or rapUBC homologs in other human cell-types, particularly cancer or other transformed or immortalized cells, as well as hUbCE or rapUBC homologs from other non-human mammals. Probes based on the yeast UbCE sequences, caUbCE and spUbCE, can be generated and used to identify and phenotype mycotic infections.

In addition, nucleotide probes can be generated from the cloned sequence of the hUbCE or rapUBC protein, which allow for histological screening of intact tissue and tissue samples for the presence of hUbCE or rapUBC mRNA. Similar to the diagnostic uses of anti-hUbCE or anti-rapUBC antibodies, the use of probes directed to hUbCE or rapUBC mRNA, or to genomic hUbCE or rapUBC sequences, can be used for both predictive and therapeutic evaluation of allelic mutations which might be manifest in, for example, neoplastic or hyperplastic disorders (e.g. unwanted cell growth). Used in conjunction with anti-hUbCE or anti-rapUBC antibody immunoassays, the nucleotide probes can help facilitate the determination of the molecular basis for a developmental disorder which may involve some abnormality associated with expression (or lack thereof) of an hUbCE or a rapUBC protein. For instance, variation in hUbCE or rapUBC synthesis can be differentiated from a mutation in the hUbCE or rapUBC coding sequence.

For example, the present method provides a method for determining if a subject is at risk for a disorder characterized by unwanted cell proliferation. In preferred embodiments, the subject method can be generally characterized as comprising detecting, in a tissue of a subject (e.g. a human patient), the presence or absence of a genetic lesion characterized by at least one of (i) a mutation of a gene encoding hUbCE or rapUBC, or (ii) the mis-expression of the UBC gene. To illustrate, such genetic lesions can be detected by ascertaining the existence of at least one of (i) a deletion of one or more nucleotides from the UBC gene, (ii) an addition of one or more nucleotides to the UBC gene, (iii) a substitution of one or more nucleotides of the UBC gene, (iv) a gross chromosomal rearrangement of the hUbCE or rapUBC gene, (v) a gross alteration in the level of a messenger RNA transcript of the hUbCE or rapUBC gene, (vi) the presence of a non-wild type splicing pattern of a messenger RNA transcript of the hUbCE or rapUBC gene, and (vii) a non-wild type level of the hUbCE or rapUBC protein. In one aspect of the invention there is provided a probe/primer comprising an oligonucleotide containing a region of nucleotide sequence which is capable of hybridizing to a sense or antisense sequence of SEQ ID No: 1 or SEQ ID No:12, or naturally occurring mutants thereof, or 5' or 3' flanking sequences, or intronic sequences naturally associated with the hUbCE or rapUBC gene. The probe is exposed to nucleic acid of a tissue sample; and the hybridization of the probe to the sample nucleic acid is detected. In certain embodiments, detection of the lesion comprises utilizing the probe/primer in, for example, a polymerase chain reaction (PCR) (see, e.g., U.S. Pat. Nos. 4,683,195 and 4,683,202), or, alternatively, in a ligation chain reaction (LCR) (see, e.g., Landegran et al. (1988) *Science* 241:1077–1080; and Nakazawa et al. (1994) *PNAS* 91:360–364), the later of which can be particularly useful for detecting even point mutations in the hUbCE or rapUBC gene. Alternatively, or additionally, the level of hUbCE or rapUBC protein can be detected in an immunoassay.

Also, the use of anti-sense techniques (e.g. microinjection of antisense molecules, or transfection with plasmids whose transcripts are anti-sense with regard to, e.g. UBC mRNA) can be used to investigate the role of each of the subject UBC proteins in the cell cycle and cell proliferation, by inhibiting endogenous production of that protein. Such techniques can be utilized in cell culture, but can also be used in the creation of transgenic animals.

Another aspect of the present invention concerns transgenic animals, e.g. as animal models for developmental and proliferative diseases, which are comprised of cells (of that animal) which contain a transgene of the present invention and which preferably (though optionally) express a recombinant form (agonist or antagonist) of one or more of the subject UBC enzymes in one or more cells in the animal. In preferred embodiments, the expression of the transgene is restricted to specific subsets of cells, tissues or developmental stages utilizing, for example, cis-acting sequences that control expression in the desired pattern. In the present invention, such mosiac expression of the subject UBC proteins can be essential for many forms of lineage analysis and can additionally provide a means to assess the effects of UBC mutations or overexpression that might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject receptor. For example, excision of a target sequence which interferes with the expression of the receptor can be designed to activate expression of that protein. This interference with expression of the subject protein can result from a variety of mechanisms, such as spatial separation of the UBC gene from the promoter element or an internal stop codon. Moreover, the transgene can be made wherein the coding sequence of the UBC gene is flanked by recombinase recognition sequences and is initially transfected into cells in a 3' to 5' orientation with respect to the promoter element. In such an instance, inversion of the target sequence will reorient the subject UBC gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the recombinant UBC gene can be regulated via regulation of recombinase expression.

Use of the these recombinase system to regulate expression of, for example, a dominant negative UBC gene, such as the Cys85Ser mutant or an antisense gene, requires the construction of a transgenic animal containing transgenes encoding both the Cre recombinase and the subject gene. Animals containing both the Cre recombinase and the UBC genes can be provided through the construction of "double" transgenic animals. A convenient method for providing such animals is to mate two transgenic animals each containing a transgene, e.g., the UBC gene and recombinase gene.

One advantage derived from initially constructing transgenic animals containing a UBC transgene in a recombinase-mediated expressible format derives from the likelihood that the subject UBC protein, whether antagonistic or agonistic, will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which the UBC transgene is silent will allow the study of, for example, the role of the p53 checkpoint in tissue or at developmental stages which can confer, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the transgene could remain silent into adulthood until "turned on" by the introduction of the trans-activator.

Methods of making knock-out or disruption transgenic animals are also generally known. See, for example,

*Manipulating the Mouse Embryo*, (Cold Spring Harbor Laboratory Press, Cold Spring Harbor, N.Y., 1986).

Furthermore, the present invention, by making available purified and recombinant forms of the subject UBC proteins, facilitates the development of assays that can be used to screen for drugs which inhibit the conjugating activity. For instance, in addition to agents which disrupt binding of a UBC protein to other cellular (or viral) proteins, inhibitors of the enzymatic activity of the subject E2 enzymes may prevent transfer of ubiquitin to the enzyme (by an E1 enzyme) or inhibit any downstream transfer of ubiquitin from the E2 enzyme to a cellular substrate or an intermediary E3 complex, e.g., an E6/E6-AP. In a preferred embodiment, the UBC inhibitor is a mechanism based inhibitor which chemically alters the enzyme, e.g. covalently binds Cys-85 of hUbCE or Cys-93 of rapUBC, and which is a specific inhibitor of that enzyme, e.g. has an inhibition constant 10-fold, 100-fold, or more preferably, 1000-fold different for human E2 enzymes other than the subject UBC enzyme. Inhibitor specificity can be improved, for example, by utilizing specificity subsites of the hUbCE enzyme involved in interactions between hUbCE and an E6/E6AP complex, or hUbCE and an E1 enzyme, which are unique to one of those complexes relative to other human E2 enzymes. Similar approaches can also be used to screen for drugs agonistic or antagonistic to rapUBC activities.

Assays for the measurement of ubiquitination can be generated in many different forms, and include assays based on cell-free systems, e.g. purified proteins or cell lysates, as well as cell-based assays which utilize intact cells. Assays as described herein can be used in conjunction with the subject E2 enzymes to generate a ubiquitin-conjugating system for detecting agents able to inhibit particular E2-mediated ubiquitination of a cellular or viral regulatory proteins. Such inhibitors can be used, for example, in the treatment of proliferative and/or differentiative disorders, to modulate apoptosis, and in the treatment of viral infections, such by adenoviruses or papillomaviruses. Similar assay systems can be constructed for the fungal homologs in order to detect inhibitors which may serve as anti-fungal agents. In preferred embodiments, the assay system employed for identifying anti-fungal agents are run side-by-side with the analogous assay system derived with the mammalian homolog of the UBC, e.g. hUbCE or rapUBC. Differential screening assays can be used to exploit any difference in mechanism or specificity between mammalian UBCs and yeast UBCs (including other yeast E2 enzymes) in order to identify agents which display a statistically significant increase in specificity for inhibiting the yeast enzymes relative to the mammalian enzymes. Thus, lead compounds which act specifically on pathogens, such as fungus involved in mycotic infections, can be developed.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential E2 inhibitors can be detected in a cell-free assay generated by constitution of a functional ubiquitin-protein ligase system in a cell lysate, such as generated by charging a ubiquitin-depleted reticulocyte lysate (Hersko et al. (1983) *J Biol Chem* 258:8206–6214) with one of the subject UBC enzymes and, as needed, an E1 enzyme, an E3 enzyme (cellular or viral in origin), ubiquitin, and a substrate for UBC-dependent ubiquitination. In an alternative format, the assay can be derived as a reconstituted protein mixture which, as described below, offers a number of benefits over lysate-based assays.

In yet other embodiments, the present assay comprises an in vivo ubiquitin-conjugating system, such as a cell able to conduct the regulatory protein through at least a portion of a ubiquitin-mediated proteolytic pathway.

The level of ubiquitination of the substrate protein brought about by the system is measured in the presence and absence of a candidate agent, and a decrease in the level ubiquitin conjugation is indicative of an inhibitory activity for the candidate agent. As described below, the level of ubiquitination of the regulatory protein can be measured by determining the actual concentration of protein:ubiquitin conjugates formed; or inferred by detecting some other quality of the subject protein affected by ubiquitination, including the proteolytic degradation of the protein. A statistically significant decrease in ubiquitination of the target protein in the presence of the test compound is indicative of the test compound being an inhibitor of E2-dependent ubiquitin conjugation.

In preferred in vitro embodiments of the present assay, the ubiquitin-conjugating system comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in conjugation of ubiquitin to a target protein, together with the target protein, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure specific ubiquitination or ubiquitin-mediated degradation of the target regulatory protein.

Each of the protein components utilized to generate the reconstituted ubiquitin-conjugating system are preferably isolated from, or otherwise substantially free of, other proteins normally associated with the proteins in a cell or cell lysate. The term "substantially free of other cellular proteins" (also referred to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

With respect to measuring ubiquitination, the purified protein mixture can substantially lack any proteolytic activity which would degrade the target protein and/or components of the ubiquitin conjugating system. For instance, the reconstituted system can be generated to have less than 10% of the proteolytic activity associated with a typical reticulocyte lysate, and preferably no more than 5%, and most preferably less than 2%. Alternatively, the mixture can be generated to include, either from the onset of ubiquitination or from some point after ubiquitin conjugation of the regulatory protein, a ubiquitin-dependent proteolytic activity, such as a purified proteosome complex, that is present in the mixture at measured amounts.

In the subject method, ubiquitin conjugating systems derived from purified proteins hold a number of significant advantages over cell lysate or wheat germ extract based assays (collectively referred to hereinafter as "lysates"). Unlike the reconstituted protein system, the synthesis and destruction of the target protein cannot be readily controlled for in lysate-based assays. Without knowledge of particular kinetic parameters for Ub-independent and Ub-dependent degradation of the target protein in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the target protein, as such lysates may continue to synthesize the protein during the assay, and will do so at unpredictable rates.

Using similar considerations, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the target protein itself has a relatively short half-life, especially if due to degradative processes other than the ubiquitin-mediated pathway to which an inhibitor is sought. For example, in assays for an inhibitor of HPV-induced ubiquitination of p53, lysate based systems can be difficult to use, in addition to the reasons set forth above, due to the short half-life of p53 even in extracts which lack HPV proteins. In such systems, the ability to measure HPV-mediated ubiquitination of p53 is made difficult by the already rapid, ongoing degradation of p53 presumably occurring by proteolytic processes which are not mediated by any HPV proteins.

The use of reconstituted protein mixtures allows more careful control of the reaction conditions in the ubiquitin-conjugating system. Moreover, the system can be derived to favor discovery of inhibitors of particular steps of the ubiquitination process. For instance, a reconstituted protein assay can be generated which does not facilitate degradation of the ubiquitinated protein. The level of ubiquitin conjugated protein can easily be measured directly in such as system, both in the presence and absence of a candidate agent, thereby enhancing the ability to detect a ubiquitination inhibitor. Alternatively, the Ub-conjugating system can be allowed to develop a steady state level of regulatory protein:Ub conjugates in the absence of a proteolytic activity, but then shifted to a degradative system by addition of purified Ub-dependent proteases. Such degradative systems would be amenable to identifying proteosome inhibitors.

The purified protein mixture includes a purified preparation of the regulatory protein and ubiquitin under conditions which drive the conjugation of the two molecules. For instance, the mixture can include a ubiquitin-activating enzyme (E1), a ubiquitin-conjugating enzyme (E2), and a nucleotide triphosphate (e.g. ATP). Alternatively, the E1 enzyme, the ubiquitin, and the nucleotide triphosphate can be substituted in the system with a pre-activated ubiquitin in the form of an E1::Ub conjugate. Likewise, a pre-activated ubiquitin can instead comprise an E2::Ub conjugate which can directly transfer the pre-activated ubiquitin to the target protein substrate.

Furthermore, the reconstituted mixture can also be generated to include at least one auxiliary substrate recognition protein (E3) which may be, for example, of cellular or viral origin. In illustrative embodiments described below, in order to generate an assay which approximates the ubiquitination of p53 in HPV-16 or HPV-18 infected cells, the reconstituted ubiquitin conjugating system may further include an E6 protein of HPV origin, as well as an E6-associated protein (E6-AP) of cellular origin.

Ubiquitination of the target regulatory protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated target protein assessed, using standard electrophoresis protocols, by measuring an increase in molecular weight of the target protein that corresponds to the addition of one or more ubiquitin chains. For example, one or both of the target protein and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the regulatory protein, including immunoblot analysis using antibodies specific for either the regulatory protein or ubiquitin, or derivatives thereof. As described below, the antibody can be replaced with another molecule able to bind one of either the regulatory protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the regulatory protein and ubiquitin conjugates in the gel by standard staining protocols, including coomassie blue and silver staining.

In another embodiment, an immunoassay or similar binding assay, is used to detect and quantify the level of ubiquitinated regulatory protein produced in the ubiquitin-conjugating system. Many different immunoassay techniques are amenable for such use and can be employed to detect and quantitate the regulatory protein:Ub conjugates. For example, the wells of a microtitre plate (or other suitable solid phase) can be coated with an antibody which specifically binds one of either the regulatory protein or ubiquitin. After incubation of the ubiquitin-conjugated system with and without the candidate agent, the products are contacted with the matrix bound antibody, unbound material removed by washing, and ubiquitin conjugates of the regulatory protein specifically detected. To illustrate, if an antibody which binds the regulatory protein is used to sequester the protein on the matrix, then a detectable anti-ubiquitin antibody can be used to score for the presence of ubiquitinated regulatory protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the substrate protein or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of regulatory protein (bound to the matrix via a conjugated ubiquitin moiety) is detected in each well. Alternatively, the microtitre plate wells can be coated with an antibody (or other binding molecule) which binds and sequesters the regulatory protein on the solid support, and detection of ubiquitinated conjugates of the matrix-bound regulatory protein are derivatively carried out using a detectable streptavidin derivative, such as an alkaline phosphatase/streptavidin complex.

In similar fashion, epitope-tagged ubiquitin, such as myc-ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated regulatory protein.

Other ubiquitin derivatives include detectable labels which do not interfere greatly with the conjugation of ubiquitin to the regulatory protein. Such detectable lables can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the regulatory protein. For example, the regulatory protein can be generated as a glutathione-S-transferase (GST) fusion protein. As a practical matter, such GST fusion protein can enable easy purification of the regulatory protein in the preparation of components of the ubiquitin-conjugating system (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the regulatory protein from the ubiguitin-conjugating system, and the level of ubiquitin immobilized can be measured as described. Likewise, where the matrix is generated to bind ubiquitin, the level of sequestered GST-regulatory protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the regulatory protein and an enzymatic activity are contemplated by the present method. For example, fusion proteins containing β-galactosidase or luciferase, to name but a few, can be employed as labels to determine the amount of regulatory protein sequestered on a matrix by virtue of a conjugated ubiquitin chain.

Moreover, such enzymatic fusion proteins can be used to detect and quantitate ubiquitinated regulatory protein in a heterogeneous assay, that is one which does not require separation of the components of the conjugating system. For example, ubiquitin conjugating systems can be generated to have a ubiquitin-dependent protease which degrades the regulatory protein. The enzymatic activity of the fusion protein provides a detectable signal, in the presence of substrate, for measuring the level of the regulatory protein ubiquitination. Similarly, in a non-degradative conjugating system, ubiquitination of the regulatory protein portion of the fusion protein can allosterically influence the enzymatic activity associated with the fusion the protein and thereby provides a means for monitoring the level of ubiquitin conjugation.

In binding assay-type detection steps set out above, the choice of which of either the regulatory protein or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the regulatory protein, (e.g., one order of magnitude or greater) sequestering the ubiquitin and detecting the amount of regulatory protein bound with the ubiquitin can provide less dynamic range to the detection step of the present method than the converse embodiment of sequestering the regulatory protein and detecting ubiquitin conjugates from the total regulatory protein bound to the matrix. That is, where ubiquitin is provided in great excess relative to the regulatory protein, the percentage of ubiquitin conjugated regulatory protein in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound regulatory protein. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

Furthermore, drug screening assays can be generated which do not measure ubiquitination per se, but rather detect inhibitory agents on the basis of their ability to interfere with binding of one of the subject UBC proteins with any other immediate upstream or downstream component of the ubiquitin conjugation pathway. In an exemplary binding assay, the compound of interest is contacted with a mixture generated from an isolated and purified E2 protein, such as hUbCE or rapUBC, and another component of the ubiquitin conjugation pathway which binds to one of the UBC proteins (e.g. a "UBC-associated protein"), such as an E1 or E3 protein, or other cellular substrates of the subject UBC. Detection and quantification of E2 complexes provides a means for determining the compound's efficacy at inhibiting (or potentiating) complex formation between the UBC-associated protein and the UBC protein. The efficacy of the compound can be assessed by generating dose response curves from data obtained using various concentrations of the test compound. Moreover, a control assay can also be performed to provide a baseline for comparison. In the control assay, isolated and purified UBC is added to a composition containing the UBC-associated protein, and the formation of UBC-containing complexes is quantitated in the absence of the test compound.

Complex formation between the UBC protein and UBC-associated protein may be detected by a variety of techniques, many of which are effectively described above. For instance, modulation in the formation of complexes can be quantitated using, for example, detectably labelled proteins (e.g. radiolabelled, fluorescently labelled, or enzymatically labelled), by immunoassay, or by chromatographic detection.

Typically, it will be desirable to immobilize either UBC or the UBC-associated protein to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST/UBC fusion proteins can be adsorbed onto glutathione sepharose beads (Sigma Chemical, St. Louis, Mo.) or glutathione derivatized microtitre plates, which are then combined with the UBC-associated protein, e.g. an $^{35}$S-labeled UBC-associated protein, and the test compound and incubated under conditions conducive to complex formation. Following incubation, the beads are washed to remove any unbound UBC-associated protein, and the matrix bead-bound radiolabel determined directly (e.g. beads placed in scintilant), or in the supernatant after the UBC complexes are dissociated, e.g. when microtitre plaste is used. Alternatively, after washing away unbound protein, the complexes can be dissociated from the matrix, separated by SDS-PAGE gel, and the level of UBC-associated protein found in the matrix-bound fraction quantitated from the gel using standard electrophoretic techniques.

In still further embodiments of the present assay, the ubiquitin-conjugating system is generated in whole cells, taking advantage of cell culture techniques to support the subject assay. For example, as described below, the ubiquitin-conjugating system (including the target protein and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the ubiquitin-conjugating system, including the regulatory protein, can be endogenous to the cell selected to support the assay. Alternatively, some or all of the components can be derived from exogenous sources. For instance, a virally derived E3 protein, such as an HPV E6 protein, can be introduced into the cell by recombinant techniques (such as through the use of an expression vector), as well as by microinjecting the E3 protein itself or mRNA encoding the E3 protein.

In any case, the cell is ultimately manipulated after incubation with a candidate inhibitor in order to facilitate detection of ubiquitination or ubiquitin-mediated degradation of the regulatory protein. As described above for assays performed in reconstituted protein mixtures or lysate, the effectiveness of a candidate inhibitor can be assessed by measuring direct characteristics of the regulatory protein, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate.

Indirect measurement of ubiquitination of the target protein can also be accomplished by detecting a biological activity associated with the regulatory protein that is either attenuated by ubiquitin-conjugation or destroyed along with the regulatory protein by ubiquitin-dependent proteolytic processes. As set out above, the use of fusion proteins comprising the regulatory protein and an enzymatic activity are representative embodiments of the subject assay in which the detection means relies on indirect measurement of ubiquitination of the regulatory protein by quantitating an associated enzymatic activity.

Where the regulatory protein has a relatively short half-life due to ubiquitin-dependent or independent degradation in the cell, preferred embodiments of the assay either do not require cell lysis, or, alternatively, generate a longer lived detection signal that is independent of the regulatory protein's fate after lysis of the cell. With respect to the latter embodiment, the detection means can comprise, for example, a reporter gene construct which includes a positive transcriptional regulatory element that binds and is responsive to the regulatory protein. For instance, where the regulatory protein of interest is p53, p53 responsive elements can be used to construct the reporter gene. These include p53 binding sequences set out in Example 7 and FIG. 9, as well as a creatine kinase enhancer, an interleukin-6 promoter, a c-fos promoter, a β-actin promoter, an hsc70 promoter, a c-jun promoter, a p53 promoter, and a CYC1 hybrid promoter containing a p53-binding sequence. The gene product is a detectable label, such as luciferase or β-galactosidase, and is produced in the intact cell. The label can be measured in a subsequent lysate of the cell. However, the lysis step is preferably avoided, and providing a step of lysing the cell to measure the label will typically only be employed where detection of the label cannot be accomplished in whole cells.

Moreover, in the whole cell embodiments of the subject assay, the reporter gene construct can provide, upon expression, a selectable marker. For instance, the product of the reporter gene can be an enzyme which confers resistance to antibiotic or other drug, or an enzyme which complements a deficiency in the host cell (i.e. thymidine kinase or dihydrofolate reductase). To illustrate, the aminoglcycoside phosphotransferase encoded by the bacterial transposon gene Tn5 neo can be placed under transcriptional control of a promoter element responsive to the level of target regulatory protein present in the cell. Thus, the level of expression of the phenotypic marker gene is lower in the absence of an inhibitor of ubiquitin-mediated proteolysis of the regulatory protein, and such inhibitors can be detected in the assay by an ability to confer the measured phenotypic trait. Such embodiments of the subject assay are particularly amenable to high through-put analysis in that proliferation of the cell can provide a simple measure of inhibition of the ubiquitin-mediated degradation of the regulatory protein.

In yet a further embodiment of the subject assay, the ubiquitin-conjugating system comprises a cell in which the biological activity of the target regulatory protein has been substantially impaired, the impairment being the result of abnormal ubiquitination of the regulatory protein. The cell, in the presence or absence of a candidate inhibitor, is subject to growth conditions that would ordinarily required the function of the regulatory protein for viability of the cell. Thus, an inhibitor of the ubiquitin-mediated degradation of the regulatory protein would restore the biological activity of the protein to the cell, and could easily be detected by the ability of the cell to proliferate. To further illustrate, the impairment of the regulatory protein can be the result of over expression of a cellular protein of the ubiquitin pathway, such as an E2 or E3 protein, which results in hyper-ubiquitination of the regulatory protein. Alternatively, the impairment can result from non-cellular agents, such as viral proteins, which increase the ubiquitin-mediated degradation of the regulatory protein. For example, as described above, expression of the HPV E6 protein can result in decreased levels of p53 in the cell due to the increased ubiquitin-dependent inactivation of the protein.

In embodiments of the subject method in which the target regulatory protein ordinarily acts as a negative regulator of mitotic events, impairment of the regulatory protein can result in a hyper-mitotic cell. The term hyper-mitotic cell denotes a cell having an impaired cell-cycle checkpoint which can allow the cell to proceed abherently toward subsequent mitotic stages and ultimately inhibits faithful proliferation of the cell. In the present of an agent able to inhibit the ubiquitin-mediated inactivation of the regulatory protein, progression of the hyper-mitotic cell through the cell-cycle can be reestablished under control of the regulatory protein and permit the cell to appropriately proliferate.

To illustrate, a p53-impaired cell can be generated by expression of the HPV viral protein E6. The concomitant decrease in p53 levels brought about by E6 expression does not in and of itself cause abherent mitotic events to occur. However, exposure of the impaired cell to an agent (i.e. chemical or environmental) that ordinarily induces cell-cycle arrest at the p53 checkpoint can result in inappropriate exit of the cell from the chemically or environmentally induced arrest. This type of checkpoint override can ultimately be lethal to the cell. Such arresting agents can include exposure to DNA damaging radiation or DNA damaging agents; inhibition of DNA synthesis or repairmen using DNA polymerase inhibitors such as hydroxyurea or aphidicolin; topoisomerase inhibitors such as 4'-dimethylepipodophyllotoxin (VM-26); or agents which interfere with microtubule assembly, such as nocadazole and taxol.

With respect to embodiments in which the regulatory protein ordinarily acts as a mitotic activator, impairment of the protein's activity by ubiquitination can generate a hypomitotic cell in which progression of the cell through at least a portion of the cell-cycle is repressed. In the presence of an inhibitor of ubiquitin-dependent degradation of the regulatory protein, the activity of the mitotic activator is restored and the cell can proliferate at an greater rate relative to the untreated cell. Agents to be tested for their ability to act as inhibitor of ubiquitin-dependent degradation of the regulatory protein in the present assay can be those produced by bacteria, yeast or other organisms, or those produced chemically.

With respect to sources for the proteins constituting the ubiquitin-conjugating system, particularly to generate the reconstituted protein mixture, many species of the enzymes and other proteins involved in ubiquitination have been identified, and in a significant number of instances, have been cloned so that recombinant sources exist. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-sepharase) in the presence of ATP. As described in Example 2, such a protocol can be used to purify recombinantly expressed E1. Moreover, E1 enzymes bound to the immobilized ubiquitin can be exchanged with E2 enzymes. Thus, both E1 and E2 enzymes can be specifically purified on such columns, and can be recovered after elution with, for example, dithiothreitol. Under appropriate elution conditions, ubiquitin activated E1 or E2 complexes can be isolated and, as described herein, used in the present assay to increase the selectivity of the assay for an inhibitor of a particular step of ubiquitin-conjugation. Moreover, with minor changes, this protocol can be used to isolate E1 Ub or E2:Ub conjugates (e.g. activated ubiquitin conjugates) for use in the reconstituted protein mixture.

Identification of enzymes involved in the ubiquitin pathway from different sources have facilitated the cloning of corresponding genes. For instance, genes encoding E1 enzymes have been cloned from various organisms (see, for example, Adams et al. (1992) *Nature* 355:632–634; Handley et al. (1991) *PNAS* 88:258–262; Handley et al. (1991) *PNAS* 88:7456; Hatfield et al. (1990) *J. Biol. Chem.* 265:15813–15817; Kay et al. (1991) *Nature* 354:486–489; McCrath eg al. (1991) *EMBO J* 10:227–236; Mitchell et al. (1991) *Nature* 354:483–486; and Zacksenhaus et al. (1990) *EMBO J* 9:2923–2929). The sequences of various cloned E1 enzymes predict proteins of roughly 100 kd, and which contain the nucleotide-binding consensus sequence Gly-Xaa-Gly-Xaa-Xaa-Gly (McGrath et al. (1991) *EMBO J* 10:227–236). For example, the gene UBA1 has been cloned from *S. cerevisiae* and shown to encode a 114 kd E1 enzyme (McGrath et al., supra). Moreover, more than one E1 species has been detected in the same cell-type, suggesting that two or more different E1 enzymes can exist. It is not yet known whether the different E1 enzymes are enzymatically similar, or if they collaborate with specific sets of ubiquitin-conjugating enzymes. In either case, each of the E1 species can be used to generate the ubiquitin-conjugating system of the subject method.

In contrast to the ubiquitin-activating enzyme (E1), where it is generally believed that there are relatively few different species of the enzyme in a given cell, eukaryotic cells can express a large and diverse array of E2 enzymes. This remarkable variety of E2 enzymes, along with experimental evidence, has implicated the E2 enzyme as the principle determinant of substrate selectivity in the ubiquitin system. The E2 enzyme, as set out above, catalyzes isopeptide bond formation between ubiquitin and substrate proteins, either with or without the aid of a substrate recognition factor (ubiquitin-ligase protein; E3 ). Accordingly, in addition to the subject UBC proteins, e.g., UbCE and rapUBC, the subject assays can be performed with other E2 enzymes. For instance, several major species of E2 enzymes have been identified and purified by ubiquitin-affinity chromatography of extracts from rabbit reticulocytes (Pickart et al. (1985) *J Biol Chem* 260:1573–1581), yeast (Jentsch et al. (1987) *Nature* 329:131–134), and wheat (Sullivan et al. (1989) *PNAS* 86:9861–9865). Furthermore, many genes encoding E2 enzymes have been cloned and characterized, most notably in the yeast *Sacchromyces cerevisiae*, where the phenotypic consequences of their inactivation can be readily assessed. More than 10 yeast E2 genes have been identified to date (see Jentsch (1992) *Annu Rev Genet* 26:179–207; and Jentsch (1992) *Trends Cell Biol* 2:98–103), and there evidence for over 20 E2 genes in the plant *Arabipodopsis* (Cook et al. (1992) *J Biol Chem* 267:15116–15121). Additionally, E2 enzymes have been cloned from nematode (Zhen et al. (1993) *Mol Cell Biol* 13:1371–1377), drosophila (Muralidher et al. (1993) *Neuron* 11:253–266; and Koken et al. (1991) *PNAS* 88:3832–3836), bovine (Chen et al. (1991) *J Biol Chem* 266:15698–15704) and human cells (Koken et al. (1992) *Genomics* 12:447–453; Koken et al. (1991) *PNAS* 88:8865–8869; and Schneider et al. (1990) *EMBO J* 9:1431–1435). Other E2 enzymes can be substituted in the subject assays in place of the UbCE or rapUBC proteins of the present invention, or can be provided in addition to a UbCE or rapUBC protein, e.g., in a differential screening assay.

Some ubiquitin-conjugating enzymes require accessory factors, E3 proteins, for the recognition of certain protein substrates. Two E3 proteins, E3α and E3β, have been identified from rabbit reticulocytes (Reiss et al. (1989) *J. Biol. Chem.* 264:10378–10383; and Reiss et al. (1990) *J. Biol. Chem.* 265:3685–3690). A yeast gene (UBR1) encoding an E3 functionally similar to rabbit E3α has also been cloned (Bartel et al. (1990) *EMBO J* 9:3179–3189). Rabbit E3α and yeast UBR1 bind to substrates with N-terminal amino acid residues that are basic or have bulky hydrophobic side chains, while the E3β recognizes small unchanged residues at the N-terminus of substrates. In addition to the E3 proteins that recognize the N-terminus of protein substrates, other E3 proteins (collectively know as E3γ, capable of recognizing internally located signals, have been suspected.

Proteins that facilitate ubiquitin-conjugation reactions without physically interacting with E2 enzymes can also be classed as E3 proteins. By this definition, the E6 oncoprotein of the papillomavirus is regarded as an E3 protein, as binding of E6 triggers the ubiquitination and degradation of p53. For example, recombinant E6 protein from the high-risk HPV-18 (SEQ ID No.14), as well as the cellular factor E6-AP (SEQ ID No.15), are available for use in the subject assay.

The regulatory protein provided in the subject assay can be derived by purification from a cell in which it is exogenously expressed, or from a recombinant source of the protein. For example, cDNA clones are available for a number of regulatory proteins, including p53 (Oren et al. (1983) *EMBO J* 2:1633–1639); p27 (Polyak et al. (1994) *Cell* 78:59–66; and Toyoshima et al. (1994) *Cell* 78:67–74); c-myc (Hann et al. (1988) *Cell* 52:185–195); N-myc (Curran et al. (1987) *Oncogene* 2:79–84); MATα2 (Hochstrasser et al. (1990) *Cell* 61:697–708); and E1A (Salvicek et al. (1988) *EMBO J* 7:3171–3180).

Additionally, the subject ubiquitin conjugating enzyme can be used to generate an interaction trap assay for subsequently detecting inhibitors of hUbCE or rapUBC biological activity (see, for example, U.S. Pat. No: 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696) In an illustrative embodiment, *Saccharomyces cerevisiae* YPB2 cells are transformed simultaneously with a plasmid encoding a GAL4db-hUbCE fusion and with a plasmid encoding the GAL4ad domain fused to p53 or E6AP. Moreover, the strain is transformed such that the GAL4-responsive promoter drives expression of a phenotypic marker. For example, the ability to grow in the absence of histidine can depends on the expression of the HIS3 gene if it is under control of a GAL4-responsive promoter and, therefore, indicates that a functional GAL4 activator has been reconstituted through the interaction of hUbCE and p53 or E6AP. Thus, agent able to inhibit hUbCE interaction with one of these proteins will result in yeast cells unable to growth in the absence of histidine. Alternatively, the phenotypic marker can be one which provides a negative selection when expressed such that agents which disrupt the hUbCE interactions confer positive growth selection to the cells.

In one embodiment of the invention, the target regulatory protein is the tumor suppressor p53, and any one of the above assays protocols is used to identify inhibitors of ubiquitin-mediated destruction of p53, such as by disrupting interaction of hUbCE or rapUBC with p53, or interactions between hUbCE or rapUBC and other proteins of the ubiquitin system such as E6 or E6AP, or alternatively, by mechanistically inhibiting the enzymatic activity of the enzyme. Many lines of evidence point to the importance of p53 in human carcinogenesis. For instance, mutations within the p53 gene are the most frequent genetic aberration thus far associated with human cancer. Although p53 can block the progression of the cell cycle when artificially expressed at high levels, it appears to be dispensable for normal development. Thus, for mice containing homozygous deletions and humans harboring germline mutations of p53, development is normal and p53 protein is expressed at very low levels in most cell types. Emerging evidence, however, suggests that p53 is a checkpoint protein that plays an important role in sensing DNA damage or regulating cellular response to stress. Under normal conditions, p53 is an unstable protein and is present at very low levels in the cell, and the level of p53 in a cell appears to be controlled at least in party by degradation involving the ubiquitin system and, based on data presented herein, is likely to be mediated by the subject hUbCE or rapUBC. Treating cells with UV light or X rays dramatically reduces the rate of p53 degradation, leading to a rapid increase in its concentration in the cell and presumably inducing the transcription of genes that block passage through the restriction point. However, while normal cell lines irradiated in $G_1$ fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins. An inhibitor developed using the subject hUbCE or rapUBC in a ubiquitin-conjugating assay or by rational drug design could subsequently be used therapeutically to enhance the function of the p53 checkpoint by increasing the steady state concentration of p53 in the treated cell. Given that elevated levels of wild-type p53 protein can lead to apoptosis in a variety of transformed cell types (Yonish-Rouach et al. (1991) *Nature* 352:345–347; Shaw et al. *PNAS* 89:4495–4499; and Caelles et al. (1994) *Nature* 370:220–223), inhibitors of hUbCE or rapUBC-mediated degradation of p53 may be attractive therapeutic agents not only in cervical cancer, but also other cancer types, by increasing the fortitude of the checkpoint in transformed cells which contain wild-type p53, or by offsetting a diminishment in p53 activity by increasing the level of (mutant) p53. Moreover, such agents can also be used prophylactically in normal cells to increase p53 levels and thereby enhance the protection against DNA damaging agents when it is known that exposure to damaging agents, such as radiation, is imminent.

Moreover, the oncogenic activity of certain viruses, such as the simian virus 40 (SV40), the adenovirus type 5 (Ad5), and the high human papilloma virus types 16 and 18 (HPV16 and HPV18), has been correlated with the virus' ability to interact with and inactivate the cellular p53 protein. In the instance of the high-risk papilloma viruses, the association of the viral oncoprotein E6 with p53 leads to the specific ubiquitination and degradation of p53. This has suggested a model in which E6 immortalizes cells by deregulating cell growth control through the elimination of the p53 tumor suppressor protein. This models accounts for the observations that p53 levels are very low in HPV-immortalized cells and that the half-life of p53 in HPV16-immortalized keratinocytes is shorter than in primary keratinocytes. Thus, the present invention can be employed in the identification of an agent that can block the ubiquitin dependent degradation of p53 as mediated by E6, and thereby block proliferation of HPV-transformed cells.

The subject human ubiquitin conjugating enzyme is likely to be involved in altering the activity of other cellular proteins, particularly proteins which seem to have short half-lives, and the present invention contemplates the use of hUbCE or rapUBC inhibitors, including antagonistic forms of the hUbCE or rapUBC protein, to inhibit the ubiquitination of other cellular proteins by hUbCE or rapUBC. For example, in another embodiment, the regulatory protein ubiquitinated by hUbCE or rapUBC is the myc oncoprotein. The myc regulatory protein is activated by translocation or mutation in many B-cell lymphomas or by amplification in tumor types, such as small cell lung cancer and breast cancer. The c-myc gene is the cellular homolog of the viral oncogene v-myc, which is found in a number of avian and feline retroviruses which induce leukemia and carcinomas. Myc has been implicated in the control of normal cell proliferation by many studies. In particular, it is one of the immediate early growth response genes that are rapidly induced in quiescent cells upon mitogenic induction, suggesting that it plays some role in mediating the transition from quiescence to proliferation. However, increased levels of myc itself is not sufficient to cause proliferation. In fact, in normal cells the opposite happens and the cell undergoes apoptosis. Therefore, inhibitors identified in the present assay can be used to effectively induce apoptosis in cells which do not normally overexpress myc. For example, specific delivery of these agents to lymphocytes can be used to inhibit proliferation of B- and/or T-cells in order to induce clonal deletion and generate tolerance to particular antigens.

In tumor cells, on the other hand, elevated or deregulated expression of c-myc is so widespread as to suggest a critical role for myc gene activation in multi-stage carcinomas (Field et all. (1990) *Anticancer Res* 10:1–22; and Spencer et al. (1991) *Adv Cancer Res* 56:1–48). However, such overexpression of myc in these cells is typically believed to be accompanied by expression of other cellular proteins, such as bcl-2. Interestingly, however, almost all tumor cells tested that overexpress myc readily undergo apoptosis in the presence of cytotoxic and growth-inhibitory drugs (Cotter et al. (1990) *Anticancer Res* 10:1153–1159; and Lennon et al. (1990) *Biochem Soc Trans* 18:343–345). Therefore, inhibitors of the ubiquitin-mediated degradation of myc can be used to further deregulate the expression of myc in order to render the cells even more sensitive to a chemotherapeutic treatment, or to possibly upset the careful balance of the transformed cell and cause apoptosis to occur evenin the absence of a second cytotoxic drug.

The regulation of cyclin by ubiquitination is yet another therapeutic target which may implicate hUbCE or rapUBC inhibitors. Cyclin degradation is a key step governing exit from mitosis and progression into the next cell-cycle. For example, the transition from metaphase to anaphase which marks the end of mitosis in induced by the degradation of cyclin by a ubiquitin-mediated pathway, which in turn leads to the inactivation of cyclin-dependent kinases (cdk) operational at that cycle-cycle stage. As cells enter interphase, cyclin degradation ceases, cyclin accumulates and, as a result of a complex series of post-translational modifications, cyclin/cdk complexes are activated as kinases which drive the cell through mitosis. Cyclin degradation is thus one of the crucial events in exiting mitosis. Indeed, cyclin mutants that retain the ability to activate the cdk complexes, but which cannot be degraded, arrest the cell-cycle in mitosis. Similar cyclin-dependence exists at other points of the cell-cycle as well. Thus, inhibitors of ubiquitin-mediated degradation of a cyclin (such as where the cyclin is chosen from cyclin A, B, C, D1, D2, D3, E or F) can be used as antiproliterative agents.

Yet another candidate substrate of for E2 enzymes is the cyclin-dependent kinase inhibitor $p27^{kip1}$ (Polyak et al. (1994) *Cell* 78:59–66; and Toyoshima et al. (1994) *Cell* 78:67–74). This protein has been implicated in $G_1$ phase arrest, such as mediated by TGF-β and cell-cell contact. As described in the appended examples, we have found that ubiquitin conjugating enzymes are able to ubiquitinate p27, indicating that cellular turnover of that protein is dependent at least in part on ubiquitin-mediated destruction. Consequently, inhibition of ubiquitin transfer to p27 may result in accumulation of this cell-cycle inhibitor. An agent which inhibits the E2-mediated degradation of p27 would therefore be a cytostatic agent.

Such cytostatic agents would be useful for inhibiting proliferation of both normal and transformed cells. For example, an inhibitor of E2-mediated ubquitination of p27 could be used to prevent proliferation of lymphocytes, much the same as rapamycin and the like, and could be used as an immunosuppressant. Likewise, accumulation of p27 in fibroblasts could be used as part of a therapy for the treatment of a connective tissue disorder, or for controlling would healing processes.

P27 modulating agents may also be used for the treatment of hyperplastic epidermal conditions, such as psoriasis, as well as for the treatment of neoplastic epidermal conditions such as those characterized by a high proliferization rate for various skin cancers, as for example basal cell carcinoma and squamous cell carcinoma.

Normal cell proliferation is generally marked by responsiveness to negative autocrine or paracrine growth regulators, such as members of the TGF-β family, e.g. TGF-β1, TGF-β2 or TGF-β3, and related polypeptide growth inhibitors, e.g. activins, inhibins, Müillerian inhibiting substance, decapentaplegic, bone morphogenic factors, and vg1 (e.g. terminal differentiation inducers). Ordinarily, control of cellular proliferation by such growth regulators, particularly in epithelial and hemopoietic cells, is in the form of growth inhibition with p27 accumulation being associated with at least TGF-β response. This is generally accompanied by differentiation of the cell to a post-mitotic phenotype. However, it has been observed that a significant percentage of human cancers derived from these cells types display a reduced responsiveness to growth regulators such as TGF-β. For instance, some tumors of colorectal, liver epithelial, and epidermal origin show reduced sensitivity and resistance to the growth-inhibitory effects of TGF-β as compared to their normal counterparts. Treatment of such tumors with antagonists of ubiquitination of p27 provides an opportunity to restore the function of a TGF-β mediated checkpoint.

The subject E2 inhibitors can also be used in the treatment of hyperproliferative vascular disorders, e.g. smooth muscle hyperplasia (such as atherosclerosis) or restenosis, as well as other disorders characterized by fibrosis, e.g. rheumatoid arthritis, insulin dependent diabetes mellitus, glomerulonephritis, cirrhosis, and scleroderma, particularly proliferative disorders in which loss of TGF-β autocrine or paracrine signaling is implicated. For example, restinosis continues to limit the efficacy of coronary angioplasty despite various mechanical and pharmaceutical interventions that have been employed. An important mechanism involved in normal control of intimal proliferation of smooth muscle cells appears to be the induction of autocrine and paracrine TGF-β inhibitory loops in the smooth muscle cells (Scott-Burden et al. (1994) *Tex Heart Inst J* 21:91–97; Graiger et al. (1993) *Cardiovasc Res* 27:2238–2247; and Grainger et al. (1993) *Biochem J* 294:109–112). Loss of sensitivity to TGF-β, or alternatively, the overriding of this inhibitory stimulus such as by PDGF autostimulation, can be a contributory factor to abnormal smooth muscle proliferation in restinosis. It may therefore be possible to treat or prevent restenosis by the use of agents which inhibit ubiquitination of p27, thereby causing its accumulation.

Yet a further possible substrate of the subject hUbCE or rapUBC is the fos oncogene product, which can undergo ubiquitin-mediated degradation in a cell and has been implicated in neoplastic transformation as well as in mediating the action of a variety of extracellular stimuli. The control of gene expression by c-fos is believed to play a critical role in cellular proliferation and developmental responses, and alterations in the normal pattern of c-fos can lead to oncogenesis. Given the prominence of c-fos as an early response gene, apparent over-expression and prolonged lifetime of c-fos, as may be caused by an inhibitor of the ubiquitin-mediated degradation of c-fos, might sufficiently unbalance the cell-cycle and cause cell death. Alternatively, such inhibitors can be used to mimic the effects of an external stimulus on the cell, such as treatment with a cytokine.

Exemplification

The invention now being generally described, it will be more readily understood by reference to the following examples which are included merely for purposes of illustration of certain aspects and embodiments of the present invention, and are not intended to limit the invention.

We have defined the biochemical roles of hUbCE and E6AP in the E6 stimulated ubiquitination of p53 in vitro and have shown that inhibition of these enzymes in vivo can lead to an inhibition of E6-stimulated p53 degradation. As described in the examples below, inhibition of hUbCE and E6AP enzyme function in vivo causes an inhibition of E6-stimulated p53 degradation. The level of inhibition achieved in the micro-injection experiments in Example 8 was 25–30%. This may be a consequence of not every injected cell achieving high level expression of the injected construct, a phenomenon we have noted before in many different systems. It may also suggest that there is some redundancy in the cellular ubiquitin conjugation machinery, or that the intracellular concentrations of E1, hUbCE and E6AP are not rate-limiting for p53 degradation in the cell line used. All of our data suggest that E6 is absolutely required for ubiquitination of p53 in our in vitro and in vivo assay systems. We are currently investigating the possibility that hUbCE and E6AP are involved in the normal turnover of p53, with the possible involvement of an, as yet, unidentified cellular E6 homolog.

EXAMPLE 1

Cloning and Expression of a Novel Human Ubiquitin-conjugating Enzyme

The cDNA encoding the human ubiquitin-conjugating enzyme of the present invention was cloned from HeLa cells (ATCC CCL2). Briefly, polyadenylated RNA was isolated from cultured HeLa cells and first strand cDNA was prepared following standard protocols (c.f, Chomczynski U.S. Pat. No. 4,843,155; and Sambrook et al. *Molecular Cloning: A Laboratory Manual*, CSHL Press, Cold Spring Harbor, N.Y. (1989)). Using the nested PCR primer sets 5'-(GC)$_3$AAGCTTTAYGARGGWGGWGTYTTYTT-3' (SEQ ID No. 8), 5'-(GC)$_3$GAATTCACNGCRTAYTTYTTNGTCCCAYTC-3' (SEQ ID No. 9) and 5'-(GC)$_3$AAGCTTCCNGTNGGNG-AYTTRTTYCAYTGGCA-3' (SEQ ID No. 10), 5-(GC)$_3$G-AATTCATNGTNARNGCNGGCGACCA-3' (SEQ ID No. 11), which also provided convenient restriction sites in the PCR products, the coding sequences for the hUbCE gene was amplified from the HeLa cDNA library, and a HindIII-EcoRI fragment therefrom was subsequently ligated into a pBluescript II KS+ phagemid (pKS+ Stratagene catalog no. 212207) for further manipulation. The resulting pKS-hUbCE construct was amplified in XL1-Blue Cells (Strategene Catalog no. 260268), and double stranded construct purified. The nucleic acid sequence determined for the hUbCE clone is represented in SEQ ID NO. 1, and the corresponding deduced amino acid sequence is provided in SEQ ID No. 2.

The hUbCE gene was subsequently sub-cloned from pKS+ into other expression vectors to generate gene constructs for producing the recombinant hUbCE protein in either bacterial or insect cells. In some instances, the recombinant hUbCE was provided with exogenous sequences to produce fusion proteins, where the additional sequences of the fusion protein facilitate its purification. For example, after further amplification, the pKS-E2 construct was cut with XhoI and EcoRI, and the fragment containing the hUbCE coding sequence sub-cloned into a pGEX vector (Pharmacia catalog no. PGEX-4T) previously digested with SalI and EcoRI. The resulting pGEX-hUbCE construct encoded a glutathione-S-transferase (GST)/hUbCE fusion (Smith et al. (1988) *Gene* 67:31–40). The pGEX construct was introduced into *E. coli* by transformation, and the transformants grown in liquid media (LB) in the presence of IPTG. Purification of GST/hUbCE fusion protein was by standard protocols (*Current Protocols in Molecular Biology*, eds. Ausubel et al. (NY:John Wiley & Sons, 1991); Pharmacia instruction booklet (for catalog no. 27-4570)) using a glutathione-sepharose column (Pharmacia catalog no. 27-4570). Treatment with thrombin removed the GST domain from the fusion protein.

Alternatively, the hUbCE coding sequence was excised from the pKS-hUbCE construct as a HindIII-EcoRI fragment and ligated into pVL1393 cut with Sma I and Eco I. Briefly, the hUbCE gene fragment was purified by agarose gel separation, and ligated into the baculorvirus vector pVL1393 (Invitrogen catalog no. V1392-20) previously cut with Sma I and Bgl II. The pVL1393-hUbCE construct was then used to transfect spodoptera frugiperda (Sf9 cells, ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin No.* 1555, College Station, Tex.; Luckow et al. (1988) *Bio/technology* 6:47–55; and Miller et al., in *Genetic Engineering, Vol.* 8 ed. Setlow and Hollaender (Plenum Press: New York) pages 277–298). Transfected cells are grown until cells begin to lose their adherence to the culture plate surface, at which time the cells are harvested, collected by centrifugation, and lysed. The lysate is clarified by centrifugation to remove the cell wall debris, and the hUbCE can be purified from the lysate.

For instance, the hUbCE protein was isolated on an E1:ubiquitin charged column. Isolation of enzymes of the ubiquitin-conjugating system has been greatly assisted by "covalent" ubiquitin-affinity chromatography (Crechanover et al. (1982) *J. Biol. Chem.* 257:2537–2542; and Pickart et al. (1985) *J. Biol. Chem.* 260:1573–1581). This method takes advantage of the fact that the E1 enzyme is capable of forming a thiol ester with immobilized ubiquitin (e.g. ubiquitin-Sepharose) in the presence of ATP. Moreover, E1 enzymes bound to the immobilized ubiquitin can be exchanged with the subject hUbCE protein. Thus, both E1 and the subject hUbCE protein can be specifically purified on such columns, and can be recovered after elution with, for example, dithiothreitol. Moreover, with minor changes, this protocol can be used to isolate hUbCE:Ub conjugates (e.g. activated ubiquitin conjugates) for use in therapeutic target assays.

As described in U.S. patent application Ser. No. 08/176, 937, the an E1-containing lysate was applied to a sepharose-ubiquitin column (Hershko et al. (1983) *J. Biol. Chem.* 257:2537–2542) in the presence of ATP (e.g. 5 mM ATP, 10 mM MgCl$_2$, and 0.2 mM dithiothreitol, 50 mM Tris-HCl (pH 7.2)). The column was washed several times with this buffer. A clarified lysate of the hUbCE-producing insect cells, adjusted to 50 mM Tris-HCl (pH 7.2), 5 mM ATP, 10 mM MgCl$_2$, and 0.2 mM dithiothreitol, was then applied to the Ub:E1 column, washed, then eluted to remove any remaining ub:E1 (e.g. hUbCE will be exchanged for E1 on the column). The subject hUbCE protein was then eluted from the column by washing with 50 mM Tris-HCl (pH 9.0) containing 2 mM dithiothreitol.

In another exemplary embodiment, the recombinant hUbCE protein is generated as a poly(His) fusion protein for purification on a Ni$^{2+}$ metal column. An XhoI to EcoRI fragment of the pKS construct is cloned into the pBlueBac A baculovirus (Intvitrogen catalog no. V360-20) previously digested with XhoI and EcoRI. Following the manufacturer's protocols, the His$_6$-hUbCE fusion protein is then expressed in Sf9 insect cells, and purified on a Ni$^{2+}$ charged sepharose resin (Invitrogen catalog no. R801; see also Hochuli et al. (1987) *J. Chromatography* 411:177–184; and Janknecht et al. (1991) *PNAS* 88:8972–8976). Following purification of the fusion protein, the His$_6$ tag can be removed by treatment with entrokinase.

EXAMPLE 2

Isolation of components of an in vitro ubiquitin conjugating system

Ubiquitin was obtained from commercial sources, and the remaining protein components of the reconstituted protein system were cloned from HeLa cells (ATCC CCL2). Briefly, polyadenylated RNA was isolated from cultured HeLa cells and first strand cDNA was prepared following standard protocols (c.f., Chomczynski U.S. Pat. No. 4,843,155; and Sambrook et al. *Molecular Cloning: A Laboratory Manual*, CSHL Press, Cold Spring Harbor, N.Y. (1989)). PCR primers, designed to amplify DNA sequences encoding each of the component proteins, as well as provide convenient restriction sites to the PCR products, were used to isolate coding sequences for a human E1, human p53, HPV-18 E6, human E6-AP, and various human E2's, which were subsequently ligated into a pBluescript II KS+ phagemid (pKS+ Stratagene catalog no. 212207) for further manipulation. As described below, each of the component proteins genes were subsequently sub-cloned from pKS+ into other expression vectors to generate gene constructs for producing the recombinant proteins in either bacterial or insect cells. In some instances, the recombinant proteins have been provided with exogenous sequences to produce fusion proteins, where the additional sequences of the fusion protein facilitate its purification.

i) Human E1

Utilizing the primers 5'-(GC)$_3$AAGCTTATGTCCAGCTCGCCGCTGTCCAAG-3' and 5'-(GC)$_3$GGATCCTCAGCGGATGGTGTATCGGACATA-3'. The coding sequence for a human E1 (SEQ ID No. 14) was amplified from a HeLa cell cDNA library. The PCR amplification product containing the E1 coding sequences was purified and cut with Hind III and Bam HI (restriction sites provided by the PCR primers), and ligated into the pKS+ phagemid. The resulting pKS-E1 construct was amplified in XL1-Blue Cells (Strategen catalog no. 260268), and double stranded construct purified.

A Hind III/fill to BamHI fragments containing the E1 coding sequence was isolated from the pKS-E1 construct, where "Hind III/fill" indicates that a Hind III overhand generated in the fragment has been filled to form a blunt-end using Klenow and dNTPs. The E1 gene fragment was purified by agarose gel separation, and ligated into the baculorvirus vector pVL1393 (Invitrogen catalog no. V1392-20) previously cut with Sma I and Bgl II. The pVL1393-E1 construct was used to transfect spodoptera frugiperda (Sf9) cells) (ATCC CRL 1711), and the cells maintained in insect cell culture media (Grace's Antheraea medium) supplemented with 10% FBS, lactal bumin hydrolysate, TC yeastolate and glutamate (Invitrogen catalog no. B823) following standard protocols (Invitrogen product guide; Summers and Smith (1987); *Texas Agricultural Experiment Station Bulletin No.* 1555, College Station, Tex.; Luckow et al. (1988) Bio/technology 6:47–55; and Miller et al., in *Genetic Engineering, Vol.* 8 (Setlow and Hollaender, eds) pp. 277–298, Plenum, N.Y.). Transfected cells are grown until cells begin to lose their adherence to the culture plate surface, at which time the cells are harvested, collected by centrifugation, and lysed. The lysate is clarified by centrifugation to remove the cell wall debris, and the E1 containing lysate is applied to a sepharose-ubiquitin column (Hershko et al. (1983) *J. Biol. Chem.* 257:2537–2542) in the presence of ATP (e.g. 5 m MATP, 10 mM MgCl$_2$, and 0.2 mM clithiothreitol, 50 mM Tris-HCl (pH 7.2)). The column is washed several times with this buffer, and the E1 protein eluted with the following solutions: 1M KCl containing 50 mM Tris-HCl, pH7.2 (KCl eluate); the above Tris buffer, to remove salt; and finally 2 mM ATP and 0.04 mM sodium pyrophosphate in the above Tri buffer. The E1-containing eluate can be concentrated, as well as placed in new buffer solution, by centrifuge ultrafiltration with CentriPrep or Centricon membranes (Amicon Corp., Mass.). Alternatively, the ubiquitin-immobilized E1 can be used, as described below, in the purification of E2 enzymes.

ii) Human E2

A human rad6 homolog (SEG ID No. 15) was amplified from the HeLa cel cDNA using the primers 5'-(GC)$_3$AAGCTTATGTCGACCCCGGCCCGGAGGAGG-3' and 5'-(GC)$_3$GAATTCTTATGAATCATTCCAGCTTTGTTC-3' and cloned into pBluescript II pKS+ as a Hind III-EcoRI fragment. After further amplification, the pKS-E2 construct was cut with XhoI and NotI, and the fragment containing E2 coding sequence sub-cloned into a pGEX vector (Pharmacia catalog no. PGEX-4T-3) previously digested with SalI and NotI. The resulting pGEX-E2 construct encoded a glutathione-S-transferase (GST)/E2 fusion (Smith et al. (1988) *Gene* 67:31–40). The pGEX construct was introduced into *E. coli* by transformation, and the transformants grown in liquid media (LB) in the presence of IPTG. Purification of GST/E2 fusion protein was by standard protocols (*Current Protocols in Molecular Biology,* eds. Ausubel et al. (NY:John Wiley & Sons, 1991); Pharmacia instruction booklet (for catalog no. 27-4570)) using a glutathione-sepharose column (Pharmacia catalog no. 27-4570). Treatment with thrombin removed the GST domain from the fusion protein.

Alternatively, the rad6 coding sequence was excised from the pKS-rad6 construct as a HindIII-EcoRI fragment and ligated into pVL1393 cut with Sma I and Eco I. The E2 protein is produced in Sf9 cells, as described above, and purified on a sepharose-uibiquitin:E1 column. As above, a clarified lysate of the E2-producing insect cells, adjusted to 50 mM Tris-HCl (pH 7.2), 5 mM ATP, 10 mM MgCl$_2$, and 0.2 mM dithiothreitol, is applied to the ub:E1 column, washed, then eluted to remove any remaining ub:E1 (e.g. E2 will be exchanged for E1 on the column). Rad6 is then eluted from the column by washing with 50 mM Tris-HCl (pH 9.0) containing 2 mM dithiothreitol.

In similar fashion, recombinant forms of human UBC3/CDC34 (SEQ ID No. 19) were produced.

iii) HPV-18 E6

The coding-sequence for HPV-18 E6 (SEQ. ID No. 16) was amplified from the HeLa cell cDNA library using the primers 5'-(GC)$_3$AAGCTTATGGCGCGCTTTGAGGATCCAACA-3' and 5'-(GC)$_3$GAATTCTTATACTTGTGTTTCTCTGCGTCG-3', the PCR products purified, and the amplified E6 sequences digested with Hind III and EcoRI and ligated into a pBlueScript II pKS+ phagemid. Several different expression vectors were generated by subcloning the E6 sequences from the pKS-E6 construct. For example, a Hind III to EcoRI fragment containing E6 coding sequences was ligated into pVL1393 cut with SmaI and EcoRI to produce baculovirus expression system as described above.

Alternatively, E6 has been generated as His$_6$ fusion protein for purification on a Ni$^{2+}$ metal column. An XhoI to EcoRI fragment of the pKS construct was cloned into the pBlueBac A baculovirus (intvitrogen catalog no. V360-20) previously digested with XhoI and EcoRI. Following the manufacturer's protocols, the His$_6$-E6 fusion protein was expressed in Sf9 insect cells, and purified on a Ni$^{2+}$ charged sepharose resin (Invitrogen catalog no. R801; sell also Hochuli et al. (1987) *J. Chromatography* 411:177–184; and Janknecht et al. (1991) *PNAS* 88:8972–8976). Following purification of the fusion protein, the His$_6$ tag can be removed by treatment with entrokinase.

iv) Human E6-AP

E6-AP (SEQ ID No. 17) was cloned from the HeLa cell cDNA library using the PCR primers 5'-(GC)$_3$AAGCTTTCAGGACCTCAGTCTGACGAC-3' and 5'(GC)$_3$ GGATCCTTACAGCATGCCAAATCCTTTGGC-3', wherein the amplified E6-AP sequences were digested with Hind III and Bam HI and ligated into pBluescript II pkst. Constructs for expressing both HIS$_6$ tagged and GST tagged versions of E6-AP were generated. In one instance, an NheI to BamHI E6-AP containing fragment was cloned into pBlueBacA (cut with NheI and BamHI), and the construct expressed in insect cells. As above, the His-tagged E6-AP protein was purified by Ni$^{+2}$ affinity, and the his-tag subsequently removed by treatment with enterokinase.

Alternatively, a HindIII (fill) to NotI fragment has been isolated from the pKS-E6AP construct and subsequently ligated into the SmaI-Not I sites of pGEX-4T-3, to produce a GST fusion protein in *E. coli* which was purified using a gluathione-sepharose resin.

v) Human p53

Human p53 (SEQ ID No. 18) was cloned into pBluescript II pKS+ from the HeLa cell cDNA library using the primers 5'(GC)$_3$GAATTCGCCATGGAGGAGCCGCAGTCAGATCCT-3' and 5'-(GC)$_3$AAGCTT-TCAGTCTGAGTCAGGCCCTTCTGT-3'. In similar fashion to the other component proteins above, several different expression constructs were generated for p53, some of which included extra polypeptide sequence to facilitate purification. For expression in insect cells, two baculoviral constructs were made. For native p53, a BamHI fragment of the pKS-p53 vector was ligated into BamHI digested pVL1393. For His$_6$-tagged p53, the BamHI fragment was ligated into pBlueBacA previously cut with BamHI. Likewise, a GST-p53 was generated in *E. coli* by expression of a pGEX construct made by ligating a p53-containing EcoRI to NotI fragment of the pKS-p53 construct into pGEX-4T-1.

In the instance of each of the two fusion proteins, standard protocols were used to purify p53 from lysed transformants. For the native p53 produced by the pVL1393-p53 construct, the method of Hupp et al. was used to purify the p53 on a heparin-sepharose column (Hupp et al. (192) *Cell* 71:875–886).

vi) Ubiquitin

Ubiquitin is available from commercial sources (Bovine ubiquitin, Sigma catalog no. 6253; yeast ubiquitin, Sigma catalog no. 2129). Various modified forms of ubiquitin are also available as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS (N-hydroxysuccinimide ester) using well-known techniques (biotinylation kit; Pierce catalog no. 214206, 203188 (6 atom spacer), or 203114 (14 atom spacer)).

vii) Additional Reagents

For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtrite plates (Pierce catalog no. 15124); Maleic anhydride-activated polystyrene 96 well plates (Pierce catalog no. 15110); and antibody to human p53 (PharMingen catalog Nos. 14091A and 14211A).

EXAMPLE 3

In Vitro Ubiquitination of p53

We describe the cloning of a new human ubiquitin-conjugating enzyme hUbCE in Example 1. In Examples 4 and 5, we show that hUbCE specifically ubiquitinylates E6AP and is involved in the turnover of p53 in vivo. We have defined several discrete biochemical steps in the activation and transfer of ubiquitin onto p53. These biochemical reactions provide two levels of specificity in the ubiquitination of p53; the hUbCE dependent ubiquitination of E6AP, and the E6-dependent transfer of ubiquitin from ubiquitinylated E6AP to p53.

Proteins

To perform an in vitro ubiquitination reaction, native hUbCE and UBC2, the human homolog of the *S.cerevisiae* DNA repair gene, Rad6 (Koken et al. (1991) *PNAS* 88:8865–8869) were expressed and purified from *E.coli* BL21(DE3 ). Both proteins are readily soluble and easily purified using standard procedures. The cloning and purification of each of the proteins hUbCE, UBC2, p53, human E1, E6, and E6AP are described in Example 2 above. Briefly, native p53 was expressed from the baculoviral vector pVL1392 in Sf9 insect cells according to the manufacturer's instructions (Pharmingen) and purified on a p53 affinity column. HPV18 E6 was expressed *E. coli* BL21 as a GST fusion protein and purified on GSH-sepharose. Human E1 was cloned by PCR from the published cDNA sequence (Handley et al. (1991) *PNAS* 88:258–262), and native protein was expressed and purified from baculoviral infected cells. E6AP was expressed in *E.coli* JM109 as a GST fusion protein and purified on GSH-sepharose.

Ubiguitination reactions

Ubiquitination reactions contained 50–200 ng of the indicated proteins in 50 mM Tris pH 7.5, 5 mM MgCl$_2$, 2 mM ATP-γ-S, 0.1 mM DTT and 5 μM ubiquitin. Total reactions (30 μl) were incubated at 25° C. for 3 hrs and then loaded on an 8% SDS gel for analysis of p53 ubiquitination or a 4–20% gradient gel for analysis of ubiquitination of the ubiquitin-conjugating enzymes and E6AP. The gels were run and proteins were electrophoretically transferred to nitrocellulose. p53 proteins were revealed with the monoclonal antibody DO-1 (Oncogene Science) and the ECL system from NEN. Ubiquitinylated proteins were visualized using Extravidin-HRP from Sigma and the ECL system from NEN.

As demonstrated in FIG. 2, the appearance of specific p53-ubiquitin conjugates requires hUbCE, HPV18-E6, E6AP, ubiquitin and E1, the ubiquitin activating enzyme. In contrast, UBC2 was active in a minimal conjugation reaction containing E1, ATP and ubiquitin, in that E1 could activate ubiquitin and transfer it onto UBC2. However, UBC2 could not substitute for hUbCE in the p53 conjugation reaction (FIG. 2, lane 3). In addition, we made an active site cysteine-to-serine mutation in hUbCE. Such active site E2 mutants should accept activated ubiquitin from E1 but should not ubiquitinylate their downstream substrates owing to the high stability of the esther linkage formed between the active site serine and the carboxy-terminus of ubiquitin. This mutant was inactive in the p53 conjugation reaction (FIG. 6, lane 7). These results demonstrate that a catalytically active hUbCE is absolutely required for generation of ubiquitinylated p53 in this in vitro system.

Figure 3A:
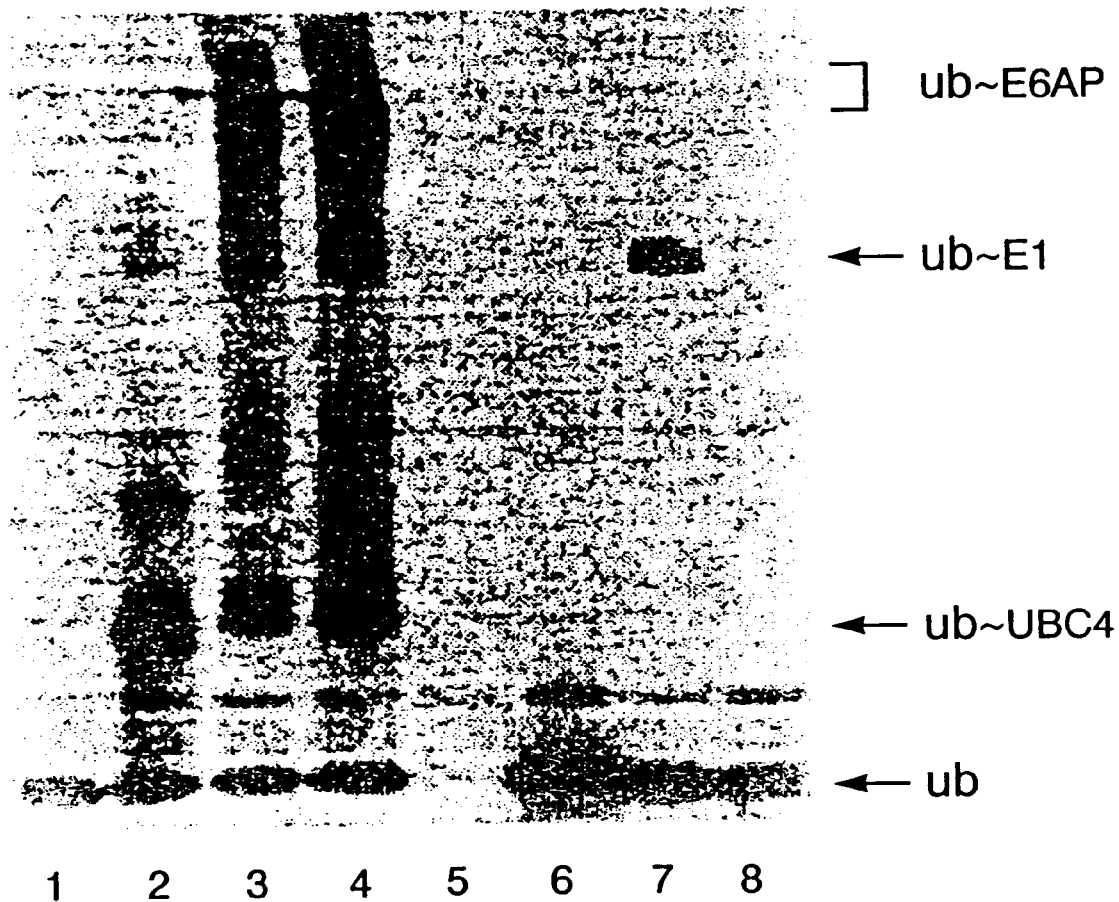
FIG. 3A shows the ubiquitination of E6AP. Purified proteins were used in ubiquitination reactions containing biotinylated ubiquitin. Lane 1 ubiquitin, lane 2 E1, ubiquitin and hUbCE, lane 3 E1, ubiquitin, hUbCE and E6AP, lane 4 E1, ubiquitin, hUbCE, E6AP and E6, lane 5 E1, hUbCE, E6AP and E6, lane 6 ubiquitin, hUbCE and E6AP, lane 7 E1, ubiquitin and E6AP, lane 8 ubiquitin and E6AP.

In FIG. 3A we show that ubiquitinated E1 could transfer ubiquitin efficiently to hUbCE but not directly to E6AP and that ubiquitinated hUbCE transferred ubiquitin to E6AP in a reaction that was not further stimulated by E6. All of these ubiquitination reactions required the presence of the ubiquitin-activating enzyme, E1, and ubiquitin.

Figure 3B:
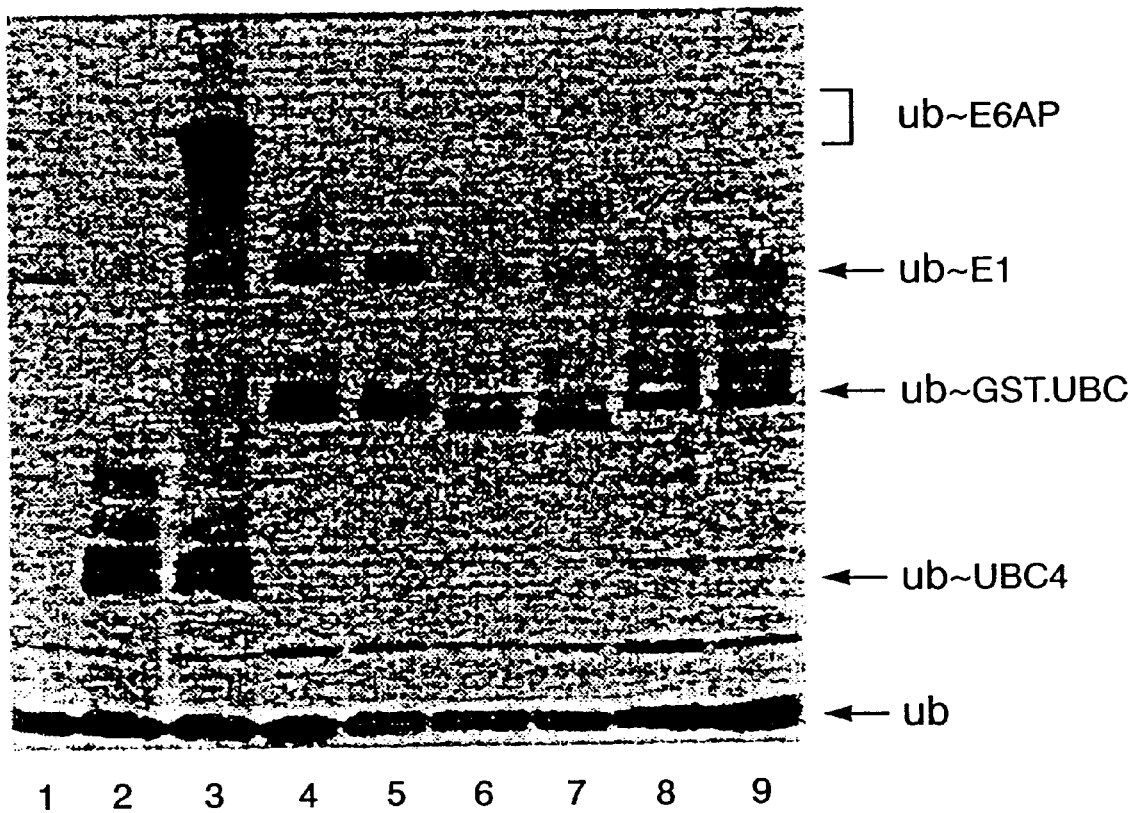
FIG. 3B demonstrates the hUbCE-specific ubiquitination of E6AP. All lanes contained E1 and ubiquitin with the following additions: lane 1 nothing, lane 2 hUbCE, lane 3 hUbCE and E6AP, lane 4 GST.UBC8, lane 5 GST.UBC8 and E6AP, lane 6 GST.UBC2, lane 7 GST.UBC2 and E6AP, lane 8 GST.epiUBC, lane 9 GST.epiUBC and E6AP.

To address the issue of the specificity of hUbCE-mediated ubiquitination of E6AP we performed ubiquitination reactions with purified recombinant hUbCE, GST-UBC2, GST-UBC8 (Kaiser et al. (1994) *J. Biol. Chem.* 269:8797–8802) and a GST-fusion of the so-called epidermal ubiquitin conjugating enzyme (Liu et al. (1992) *J Biol Chem* 267:15829–15835). Each of these recombinant proteins could accept activated ubiquitin from E1, but only hUbCE could donate ubiquitin to E6AP (FIG. 3B). We also confirmed that native UBC2 could accept ubiquitin from E1 but could not donate ubiquitin to E6AP (data not shown).

We then purified the ubiquitinated E6AP by affinity chromatography on glutathione-Sepharose and demonstrated that it did not contain appreciable amounts of ubiquitinated E1, ubiquitinylated hUbCE or free ubiquitin. We found that this purified, ubiquitinated E6AP could donate ubiquitin to p53 in an E6-dependent reaction.

EXAMPLE 4

Radiolabel-Detection Assay $^{35}$S-labeled p53, prepared by cell culture technique utilizing $^{35}$S-methionine, is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin-coated microtitre plate and incubated to capture the complex of biotinylated ubiquitin and p53 (free biotinylated ubiquitin will also compete for binding sites on the well). The wells are washed with buffer (e.g. phosphate-buffered saline, or conjugation buffer lacking ubiquitin and ATP) to remove uncomplexed p53. Ubiquinated p53 is detected by addition of scintillant to the well and counting in a scintillation instrument. Inhibition of the ubiquitin conjugation system by an added candidate agent is indicated by a reduced radioactive count

EXAMPLE 5

Immunodetection Assay p53 is incubated with combined purified components of a ubiquitin conjugating system as described above, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and p53 (free biotinylated ubiquitin will also compete for binding sites on the well). The wells are washed with buffer to remove uncomplexed p53. Next, the ub:p53 complexes capatured on the plate are decorated with a murine monoclonal antibody to p53. The wells are washed and binding of monoclonal antibody is detected by addition of peroxidase-conjugated antibody to mouse IgG (H+L) (Pierce catalog nos. 91430G and 91450G) and contacting with an appropriate substrate system, such as o-phenylenediamine dihydrochloride (Sigma catalog no. P9187).

EXAMPLE 6

GST Detection Assay

The GST-p53 fusion product is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and GST-p53 (free biotinylated ubiquitin will also compete for binding sites on the well). The wells are washed with buffer to remove uncomplexed GST-p53. Binding of ubiquitinated GST-p53 is monitored with a detection system, based either on a biochemical assay for GST (e.g., 1-chloro-2,4-dinitrobenzene, Pharmacia catalog no. 27-4590-01) or an immunological assay using goat anti-GST antibody (Pharmacia catalog no. 27-4590-01).

EXAMPLE 7

Reporter Construct Detection Assay

Figure 5:
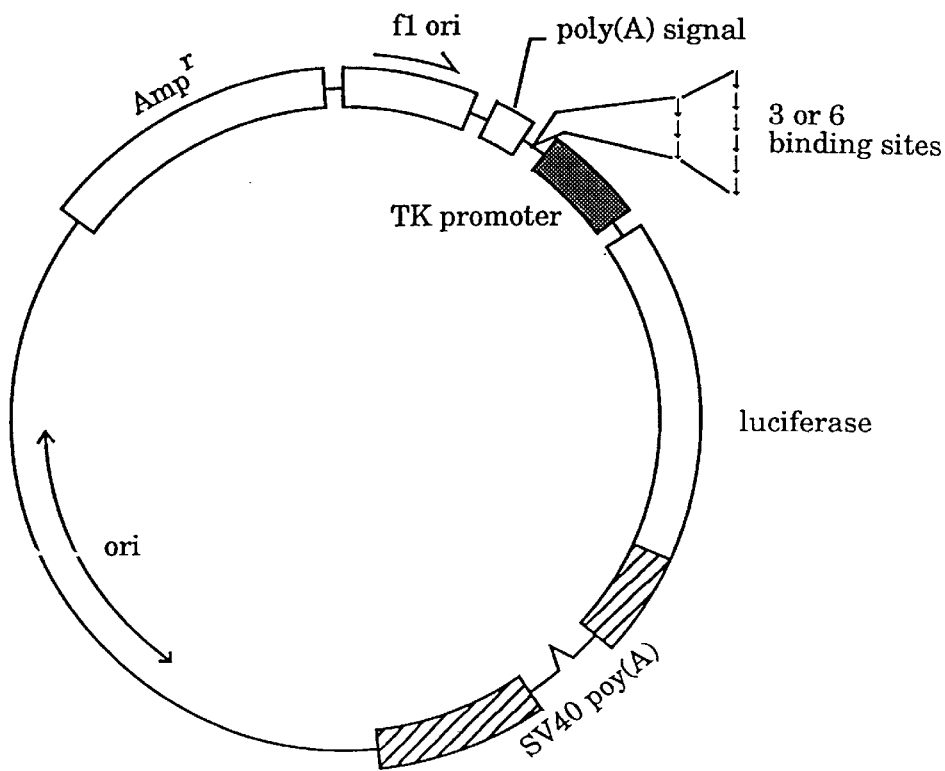
FIG. 5 depicts am exemplary luciferase reporter construct derived from the pGL2-Basic vector (Promega catalog no. E1641) by addition, in the multiple cloning region, of a SalI to BamHI fragment containing the TK promoter sequence with either 3 or 6 tandemly arranged binding sites (either p53, myc or sP1 binding sites) placed upstream of the TK promoter.

The plasmid pTKluc, shown in FIG. 5, comprises a luciferase gene whose expression is driven by the core Herpes simplex virus thymidine-kinase (TK) promoter which has been modified with either p53 (p53RE/TK), myc (mycRE/TK), or Sp1 (Sp1 RE/TK) binding sites. When the construct lacking any of the modifications to the TK promoter is transfected into mammalian cells, the detectable luciferase activity is low because this core TK promoter fragment does not contain the upstream activating sequences necessary for efficient transcriptional activation of the luciferase gene. However transfection with the constructs in which TK is further modified to contain either 3 or 6 response-elements (RE) for one of p53, myc or Sp1, the detectable luciferase activity increases in cells which express the appropriate protein. For example, the level of luciferase expression is significantly higher in p53-producing cells (e.g. ML1 cells) transfected with the p53 RETK-containing construct than with the TK construct. Likewise, endogenous myc and Sp1 proteins can drive expression of the mycRE/TK and Sp1RE/TK constructs. As set out above, both p53 and myc can be degraded by the ubiquitin pathway. However, Sp1 is not known to be degraded by any ubiquitin-mediated pathway, and the SP1RE/TK construct can therefore be used as a control in the present assays. Thus, in the presence of an agent which inhibits ubiquitin-mediated degradation of p53 in a cell harboring the p53 RE/TK construct, the level of luciferase activity would increase relative to that in the cell not treated with the candidate agent.

To construct the luciferase reporter constructs shown in FIG. 5, the pGL2-Basic vector (Promega catalog no. E1641) was modified by addition, in the multiple cloning region, of a SalI to BamHI fragment containing the TK promoter sequence with either 3 or 6 tandemly arranged binding sites placed upstream of the TK promoter. Prior to addition of the RE/TK promoter sequences, a SalI restriction site at 2744 of pGL2-Basic was destroyed by oligonucleotide site-directed mutagenesis. The resulting constructs, designated p53RE/TK, mycRE/TK, and Sp1RE/TK, were each subsequently used to transfect mammalian cells following the manufacturer's suggests (Technical notes, Part #TM003 of Promega Catalog no. E164).

In an alternative embodiment, a SalI to BamHI fragment of p53/RE/TK containing the luciferase reporter gene was isolated and sub-cloned into another eukaryotic expression vector pcDNAIII (Invitrogen, San Diego, Calif.) previously digested with BglII and XhoI.

The vector p53RE/TK is transfected into the human chronic leukemia cell line ML1 that expresses wild-type p53. In this in vivo situation, luciferase expression is upregulated by the presence of p53, which functions as a transcriptional activating factor by binding to the p53 response element upstream of the TK promoter. The ubiquitin conjugating system participates in the degradation of p53 and, when functional, down regulates the expression of luciferase in this system. Measurement of luciferase activity are carried out by standard protocols (see, for example, Promega Technical Bulletin #TB161). Cells are grown and transfected in a tissue culture grade 96 well microtitre plate. The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay sustrate (Beetle luciferin, Promega catalog no. E1603) is added, and the reaction in each well monitored in a luminometer or scintillation counter. Inhibition of the ubiquitin conjugating system results in a greater luminescence signal than the uninhibited system. Although an in vivo assay, this screen will ignore general cytotoxic compounds.

EXAMPLE 8

Microinjection of Sense and Anti-Sense Constructs of the hUbCE Gene

To investige the consequences of interfering with hUbCE and E6AP function in p53 degradation, we performed microinjection experiments using sense and anti-sense constructs of the hUbCE gene. To facilitate the detection of p53 by indirect immunofluorescence, the experiments were performed in the human tumor cell line MDA-MB-468 which contain high levels of mutant p53 (Arg273His). In this line, the degradation of p53 could be stimulated by microinjection of an HPV-18 E6 expression plasmid.

Figure 4:
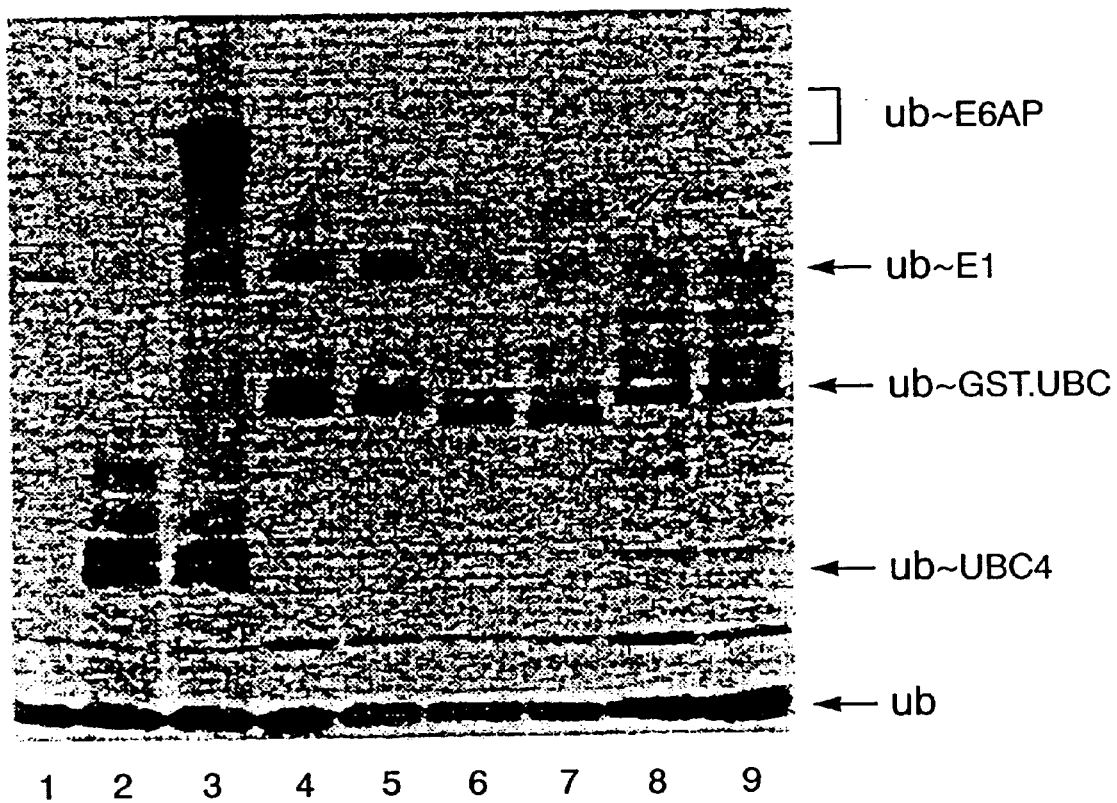
FIG. 4 shows the degree of inhibition of E6 stimulated p53 degradation in co-injection experiments. The indicated DNAs were co-injected with pX.E6. The levels of inhibition of the E6 stimulated p53 degradation are derived from an analysis of approx. 150 injected cells per experimental point in at least two independent experiments.

In order to determine whether hUbCE and E6AP mediate the E6-dependent ubiquitination and degradation of p53 in vivo co-injection experiments were performed. To briefly describe the experiments, the CMV expression vectors were obtained by inserting the entire open-reading frame of one of HPV-18 E6, human E1, human E6-AP, hUbCE, or a Cys-85 mutant of hUbCE, in either a sense or anti-sense orientation (as indicated in FIG. 4) in the pX-plasmid (Baldin et al. (1993) *Genes & Devel.*, 7:812–821). Plasmids were purified with a Promega Wizard Maxi-prep kit and injected at a concentration of 50 to 100 µg/µl in the presence of normal affinity-purified rabbit or mouse antibody (5 mg/ml in PBS) used as microinjection marker.

Cell monolayers of asynchronous MDA-MB-468 cells were injected with the indicated DNAs (FIG. 4) along with rabbit IgG to allow identification of injected cells with an automated microinjection system (AIS, Zeiss; Ansorge et al. (1988) *J. Biochem. Biophys. Meth.*, 16:283–292). All microinjection experiments were carried out in 3.5 cm Petri dishes containing 3 ml of DMEM medium carbonate free, in order to avoid the decrease in pH of the medium during the injection. Each cell was injected at a pressure between 50 and 150 hPa. After 24 hrs the cells were fixed and stained with a p53 specific monoclonal antibody (DO-1; Oncogene Sciences) followed by a biotinylated horse anti-rabbit antibody and Texas red conjugated streptavidin. Injected cells were identified by staining with an FITC conjugated goat anti-rabbit antibody (Baldin et al. (1993) *Genes and Dev* 7:812–821).

When either an anti-sense or mutant hUbCE expression plasmid or an expression plasmid encoding anti-sense E6AP was co-injected with the E6 expression plasmid, the E6 stimulated degradation of p53 was inhibited (FIG. 4). Similar results were obtained when polyclonal antibodies generated against human hUbCE or an expression plasmid encoding a mutant form of E6AP were microinjected (not shown).

Co-injection of an E6 expression plasmid with an expression plasmid encoding anti-sense E1 also inhibited the E6 stimulated degradation of p53. Co-injection of anti-sense or mutant UBC2 expression plasmids had a negligible effect on the E6 stimulated degradation of p53 (FIG. 4).

Moreover, the data that an hUbCE mutant, Cys-85→Ser, which produces an inactive form of the enzyme, is possibly a dominant negative mutant able to at least partially rescue p53.

EXAMPLE 9

Cloning of Yeast UbCE Genes

In order to clone homologs of the hUbCE gene, degenerate oligonucleotides based on the conserved regions PVGDDLFHWH/Q and ITLAPSW (see SEQ ID No. 1) were designed and used to amplify *S. pombe* genomic DNA and cDNA in λZAP (strain h+$^N$his3–) and *C. albicans* genomic and cDNA in λZAP (strain 3153A). The amplification consisted of 30 cycles of 94° C. for 1 minute, 55° C. for 1 minute and 72° C. for 1 minute. The PCR reactions were separated on a 2.5% low melting agarose gel, that identified a 250 bp fragment for both genomic and complementary DNA from *C. albicans*. From *S. pombe* 250 and 650 bp fragments were detected for complementary and genomic DNA respectively. The size discrepancy between complementary DNA and genomic *S. pombe* DNA fragments probably reflects the presence of an intron. The fragments of 250 bps were eluted and cloned into pCRII (TA cloning system, Invitrogen corporation).

The *S. pombe* and *C. albicans* DNA probes were $^{32}$P labeled by nick translation and used on Southern blots to confirm the species identity of the fragments and to screen *S. pombe* and *C. albicans* cDNA libraries. Sequencing of the full length cDNAs confirmed the identity of the clones. The *C. albicans* and *S. pombe* UbCE open-reading frames are both 147 aa residues long (SEQ ID Nos: 3 and 5, respectively). The newly isolated genes are named caUbCE and spUbCE for *C. albicans* and *S. pombe* respectively.

EXAMPLE 10

Cloning of the Human rapUBC Enzyme

Utilizing a two hybrid assay comprising an FKBP12-bait protein, a drug-dependent interaction trap assay was used to screen a WI38 (mixed $G_0$ and dividing fibroblast) cDNA library (Clonetech, Palo Alto Calif.) in pGADGH (XhoI insert, Clonetech). Briefly, the two hybrid assay was carried out in an HF7C yeast cell (Clonetech) in which FKB1 gene was disrupted. Of the clones isolated, a novel human ubiquitin-conjugating enzyme (rap-UBC, SEQ ID Nos. 12 and 13) has been identified. The original clones contained 5' end of the gene which included substantial portion of the coding region for rapUBC, including the active site cysteine and the 3' end of the gene. In order to obtain full length sequence of the rapUBC gene, the 5' end was cloned using a library vector (MTXP37) and oligos corresponding to sequences near the 5' end of the original cDNA clone SMR4-15. The oligos used were: VB1040: CTACTAATAG-GTAGAAGCGGTGG (SEQ ID No:20) and VB1041: GGTAAACCAAAGCCCGACAGGG (SEQ ID No:21). PCR products were obtained from a cDNA library made from normal human fibroblasts (dividing WI38 cells).

EXAMPLE 11

Ubiquitination of p27 by UBC3

The protein p27 is a potent inhibitor of cyclin-dependent kinases and its overexpression in mammalian cells causes a G1 arrest. In serum deprived cells p27 accumulates without an increase in mRNA or protein synthesis indicating that the regulation of its abundance occurs at the level of protein stability. We demonstrate here that p27 is degraded in vivo and in vitro through the ubiquitin-proteasome pathway. In human MG-63 cells, inhibition of the proteasome using the peptide-aldehyde, LLnL, induced an accumulation of p27 protein, but not p21, a distinct cdk inhibitor. Because of lack of proteasome activity, accumulation of ubiquitinated forms of p27 was observed. We also found that p27 was ubiquitinated and degraded in an ATP dependent manner in a rabbit reticulocyte lysate (RRL) system. Inhibition or depletion of the proteasome blocked p27 degradation in vitro. Addition of purified human Ubc2 or Ubc3 enzymes, but not of four other different human Ubcs to RRL, induced an increase in p27 turnover. Consistent with these results, inhibition of Ubc2 or Ubc3, using inactive mutant proteins, specifically slowed the kinetics of p27 proteolysis. These results represent the first demonstration that the ubiquitin-proteasome pathway plays a role in the regulation of a cell cycle protein in human cells, namely the cdk inhibitor p27. This specific proteolysis of p27 may, therefore, represent a novel mechanism for regulating cyclin dependent kinases.

Immunoreagents

Anti-p27 polyclonal antibody (F-L) was generated against mouse bacterial expressed purified p27 -his6. Characterization of this antibody is reported elsewhere (S.W.T. and M.P., manuscript in preparation). The monoclonal antibody to p27 was from Transduction Laboratories (#K25020) and the C-T polyclonal antiserum generated against a synthetic peptide (19 amino acids) carboxyl terminus was from Santa Cruz Biotechnology (#sc-528). The preparation and characterization of the rabbit polyclonal antiserum against human p21 and of 4F3 monoclonal antibody to ubiquitin have been described previously in the art.

Cell culture and cell synchronization

The human osteosarcoma cell line MG-63 was obtained from the American Type Culture Collection (ATCC) and cultured in Dulbecco's-Modified Eagle's Medium (DMEM). Cells were synchronized in G1. In brief, cells were incubated 2–3 days in DMEM containing 0.2% fetal calf serum (FCS). After these periods of incubation, more than 95% of the cells presented a 2N DNA content. Cell cycle phases were monitored by flow cytometry (FACSCAN, Becton Dickinson) and by BrdU incorporation (see Immunofluorescence paragraph).

Electroporation

Cells were electroporated. In brief, cell monolayers growing on glass coverslips (at ca. 60% density) were trypsinized and about $3\times10^6$ cells were incubated at 37° C. in suspension with 1 ml DMEM supplemented with 10% FCS and LLnL or E64 peptide at a concentration of 50 μM. After one hour, cells were washed twice with PBS, resuspended in 100 μl of cold PBS containing 1 μg/ml of either peptide and left on ice for 10 minutes. After this time, cells were transferred to a precooled cuvette (Bio-Rad, 0.4 cm electrode distance) and electroporated using a Bio-Rad GenePulser electroporator (200v,125 μF, infinite resistance). After electroporation, cells were incubated again on ice for five minutes and then immediately reincubated at 37° C. in prewarmed DMEM supplemented with 10% FCS and LLnL or E64 peptide for 1–2 additional hours.

Extract preparation, Immunoblotting and Immunoprecipitation

Cell extracts were prepared as previously described in the literature, with the following modifications. Three to 5 volumes of lysis buffer (50 mM Tris-HCl, pH 7.4, 0.25 M NaCl, 1% Triton-X100, 0.1% SDS, 0.5% deoxycholate, 1 mM EDTA, 50 mM NaF, 0.1 mM $Na_3VO_4$) were added to pelletted cells. The following protease inhibitors were added: 0.1 mM phenyl-methyl sulfonyl fluoride (PMSF), 1 μg/ml of leupeptin, 10 μg/ml of soybean trypsin inhibitor, 10 μg/ml of L-1 Chlor-3-(4-tosylamido)-4 Phenyl-2-butanon (TPCK), 10 μg/ml of L-1 Chlor-3-(4-tosylamido)-7-amino-2-heptanon-hydrochloride (TLCK), 1 μg/ml of aprotinin, 10 mM N-ethylmaleimide (NEM). After incubation on ice for 30 minutes, the samples were centrifuged at 14,000 rpm in an Eppendorf microfage for 5 minutes at 4° C. to recover the supernatant. Proteins were transferred from gel to a nitrocellulose membrane (Novex) by wet blotting. Filters were subjected to immunoblotting using the ECL (NEN) detection system according to the manufacturer's instructions. For immunodetection with anti-Ubiquitin antibody, in order to completely denature the ubiquitin-containing proteins, filters were immersed in distilled water and autoclaved using a sterilization program for 15 minutes before processing. Immunoprecipitation were performed as described in [Tam, 1994 #2163].

Northern blot analysis

RNA was isolated from exponentially growing cells using standard Chomczynski extraction methods. Northern analysis was performed. Briefly, total RNA was separated by 1% agarose denaturing gel electrophoresis, transferred to Nytran-Plus nylon membranes, and hybridized with probes which were radiolabeled with $[\alpha^{32}P]dCTP$ (Amersham, Inc.) using a random primer DNA labeling kit (Boehringer, Inc.) and used for hybridization at $1\times10^6$ cpm/ml. Washing conditions were done to a final stringency of 0.1×SSC, 0.1% SDS, at 65° C.

Immunofluorescence

Indirect immunofluorescence was performed as generally described in the art, with the following modifications. Cell monolayers growing on glass coverslips were rinsed in PBS and fixed for 10 minutes in 4% formaldehyde (Sigma, HT50-1-1). Fixed cells were permeabilized with 0.25% Triton X-100 and processed for cell staining. Incubation with primary antibodies (anti-p27 monoclonal antibody; 10 μg/ml) was carried out for one hour in a humidified chamber. After three washes in PBS the coverslips were incubated for 30 minutes with biotinylated horse anti-mouse secondary antibody (Vector Laboratories, dilution 1:50). Cells were washed again three times with PBS and incubated with Texas red-conjugated streptavidin (Vector Laboratories, dilution 1:100) or FITC-conjugated streptavidin (Vector Laboratories, dilution 1:50). All reactions were carried out at room-temperature and antibody dilutions were made in DMEM containing 10% FCS. Counterstaining for DNA was performed by adding 1 μg/ml bisbenzimide (Hoechst 33258) into the final PBS wash. Immunofluorescence samples were directly mounted in Crystal/mount medium (Biomeda Corp.). Photographs were taken using a Plan-Neofluar 100× or a Plan-Neofluar 40× lens mounted on a Zeiss Axiophot Photomicroscope and a Color Video Printer Mavigraph, on Sony UPC-3010 print paper.

Protein expression and purification p27-his6, Ubc3-his6 and mutant Ubc3-his6 were bacterially expressed and purified by Ni-NTA-agarose (Invitrogen) according to the manufacturer's instructions. Native Ubc2 and native hUbCE (bacterially expressed) and E1 proteins (from baculovirus infected cells) were purified as described above. GST-Ubc2 mutant, GST-hUbCE mutant, GST-Ubc8, GST-rapUBC and GST-Ubcepi were bacterially expressed and purified by GH-Sepharose (Pharmacia) according to the manufacturer's instructions.

In vitro Ubiquitination and degradation of p27 p27-$his_6$ was incubated at 37° C. for different times in 30 μl of degradation mix [final concentration 33% (v/v) untreated reticulocyte lysate (Promega), 50 mM Tris-HCl (pH 8.3), 5 mM $MgCl_2$, 5 mM $CaCl_2$, 2 mM DTT], in presence or in absence of 3.5 mM ATP-γ-S and in presence or in absence of purified bacterially expressed Ubc enzymes. All purified protein were used in the degradation mix at ~1 μM concentration. The reaction was stopped by addition of Laemmli sample buffer followed by immediate freezing of the samples in liquid nitrogen. Ubiquitinated p27 and p27 degradation was analyzed by electrophoresis and immunoblot with monoclonal anti-p27 antibody. In some cases, ubiquitinated p27 was detected by adding 5 μM biotinylated ubiquitin to the degradation mix. After the reaction was stopped, p27 was purified by either Ni-NTA-agarose or F-L anti-p27 antibody, electrophoresed, transferred on a nitrocellulose membrane (Novex) and visualized using HRP-conjugated streptavidin (Extravidin, Sigma) and the ECL (NEN) detection system according to the manufacturer's instructions. In some experiments, to remove the proteasome, the RRL was ultracentrifuged at 100,000 g for six hours in the presence of 5 mM $MgCl_2$. In others, ATP was depleted from RRL by treatment (20 minutes at 30° C.) with apyrase [5 units/ml in 50 mM Tris-HCl (pH 8.0), 4 mM $CaCl_2$, 0.05% BSA)].

Ubiquitination in purified in vitro system

Purified protein were incubated at 37° C. for 30 minutes in 30 μl of ubiquitination mix [50 mM Tris-HCl (pH 8.3), 5 mM $MgCl_2$, 5 mM $CaCl_2$, 1 mM DTT, 2 mM ATP-γ-S, 5 μM biotinylated ubiquitin]. All purified protein were used in the ubiquitination mix at ~1 μM concentration. The reaction was stopped by addition of Laemmli sample buffer followed by immediate freezing of the samples in liquid nitrogen. Samples were electrophoresed, transferred on a nitrocellulose membrane (Novex) and visualized using either HRP-conjugated streptavidin (Extravidin, Sigma) or anti-p27 monoclonal antibody and the ECL (NEN) detection system according to the manufacturer's instructions.

p27 protein accumulation in serum starved human osteosarcoma cells, without increases in mRNA and protein synthesis We analyzed the levels of p27 and p21 protein and mRNA in serum deprived human MG-63 cells. We found that 48–72 hours after serum starvation, when 95% of the cells showed a 2n DNA content by flow cytometry, the p27 protein level was strongly induced compared to proliferating cells. In contrast, the p21 levels remained constant. Interestingly, the mRNA levels for both p27 and p21 were found to be comparable in asynchronously growing cells and in G1 cells. Similar results were obtained with normal human fibroblasts. We also analyzed whether the cellular abundance of p27 and p21 varied after serum readdition. Arrested cells were stimulated to reenter the cell cycle and monitored for a period of 18 hours. Cells started to synthesize DNA, as monitored by flow cytometry, approximately 12 hours after serum addition. By 18 hours about 80% of the cells had incorporated 5-bromo deoxyuridine (BrdU) (data not shown) and show a DNA content higher than 2N. At different time points cell lysates were analyzed by immunoblotting with antibodies to p27 and p21. The overall abundance of p27 protein gradually decreased after serum readdition, and by 18 hours reached a level similar to that found in asynchronous cells. In contrast, the p21 level initially increased after serum stimulation, then decreased by 9 hours, and by 18 hours reached a level comparable to that present in asynchronous cells.

The increase in p27 abundance in quiescent cells could be regulated by either an increase in the rate of protein synthesis or by a decrease in the rate of protein turnover, or by both. Metabolic labeling revealed that the rate of p27 synthesis was similar in both proliferating and serum deprived cells. These results suggest that levels of p27 protein are regulated at the level of protein turnover.

Accumulation of p27 and ubiquitinated forms of p27, but not of p21, upon proteasome inhibition in vivo The above results prompted us to test whether the intracellular regulation of p27 abundance involved the ubiquitin-proteasome pathway. We examined the effect of a peptide-aldehyde, LLnL (N-acetyl-leucinyl-leucinyl-norleucinal-H), a potent inhibitor of the chymotryptic site on the proteasome, on p27 levels. As a control, we used the cysteine protease inhibitor E64 (L-transepoxysuccinic acid) or vehicle (dimethyl sulfoxyde, DMSO) alone. MG-63 cells were treated for the various times with these compounds, then collected by trypsinization, washed with PBS and lysed as described in above. Cell lysates were electrophoresed, transferred to a nitrocellulose membrane and immunoblotted with either an anti-p27 monoclonal antibody or an anti-p27 carboxy terminus antiserum (C-T) or with a polyclonal antibody to p21. Addition of LLnL, but not of E64 or DMSO, induced an accumulation of p27 protein after 60 minutes of treatment. In contrast, p21 was not found to accumulate in LLnL treated cells. Interestingly, at later points, we noticed that the two anti-p27 antibodies, which do not recognize the same epitope, both recognized a doublet of approximately Mr 70,000. The monoclonal antibody also recognized an approximately Mr 100,000 band in the extract from the 24-hour LLnL time point. We reasoned that, since the proteasome is essential for the degradation of proteins covalently conjugated to ubiquitin, presumably these slower migrating bands represented ubiquitinated forms of p27 that accumulated in LLnL treated cells. To determine whether these bands contained ubiquitinated p27, lysates from cells treated for 24 hours with LLnL were subjected to immunoprecipitation with either an anti-p27 full-length antiserum (F-L) or with normal rabbit immunoglobulin and then immunoblotted with a monoclonal antibody to ubiquitin. The 70K doublet and a group of bands migrating as a high molecular weight smear were detected by anti-ubiquitin antibody exclusively in the anti-p27 immunoprecipitates. Immunoblot with a control antibody of similar immunoprecipitates did not visualize any band. When LLnL was introduced into cells by electroporation, the accumulation of p27 and the ubiquitinated forms of p27 was evident after two hours treatment (one hour before and one hour after electroporation). In contrast, introduction of E64 or DMSO alone by electroporation did not lead to an increase in p27 abundance. Again, p21 levels were unchanged by electroporation of either LLnL or E64.

We also used indirect immunofluorescence to analyze the subcellular localization of p27 after LLnL treatment. p27 was detectable in the nucleus of about 50–60% of serum starved cells. Twelve hours after serum readdition, nuclear p27 staining was reduced to less than 2%. E64 or DMSO did not affect the serum-stimulated p27 turnover. In contrast, after 6 hours or 12 hours in the presence of serum and LLnL, a bright nuclear p27 staining was detected in approximately 78% of the cells.

These results show that inhibition of the proteasome in intact cells leads to p27 accumulation and to the appearance of ubiquitinated forms of p27.

p27 is ubiquitinated and degraded in rabbit reticulocyte lysate

We tested whether purified bacterial expressed hexahistidine-tagged p27 (p27 -his6) was an in vitro substrate for ubiquitination in a rabbit reticulocyte lysate (RRL) system, an established source of ubiquitinating enzymes and proteasome complexes. Incubation of $p^{27}$-his6 with RRL for one minute, produced a ladder of bands higher than 27,000 as visualized by immunoblotting with a monoclonal antibody anti-p27. The ladder of bands was not detected if RRL was omitted from the reaction. Furthermore, no bands were recognized by the anti-p27 antibody when only RRL was present in the reaction, thus demonstrating that the bands recognized by the anti-p27 antibody are due to the presence of p27 -his6 and not to a crossreactivity with proteins present in the RRL. Time course experiments showed that after three hours, the overall intensity of the bands produced by the incubation of p27 -his6 with RRL decreases. After six hours of incubation, the p27 band was dramatically reduced and the ladder of bands had almost totally disappeared, suggesting that the RRL contained an activity able to degrade p27.

The degradation of p27 appeared to require ATP hydrolysis. Since RRL contains ATP, the addition of exogenous ATP did not change the kinetics of the reaction. In contrast, preincubation of RRL with apyrase, which hydrolyzes ATP, prevented the appearance of the slower migrating bands and inhibited the proteolysis of p27. ATP-γ-S, a non-hydrolysable ATP analog, when added to the degradation mix, led to a substantial reduction in the kinetics of proteolysis of p27.

To demonstrate that the ladder of bands obtained in these reactions was due to ubiquitination of p27, we added biotinylated-ubiquitin to the degradation mix and, after the reaction was terminated, we re-purified p27 -his6 with either an antibody to p27 or with Nickel-chromatography on nitriolotriacetic acid-agarose (Ni-NTA-agarose). The purified material was analyzed by SDS-polyacrylamide gel electrophoresis (PAGE) followed by transfer to a nitrocellulose membrane. Ubiquitinated proteins were visualized using streptavidin-HRP. Two major ubiquitin cross-reactive groups of bands co-migrated with the two groups of higher molecular weight bands identified by the anti-p27 antibody and were not detected in identical samples lacking biotinylated-ubiquitin or p27 in the degradation mix. This result demonstrates that the higher molecular weight bands obtained in the reaction are ubiquitinated forms of p27.

To demonstrate that the in vitro degradation of p27 required the proteasome, we added either 50 μM LLnL or 50 μM E64 or DMSO to the degradation mix. LLnL, but not E64 or DMSO, strongly inhibited p27 degradation). As described in other systems, LLnL had a lesser inhibitory effect in vitro compared to the effect observed in vivo. Two other protease inhibitors, the serine protease inhibitor, L-1 Chlor-3-(4-tosylamido)-7-amino-2-heptanon-hydrochloride (TLCK), used at 150 μM, or the cystein protease inhibitor, N-ethylmaleimide (NEM), used at 50 μM, did not inhibit p27 degradation. It has been previously shown that ultracentrifugation can deplete an extract of proteasome particles. We subjected the RRL to centrifugation at 100,000 g for 6 hours. Incubation of p27 with proteasome-depleted supernatant did not result in p27 degradation. Interestingly, when the proteasome-rich pellet was added back to the supernatant, p27 degradation was completely restored.

Ubc3 and Ubc2 specifically accelerate the turnover of p27 in rabbit reticulocyte lysate We tested whether the addition of human purified bacterially expressed ubiquitin-conjugating enzymes (UBCs) to the RRL altered the kinetics of the reaction. We tested Ubc2 (Rad6), Ubc3 (Cdc34), hUbCE, Ubc8, an epidermal Ubc (Ubc-epi) and rapUBC. We also tested the addition of HPV-18 E6 which increases the rate of p53 degradation in a similar assay. In all reactions ATP-γ-S was used to slow down the kinetics of reaction in order to highlight any potential difference. While Ubc2 and Ubc3 increased the rate of p27 turnover, the other proteins had no effect compared to the control. This difference was not due to a difference in their ability to accept ubiquitin from E1, because all of the Ubcs were efficiently charged in reactions containing purified recombinant human E1, the ubiquitin-activating enzyme. Interestingly, incubation with Ubc3 specifically produced a smear of bands of high molecular weight. Incubation of purified p27 with purified Ubc2 or Ubc3 generated a mono-ubiquitinated form of p27. This reaction was ATP, Ubiquitin and E1 dependent. The fact that the efficiency of this reaction was not very high and that only a single ubiquitin molecule was added to p27, strongly suggests that efficient multi-ubiquitination of p27 requires one or more factors which can be provided by the RRL.

Inhibition of Ubc2 and Ubc3 slows down the turnover of p27 in rabbit reticulocyte lysate The result that Ubc2 and Ubc3 accelerate the turnover of p27 in vitro, prompted us to test the effect of inhibition of these Ubc functions in vitro. We made active site cysteine-to-serine mutations in human Ubc3, Ubc2 and hUbCE (on cysteine 93, 88 and 85, respectively). The Ubc3 mutant also contained a leucine97-to-serine mutation which has been shown to increase the dominant negative effect of yeast Cdc34. Such active site E2 mutants are unable to accept activated ubiquitin from E1 and therefore should not ubiquitinate their downstream substrates. In addition, they efficiently inhibit the ubiquitination of their respective wild type in an in vitro reaction. In all reactions ATP-γ-S was used to slow down the kinetics of the reaction. Compared to a control reaction, addition of the Ubc3 mutant considerably slowed down the in vitro turnover of p27, while the Ubc2 mutant had a less pronounced effect. Addition of both Ubc2 and Ubc3 mutant proteins had the same effect as the Ubc3 mutant protein alone. Finally, the hUbCE mutant had no effect on p27 turnover.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An assay for identifying an inhibitor of ubiquitin-mediated proteolysis of a cell-cycle regulatory protein, comprising:
    (i) providing a eukaryotic cell engineered to express a recombinant ubiquitin conjugating enzyme encoded by a nucleic acid which hybridizes under high stringency conditions to a nucleic acid sequence of SEQ ID Nos.: 1, 3, or 5, wherein said cell also expresses a regulatory protein and ubiquitin;
    (ii) contacting the eukaryotic cell with a candidate agent;
    (iii) measuring a level of ubiquitination of the regulatory protein in the presence of the candidate agent; and
    (iv) comparing the measured level of ubiquitination in the presence of the candidate agent with a level of ubiquitination of the regulatory protein in the absence of the candidate agent,
wherein a decrease in ubiquitination of the regulatory protein in the presence of the candidate agent is indicative of an inhibitor of ubiquitination of the regulatory protein.

2. The assay of claim 1, wherein the regulatory protein is selected from a group consisting of p53, p27$^{kip1}$, myc, MATα2, a cyclin, and fos.

3. The assay of claim 1, wherein the eukaryotic cell expresses a recombinant E3 ubiquitin-ligase protein.

4. The assay of claim 1, wherein at least one of the ubiquitin or the regulatory protein comprises a detectable label, and the level of ubiquitin-conjugated regulatory protein is quantified by detecting the label in at least one of the regulatory protein, the ubiquitin, and the ubiquitin-conjugated regulatory protein.

5. The method of claim 4, wherein the label is selected from the group consisting of radioisotopes, fluorescent compounds, enzymes, and enzyme co-factors.

6. The assay of claim 4, wherein the detectable label is a protein having a measurable activity, and the regulatory protein is fusion protein including the detectable label.

7. The assay of claim 1, wherein the amount of ubiquitin-conjugated regulatory protein is quantified by an immunoassay.

8. An assay for identifying an inhibitor of ubiquitin-mediated protcolysis of p53, comprising:
    (i) providing a eukaryotic cell engineered to express a recombinant ubiquitin conjugating enzyme encoded by a nucleic acid which hybridizes under high stringency conditions to a nucleic acid sequence of SEQ ID Nos.: 1, 3, or 5, wherein said cell also expresses a p53 regulatory protein and ubiquitin;
    (ii) contacting the eukaryotic cell with a candidate agent;
    (iii) measuring a level of ubiquitination of the p53 protein in the presence of the candidate agent; and
    (iv) comparing the measured level of ubiquitination in the presence of the candidate agent with a level of ubiquitination of p53 in the absence of the candidate agent,
wherein a decrease in ubiquitination of the p53 protein in the presence of the candidate agent is indicative of an inhibitor of ubiquitination of the p53 protein.

9. The assay of claim 8, wherein said cell also expresses a human papillomavirus protein able to interact with the p53 protein and mediate the ubiquitination of the p53 protein.

10. The assay of claim 9, wherein the human papillomavirus protein is an E6 protein.

11. The assay of claim 10, wherein the E6 protein is from a high-risk human papillomavirus.

12. The assay of claim 11, wherein the high-risk human papillomavirus is selected from the group consisting of HPV-16, HPV-18 and HPV-33.

13. The assay of claim 9, wherein said cell also expresses an E6-AP protein which functions to mediate the interaction of the human papillomavirus protein with the p53 protein.

14. The assay of claim 8, wherein the level of ubiquitination of the p53 protein is measured by quantifying an amount of ubiquitin-conjugated p53.

15. The assay of claim 14, wherein the amount of ubiquitin-conjugated p53 is quantified by measuring a change in apparent molecular weight of the p53 protein.

16. The assay of claim 14, wherein at least one of ubiquitin or a p53 protein comprises a detectable label, and the amount of ubiquitin-conjugated p53 is quantified by detecting the label in at least one of the p53 protein, the ubiquitin-conjugated p53.

17. The method of claim 16, wherein the label group is selected from the group consisting of radioisotopes, fluorescent compounds, enzymes, and enzyme co-factors.

18. The assay of claim 16, wherein the detectable label is a protein having a measurable activity, and the p53 protein is fusion protein including the detectable label.

19. The assay of claim 14, wherein the amount of ubiquitin-conjugated p53 is quantified by an immunoassay.

20. The assay of claim 8, wherein the ubiquitin-conjugating system further comprises a ubiquitin-dependent protease activity which degrades ubiquitin-conjugated p53, and the level of ubiquitination of the p53 protein is measured by quantifying the degradation of the p53 protein.

21. The assay of claim 9, wherein the eukaryotic cell is infected with a human papillomavirus.

22. The assay of claim 8, wherein the level of ubiquitination of the p53 protein is measured by an ability of the eukaryotic cell to prematurely pass a p53-mediated cell-cycle checkpoint.

23. The assay of claim 8, wherein the level of ubiquitination of the p53 protein is measured by the expression of a reporter gene under transcriptional control of the p53 protein.

24. The assay of claim 23, where the reporter gene further comprises a transcriptional control element selected from the group consisting of a creatine kinase enhancer, and interleukin-6 promoter, a c-fos promoter, a β-actin promoter, an hsc 70 promoter, a c-jun promoter, a p53 promoter, and a CYC1 hybrid promoter containing a p53-binding sequence.

25. An assay for identifying an inhibitor of E6-mediated degradation of p53, comprising;
    (i) providing a eukaryotic cell expressing an E6 protein from a human papillomavirus, a p53 protein, adenosine triphosphate, an E1 ubiquitin-activating enzyme, an E2 ubiquitin-conjugating enzyme encoded by a nucleic acid which hybridizes under high stringency conditions to a nucleic acid sequence of SEQ ID Nos.: 1, 3, or 5, and ubiquitin, under conditions wherein the E6 protein mediates ubiquitination of the p53 protein;
    (ii) contacting the eukaryotic cell with a candidate agent;
    (iii) measuring a level of ubiquitination of the p53 protein in the presence of the candidate agent; and
    (iv) comparing the measured level of ubiquitination in the presence of the candidate agent with a level of ubiquitination of p53 in the absence of the candidate agent, wherein a decrease in ubiquitination of the p53 protein in the presence of the candidate agent is indicative of an inhibitor of E6-mediated degradation of the p53 protein.

26. The assay of claim 25, wherein the eukaryotic cell further expresses an E6-AP protein.

27. The assay of claim 25, wherein the eukaryotic cell further expresses an E3 protein.

28. The method of claim 1, including the further step of formulating a composition comprising one or more of the identified inhibitors.

29. The method of claim 8, including the further step of formulating a composition comprising one or more of the identified inhibitors.

30. The method of claim 25, including the further step of formulating a composition comprising one or more of the identified inhibitors.

31. An assay for identifying an inhibitor of E6-mediated degradation of p53, comprising:
   (i) providing a eukaryotic cell which expresses a ubiquitin conjugating enzyme encoded by a nucleic acid which hybridizes under high stringency conditions to a nucleic acid sequence of SEQ ID Nos.: 1, 3, or 5, wherein said cell also expresses a human papillomavirus E6 protein which mediates ubiquitin-dependent degradation of p53 and results in an impaired p53 cell-cycle checkpoint under conditions wherein the impairment of the p53 cell-cycle checkpoint results in cell death;
   (ii) contacting the cell with a candidate agent;
   (iii) measuring a level of viability of the cell in the presence of the candidate agent; and
   (iv) comparing the level of viability of the cell in the presence of the candidate agent to a level of viability of the cell in the absence of the candidate agent, wherein an increase in the level of viability in the presence of the candidate agent is indicative of inhibition of the E6-mediated degradation of p53.

32. The assay of claim 31, wherein the conditions under which the impairment of the p53 cell-cycle checkpoint results in cell death comprises exposing the cells to a DNA damaging agent.

33. The assay of claim 32, wherein the DNA damaging agent is γ-radiation.

34. The assay of claim 31, wherein the impaired p53 cell-cycle checkpoint comprises a G1/S checkpoint.

* * * * *

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 444 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..441

(xi) SEQUENCE DESCRIPTION: SEQ ID NO:1:

```
ATG GCG CTG AAA CGG ATC CAC AAG GAA TTG AAT GAT CTG GCA CGG GAC        48
Met Ala Leu Lys Arg Ile His Lys Glu Leu Asn Asp Leu Ala Arg Asp
 1               5                  10                  15

CCT CCA GCA CAG TGT TCA GCA GGT CCT GTT GGA GAT GAT ATG TTC CAT        96
Pro Pro Ala Gln Cys Ser Ala Gly Pro Val Gly Asp Asp Met Phe His
                20                  25                  30

TGG CAA GCT ACA ATA ATG GGG CCA AAT GAC AGT CCC TAT CAG GGT GGA       144
```

```
Trp Gln Ala Thr Ile Met Gly Pro Asn Asp Ser Pro Tyr Gln Gly Gly
        35                  40                  45

GTA TTT TTC TTG ACA ATT CAT TTC CCA ACA GAT TAC CCC TTC AAA CCA    192
Val Phe Phe Leu Thr Ile His Phe Pro Thr Asp Tyr Pro Phe Lys Pro
50                      55                  60

CCT AAG GTT GCA TTT ACC ACA AGA ATT TAT CAT CCA AAT ATT AAC AGT    240
Pro Lys Val Ala Phe Thr Thr Arg Ile Tyr His Pro Asn Ile Asn Ser
65                  70                  75                  80

AAT GGC AGC ATT TGT CTT GAT ATT CTA CGA TCA CAG TGG TCT CCA GCA    288
Asn Gly Ser Ile Cys Leu Asp Ile Leu Arg Ser Gln Trp Ser Pro Ala
                85                  90                  95

CTA ACT ATT TCA AAA GTA CTC TTG TCC ATC TGT TCT CTG TTG TGT GAT    336
Leu Thr Ile Ser Lys Val Leu Leu Ser Ile Cys Ser Leu Leu Cys Asp
            100                 105                 110

CCC AAT CCA GAT GAT CCT TTA GTG CCT GAG ATT GCT CGG ATC TAC CAA    384
Pro Asn Pro Asp Asp Pro Leu Val Pro Glu Ile Ala Arg Ile Tyr Gln
        115                 120                 125

ACA GAT AGA GAA AAG TAC AAC AGA ATA GCT CGG GAA TGG ACT CAG AAG    432
Thr Asp Arg Glu Lys Tyr Asn Arg Ile Ala Arg Glu Trp Thr Gln Lys
130                 135                 140

TAT GCG ATG TAA                                                    444
Tyr Ala Met
145

(2) INFORMATION FOR SEQ ID NO:2:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Leu Lys Arg Ile His Lys Glu Leu Asn Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Gln
        115                 120                 125

Thr Asp Arg Glu Lys Tyr Asn Arg Ile Ala Arg Glu Trp Thr Gln Lys
130                 135                 140

Tyr Ala Met
145

(2) INFORMATION FOR SEQ ID NO:3:

(i) SEQUENCE CHARACTERISTICS:
        (A) LENGTH: 582 base pairs
        (B) TYPE: nucleic acid
```

(C) STRANDEDNESS: both
        (D) TOPOLOGY: linear (ii) MOLECULE TYPE: cDNA (ix) FEATURE:
        (A) NAME/KEY: CDS
        (B) LOCATION: 25..465

(xi) SEQUENCE DESCRIPTION: SEQ ID NO:3:

```
CACGAGTAAC TATTGCTTTA AATC ATG TCA TTA AAA CGT ATT AAC AAA GAA        51
                          Met Ser Leu Lys Arg Ile Asn Lys Glu
                           1               5

TTA TCT GAC TTA GGA AGA GAT CCA CCA TCA TCA TGT TCA GCC GGT CCA       99
Leu Ser Asp Leu Gly Arg Asp Pro Pro Ser Ser Cys Ser Ala Gly Pro
 10              15                  20                  25

GTT GGA GAT GAC TTA TAC CAC TGG CAA GCA TCT ATC ATG GGA CCA CCA      147
Val Gly Asp Asp Leu Tyr His Trp Gln Ala Ser Ile Met Gly Pro Pro
             30                  35                  40

GAC TCT CCA TAC GCT GGT GGG GTA TTT TTC TTG AGT ATC CAT TTC CCA      195
Asp Ser Pro Tyr Ala Gly Gly Val Phe Phe Leu Ser Ile His Phe Pro
                 45                  50                  55

ACA GAT TAT CCT TTA AAA CCA CCA AAG ATT GCT TTA ACA ACA AAA ATC      243
Thr Asp Tyr Pro Leu Lys Pro Pro Lys Ile Ala Leu Thr Thr Lys Ile
                     60                  65                  70

TAT CAT CCA AAT ATT AAT AGT AAT GGT AAC ATC TGT TTA GAT ATC TTA      291
Tyr His Pro Asn Ile Asn Ser Asn Gly Asn Ile Cys Leu Asp Ile Leu
 75                  80                  85

AAG GAT CAA TGG TCA CCT GCA TTA ACA ATT TCC AAA GTG TTA TTG TCT      339
Lys Asp Gln Trp Ser Pro Ala Leu Thr Ile Ser Lys Val Leu Leu Ser
 90                  95                 100                 105

ATT TGT TCA TTA TTA ACT GAT GCC AAC CCA GAC GAT CCA TTA GTG CCA      387
Ile Cys Ser Leu Leu Thr Asp Ala Asn Pro Asp Asp Pro Leu Val Pro
                110                 115                 120

GAA ATC GCT CAC ATT TAT AAA CAA GAT AGA AAG AAG TAT GAA GCT ACT      435
Glu Ile Ala His Ile Tyr Lys Gln Asp Arg Lys Lys Tyr Glu Ala Thr
                    125                 130                 135

GCC AAA GAA TGG ACT AAG AAA TAT GCT GTG TGATTTTAGA GAAAAACAAA        485
Ala Lys Glu Trp Thr Lys Lys Tyr Ala Val
                140                 145

AACATCTAAT TTCTACATGT ATTATGTCGT AATGCTTTCA CACAATACAA AAACATCTAA    545

TTTCTACATG TATTATGTCG TAATGCTTTC ACACAAT                             582
```

(2) INFORMATION FOR SEQ ID NO:4:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Leu Lys Arg Ile Asn Lys Glu Leu Ser Asp Leu Gly Arg Asp
 1               5                  10                  15

Pro Pro Ser Ser Cys Ser Ala Gly Pro Val Gly Asp Asp Leu Tyr His
                 20                  25                  30

Trp Gln Ala Ser Ile Met Gly Pro Pro Asp Ser Pro Tyr Ala Gly Gly
             35                  40                  45

Val Phe Phe Leu Ser Ile His Phe Pro Thr Asp Tyr Pro Leu Lys Pro
 50                  55                  60
```

```
Pro Lys Ile Ala Leu Thr Thr Lys Ile Tyr His Pro Asn Ile Asn Ser
 65                  70                  75                  80

Asn Gly Asn Ile Cys Leu Asp Ile Leu Lys Asp Gln Trp Ser Pro Ala
                 85                  90                  95

Leu Thr Ile Ser Lys Val Leu Leu Ser Ile Cys Ser Leu Leu Thr Asp
            100                 105                 110

Ala Asn Pro Asp Asp Pro Leu Val Pro Glu Ile Ala His Ile Tyr Lys
        115                 120                 125

Gln Asp Arg Lys Lys Tyr Glu Ala Thr Ala Lys Glu Trp Thr Lys Lys
130                 135                 140

Tyr Ala Val
145

(2) INFORMATION FOR SEQ ID NO:5:

(i) SEQUENCE CHARACTERISTICS:
        (A) LENGTH: 522 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 22..462

(xi) SEQUENCE DESCRIPTION: SEQ ID NO:5:
```

| | |
|---|---:|
| CGCAAAAGCA AACCAGTAAC G ATG GCT TTG AAA AGA ATT AAC CGT GAA TTA<br>                        Met Ala Leu Lys Arg Ile Asn Arg Glu Leu<br>                          1               5                  10 | 51 |
| GCT GAT CTT GGA AAA GAC CCA CCG TCT TCT TGT TCC GCC GGC CCT GTT<br>Ala Asp Leu Gly Lys Asp Pro Pro Ser Ser Cys Ser Ala Gly Pro Val<br>             15                  20                  25 | 99 |
| GGC GAT GAT TTA TTC CAT TGG CAA GCT ACA ATC ATG GGT CCT GCT GAC<br>Gly Asp Asp Leu Phe His Trp Gln Ala Thr Ile Met Gly Pro Ala Asp<br>                 30                  35                  40 | 147 |
| AGC CCT TAT GCG GGT GGT GTC TTC TTC TTG TCC ATT CAT TTC CCT ACG<br>Ser Pro Tyr Ala Gly Gly Val Phe Phe Leu Ser Ile His Phe Pro Thr<br>             45                  50                  55 | 195 |
| GAC TAC CCA TTC AAG CCA CCA AAG GTA AAC TTT ACA ACC AGA ATC TAT<br>Asp Tyr Pro Phe Lys Pro Pro Lys Val Asn Phe Thr Thr Arg Ile Tyr<br>         60                  65                  70 | 243 |
| CAT CCC AAC ATC AAT TCA AAC GGT AGC ATT TGT TTG GAT ATC CTT CGT<br>His Pro Asn Ile Asn Ser Asn Gly Ser Ile Cys Leu Asp Ile Leu Arg<br> 75                  80                  85                  90 | 291 |
| GAC CAA TGG TCT CCA GCG TTG ACT ATA TCA AAG GTA TTA CTG TCT ATC<br>Asp Gln Trp Ser Pro Ala Leu Thr Ile Ser Lys Val Leu Leu Ser Ile<br>             95                 100                 105 | 339 |
| TGC TCA TTG TTG ACA GAT CCT AAT CCT GAT GAT CCG CTT GTG CCT GAA<br>Cys Ser Leu Leu Thr Asp Pro Asn Pro Asp Asp Pro Leu Val Pro Glu<br>            110                 115                 120 | 387 |
| ATT GCG CAC GTC TAC AAA ACT GAC AGA TCC CGT TAT GAA TTA AGT GCT<br>Ile Ala His Val Tyr Lys Thr Asp Arg Ser Arg Tyr Glu Leu Ser Ala<br>        125                 130                 135 | 435 |
| CGT GAA TGG ACT AGA AAA TAC GCA ATC TAGAGTTTGT TTCTGTGTTG<br>Arg Glu Trp Thr Arg Lys Tyr Ala Ile<br>        140                 145 | 482 |
| ATATTAAATA TTCATCTCTT AAAAAAAAAA AAAAAACTCG | 522 |

```
(2) INFORMATION FOR SEQ ID NO:6:
```

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Leu Lys Arg Ile Asn Arg Glu Leu Ala Asp Leu Gly Lys Asp
 1               5                  10                  15

Pro Pro Ser Ser Cys Ser Ala Gly Pro Val Gly Asp Asp Leu Phe His
            20                  25                  30

Trp Gln Ala Thr Ile Met Gly Pro Ala Asp Ser Pro Tyr Ala Gly Gly
        35                  40                  45

Val Phe Phe Leu Ser Ile His Phe Pro Thr Asp Tyr Pro Phe Lys Pro
    50                  55                  60

Pro Lys Val Asn Phe Thr Thr Arg Ile Tyr His Pro Asn Ile Asn Ser
 65                  70                  75                  80

Asn Gly Ser Ile Cys Leu Asp Ile Leu Arg Asp Gln Trp Ser Pro Ala
                85                  90                  95

Leu Thr Ile Ser Lys Val Leu Leu Ser Ile Cys Ser Leu Leu Thr Asp
            100                 105                 110

Pro Asn Pro Asp Asp Pro Leu Val Pro Glu Ile Ala His Val Tyr Lys
        115                 120                 125

Thr Asp Arg Ser Arg Tyr Glu Leu Ser Ala Arg Glu Trp Thr Arg Lys
    130                 135                 140

Tyr Ala Ile
145

(2) INFORMATION FOR SEQ ID NO:7:

(i) SEQUENCE CHARACTERISTICS:
        (A) LENGTH: 147 amino acids
        (B) TYPE: amino acid
        (C) STRANDEDNESS:
        (D) TOPOLOGY: linear (ii) MOLECULE TYPE: protein (v) FRAGMENT TYPE: internal (xi) SEQUENCE DESCRIPTION: SEQ ID NO:7:

Met Xaa Leu Lys Arg Ile Xaa Xaa Glu Leu Xaa Asp Leu Xaa Xaa Asp
 1               5                  10                  15

Pro Pro Xaa Xaa Cys Ser Ala Gly Pro Val Gly Asp Asp Xaa Xaa His
            20                  25                  30

Trp Gln Ala Xaa Ile Met Gly Pro Asn Asp Ser Pro Tyr Xaa Gly Gly
        35                  40                  45

Val Phe Phe Leu Xaa Ile His Phe Pro Thr Asp Tyr Pro Xaa Lys Pro
    50                  55                  60

Pro Lys Xaa Xaa Xaa Thr Thr Xaa Ile Tyr His Pro Asn Ile Asn Ser
 65                  70                  75                  80

Asn Gly Xaa Ile Cys Leu Asp Ile Leu Xaa Xaa Gln Trp Ser Pro Ala
                85                  90                  95

Leu Thr Ile Ser Lys Val Leu Leu Ser Ile Cys Ser Leu Leu Xaa Asp
            100                 105                 110

Xaa Asn Pro Asp Asp Pro Leu Val Pro Glu Ile Ala Xaa Xaa Tyr Xaa
        115                 120                 125

```
Xaa Asp Arg Xaa Xaa Tyr Xaa Xaa Xaa Ala Xaa Glu Trp Thr Xaa Lys
    130                 135                 140

Tyr Ala Xaa
145
```

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

GCGCGCAAGC TTTAYGARGG WGGWGTYTTY TT                                32

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GCGCGCGAAT TCACNGCRTA YTTYTTNGTC CCAYTC                        36

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

GCGCGCAAGC TTCCNGTNGG NGAYTTRTTY CAYTGGCA                      38

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GCGCGCGAAT TCATNGTNAR NGCNGGCGAC CA                                32

(2) INFORMATION FOR SEQ ID NO:12:

(i) SEQUENCE CHARACTERISTICS:
        (A) LENGTH: 907 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 34..507

(xi) SEQUENCE DESCRIPTION: SEQ ID NO:12:

```
GCCGGGGCTG CGGCCGCCCG AGGGACTTTG AAC ATG TCG GGG ATC GCC CTC AGC          54
                                    Met Ser Gly Ile Ala Leu Ser
                                      1               5

AGA CTC GCC CAG GAG AGG AAA GCA TGG AGG AAA GAC CAC CCA TTT GGT          102
Arg Leu Ala Gln Glu Arg Lys Ala Trp Arg Lys Asp His Pro Phe Gly
         10                  15                  20

TTC GTG GCT GTC CCA ACA AAA AAT CCC GAT GGC ACG ATG AAC CTC ATG          150
Phe Val Ala Val Pro Thr Lys Asn Pro Asp Gly Thr Met Asn Leu Met
 25                  30                  35

AAC TGG GAG TGC GCC ATT CCA GGA AAG AAA GGG ACT CCG TGG GAA GGA          198
Asn Trp Glu Cys Ala Ile Pro Gly Lys Lys Gly Thr Pro Trp Glu Gly
 40                  45                  50                  55

GGC TTG TTT AAA CTA CGG ATG CTT TTC AAA GAT GAT TAT CCA TCT TCG          246
Gly Leu Phe Lys Leu Arg Met Leu Phe Lys Asp Asp Tyr Pro Ser Ser
                 60                  65                  70

CCA CCA AAA TGT AAA TTC GAA CCA CCA TTA TTT CAC CCG AAT GTG TAC          294
Pro Pro Lys Cys Lys Phe Glu Pro Pro Leu Phe His Pro Asn Val Tyr
             75                  80                  85

CCT TCG GGG ACA GTG TGC CTG TCC ATC TTA GAG GAG GAC AAG GAC TGG          342
Pro Ser Gly Thr Val Cys Leu Ser Ile Leu Glu Glu Asp Lys Asp Trp
         90                  95                 100

AGG CCA GCC ATC ACA ATC AAA CAG ATC CTA TTA GGA ATA CAG GAA CTT          390
Arg Pro Ala Ile Thr Ile Lys Gln Ile Leu Leu Gly Ile Gln Glu Leu
    105                 110                 115

CTA AAT GAA CCA AAT ATC CAA GAC CCA GCT CAA GCA GAG GCC TAC ACG          438
Leu Asn Glu Pro Asn Ile Gln Asp Pro Ala Gln Ala Glu Ala Tyr Thr
120                 125                 130                 135

ATT TAC TGC CAA AAC AGA GTG GAG TAC GAG AAA AGG GTC CGA GCA CAA          486
Ile Tyr Cys Gln Asn Arg Val Glu Tyr Glu Lys Arg Val Arg Ala Gln
                140                 145                 150

GCC AAG AAG TTT GCG CCC TCA TAAGCAGCGA CCTTGTGGCA TCGTCAAAAG            537
Ala Lys Lys Phe Ala Pro Ser
            155

GAAGGGATTG GTTTGGCAAG AACTTGTTTA CAACATTTTT GGCAAATCTA AAGTTGCTCC        597

ATACAATGAC TAGTCACCTG GGGGGGTTGG GCGGGCGCCA TCTTCCATTG CCGCCGCGGG        657

TGTGCGGTCT CGATTCGCTG AATTGCCCGT TTCCATACAG GGTCTCTTCC TTCGGTCTTT        717

TGGTATTTTT GGATTGTTAT GTAAAACTCG CTTTTATTTT AATATTGATG TCAGTATTTC        777

AACTGCTGTA AAATTATAAA CTTTTATACT GGGTAAGTCC CCCAGGGGCG AGTTNCCTCG        837

CTCTGGGATG CAGGCATGCT TCTCACCGTG CAGAGCTGCA CTTGNCCTCA GCTGNCTGNA        897

TGGAAATGCA                                                              907
```

(2) INFORMATION FOR SEQ ID NO:13:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:13:

```
Met Ser Gly Ile Ala Leu Ser Arg Leu Ala Gln Glu Arg Lys Ala Trp
  1               5                  10                  15

Arg Lys Asp His Pro Phe Gly Phe Val Ala Val Pro Thr Lys Asn Pro
             20                  25                  30
```

```
Asp Gly Thr Met Asn Leu Met Asn Trp Glu Cys Ala Ile Pro Gly Lys
        35                  40                  45

Lys Gly Thr Pro Trp Glu Gly Leu Phe Lys Leu Arg Met Leu Phe
    50                  55                  60

Lys Asp Asp Tyr Pro Ser Ser Pro Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
                100                 105                 110

Leu Leu Gly Ile Gln Glu Leu Leu Asn Glu Pro Asn Ile Gln Asp Pro
            115                 120                 125

Ala Gln Ala Glu Ala Tyr Thr Ile Tyr Cys Gln Asn Arg Val Glu Tyr
        130                 135                 140

Glu Lys Arg Val Arg Ala Gln Ala Lys Lys Phe Ala Pro Ser
145                 150                 155
```

(2) INFORMATION FOR SEQ ID NO:14:

(i) SEQUENCE CHARACTERISTICS:
        (A) LENGTH: 3176 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..3174

(xi) SEQUENCE DESCRIPTION: SEQ ID NO:14:

```
ATG TCC AGC TCG CCG CTG TCC AAG AAA CGT CGC GTG TCC GGG CCT GAT      48
Met Ser Ser Ser Pro Leu Ser Lys Lys Arg Arg Val Ser Gly Pro Asp
1               5                   10                  15

CCA AAG CCG GGT TCT AAC TGC TCC CCT GCC CAG TCC GTG TTG TCC GAA      96
Pro Lys Pro Gly Ser Asn Cys Ser Pro Ala Gln Ser Val Leu Ser Glu
            20                  25                  30

GTG CCC TCG GTG CCA ACC AAC GGA ATG GCC AAG AAC GGC AGT GAA GCA     144
Val Pro Ser Val Pro Thr Asn Gly Met Ala Lys Asn Gly Ser Glu Ala
        35                  40                  45

GAC ATA GAC GAG GGC CTT TAC TCC CGG CAG CTG TAT GTG TTG GGC CAT     192
Asp Ile Asp Glu Gly Leu Tyr Ser Arg Gln Leu Tyr Val Leu Gly His
    50                  55                  60

GAG GCA ATG AAG CGG CTC CAG ACA TCC AGT GTC CTG GTA TCA GGC CTG     240
Glu Ala Met Lys Arg Leu Gln Thr Ser Ser Val Leu Val Ser Gly Leu
65                  70                  75                  80

CGG GGC CTG GGC GTG GAG ATC GCT AAG AAC ATC ATC CTT GGT GGG GTC     288
Arg Gly Leu Gly Val Glu Ile Ala Lys Asn Ile Ile Leu Gly Gly Val
                85                  90                  95

AAG GCT GTT ACC CTA CAT GAC CAG GGC ACT GCC CAG TGG GCT GAT CTT     336
Lys Ala Val Thr Leu His Asp Gln Gly Thr Ala Gln Trp Ala Asp Leu
            100                 105                 110

TCC TCC CAG TTC TAC CTG CGG GAG GAG GAC ATC GGT AAA AAC CGG GCC     384
Ser Ser Gln Phe Tyr Leu Arg Glu Glu Asp Ile Gly Lys Asn Arg Ala
        115                 120                 125

GAG GTA TCA CAG CCC CGC CTC GCT GAG CTC AAC AGC TAT GTG CCT GTC     432
Glu Val Ser Gln Pro Arg Leu Ala Glu Leu Asn Ser Tyr Val Pro Val
    130                 135                 140

ACT GCC TAC ACT GGA CCC CTC GTT GAG GAC TTC CTT AGT GGT TTC CAG     480
```

-continued

```
Thr Ala Tyr Thr Gly Pro Leu Val Glu Asp Phe Leu Ser Gly Phe Gln
145                 150                 155                 160

GTG GTG GTG CTC ACC AAC ACC CCC CTG GAG GAC CAG CTG CGA GTG GGT        528
Val Val Val Leu Thr Asn Thr Pro Leu Glu Asp Gln Leu Arg Val Gly
                165                 170                 175

GAG TTC TGT CAC AAC CGT GGC ATC AAG CTG GTG GTG GCA GAC ACG CGG        576
Glu Phe Cys His Asn Arg Gly Ile Lys Leu Val Val Ala Asp Thr Arg
            180                 185                 190

GGC CTG TTT GGG CAG CTC TTC TGT GAC TTT GGA GAG GAA ATG ATC CTC        624
Gly Leu Phe Gly Gln Leu Phe Cys Asp Phe Gly Glu Glu Met Ile Leu
        195                 200                 205

ACA GAT TCC AAT GGG GAG CAG CCA CTC AGT GCT ATG GTT TCT ATG GTT        672
Thr Asp Ser Asn Gly Glu Gln Pro Leu Ser Ala Met Val Ser Met Val
    210                 215                 220

ACC AAG GAC AAC CCC GGT GTG GTT ACC TGC CTG GAT GAG GCC CGA CAC        720
Thr Lys Asp Asn Pro Gly Val Val Thr Cys Leu Asp Glu Ala Arg His
225                 230                 235                 240

GGG TTT GAG AGC GGG GAC TTT GTC TCC TTT TCA GAA GTA CAG GGC ATG        768
Gly Phe Glu Ser Gly Asp Phe Val Ser Phe Ser Glu Val Gln Gly Met
                245                 250                 255

GTT GAA CTC AAC GGA AAT CAG CCC ATG GAG ATC AAA GTC CTG GGT CCT        816
Val Glu Leu Asn Gly Asn Gln Pro Met Glu Ile Lys Val Leu Gly Pro
            260                 265                 270

TAT ACC TTT AGC ATC TGT GAC ACC TCC AAC TTC TCC GAC TAC ATC CGT        864
Tyr Thr Phe Ser Ile Cys Asp Thr Ser Asn Phe Ser Asp Tyr Ile Arg
        275                 280                 285

GGA GGC ATC GTC AGT CAG GTC AAA GTA CCT AAG AAG ATT AGC TTT AAA        912
Gly Gly Ile Val Ser Gln Val Lys Val Pro Lys Lys Ile Ser Phe Lys
    290                 295                 300

TCC TTG GTG GCC TCA CTG GCA GAA CCT GAC TTT GTG GTG ACG GAC TTC        960
Ser Leu Val Ala Ser Leu Ala Glu Pro Asp Phe Val Val Thr Asp Phe
305                 310                 315                 320

GCC AAG TTT TCT CGC CCT GCC CAG CTG CAC ATT GGC TTC CAG GCC CTG       1008
Ala Lys Phe Ser Arg Pro Ala Gln Leu His Ile Gly Phe Gln Ala Leu
                325                 330                 335

CAC CAG TTC TGT GCT CAG CAT GGC CGG CCA CCT CGG CCC CGC AAT GAG       1056
His Gln Phe Cys Ala Gln His Gly Arg Pro Pro Arg Pro Arg Asn Glu
            340                 345                 350

GAG GAT GCA GCA GAA CTG GTA GCC TTA GCA CAG GCT GTG AAT GCT CGA       1104
Glu Asp Ala Ala Glu Leu Val Ala Leu Ala Gln Ala Val Asn Ala Arg
        355                 360                 365

GCC CTG CCA GCA GTG CAG CAA AAT AAC CTG GAC GAG GAC CTC ATC CGG       1152
Ala Leu Pro Ala Val Gln Gln Asn Asn Leu Asp Glu Asp Leu Ile Arg
    370                 375                 380

AAG CTG GCA TAT GTG GCT GCT GGG GAT CTG GCA CCC ATA AAC GCC TTC       1200
Lys Leu Ala Tyr Val Ala Ala Gly Asp Leu Ala Pro Ile Asn Ala Phe
385                 390                 395                 400

ATT GGG GGC CTG GCT GCC CAG GAA GTC ATG AAG GCC TGC TCC GGG AAG       1248
Ile Gly Gly Leu Ala Ala Gln Glu Val Met Lys Ala Cys Ser Gly Lys
                405                 410                 415

TTC ATG CCC ATC ATG CAG TGG CTA TAC TTT GAT GCC CTT GAG TGT CTC       1296
Phe Met Pro Ile Met Gln Trp Leu Tyr Phe Asp Ala Leu Glu Cys Leu
            420                 425                 430

CCT GAG GAC AAA GAG GTC CTC ACA GAG GAC AAG TGC CTC CAG CGC CAG       1344
Pro Glu Asp Lys Glu Val Leu Thr Glu Asp Lys Cys Leu Gln Arg Gln
        435                 440                 445

AAC CGT TAT GAC GGG CAA GTG GCT GTG TTT GGC TCA GAC CTG CAA GAG       1392
Asn Arg Tyr Asp Gly Gln Val Ala Val Phe Gly Ser Asp Leu Gln Glu
    450                 455                 460
```

-continued

```
AAG CTG GGC AAG CAG AAG TAT TTC CTG GTG GGT GCG GGG GCC ATT GGC    1440
Lys Leu Gly Lys Gln Lys Tyr Phe Leu Val Gly Ala Gly Ala Ile Gly
465                 470                 475                 480

TGT GAG CTG CTC AAG AAC TTT GCC ATG ATT GGG CTG GGC TGC GGG GAG    1488
Cys Glu Leu Leu Lys Asn Phe Ala Met Ile Gly Leu Gly Cys Gly Glu
                485                 490                 495

GGT GGA GAA ATC ATC GTT ACA GAC ATG GAC ACC ATT GAG AAG TCA AAT    1536
Gly Gly Glu Ile Ile Val Thr Asp Met Asp Thr Ile Glu Lys Ser Asn
            500                 505                 510

CTG AAT CGA CAG TTT CTT TTC CGG CCC TGG GAT GTC ACG AAG TTA AAG    1584
Leu Asn Arg Gln Phe Leu Phe Arg Pro Trp Asp Val Thr Lys Leu Lys
        515                 520                 525

TCT GAC ACG GCT GCT GCA GCT GTG CGC CAA ATG AAT CCA CAT ATC CGG    1632
Ser Asp Thr Ala Ala Ala Ala Val Arg Gln Met Asn Pro His Ile Arg
    530                 535                 540

GTG ACA AGC CAC CAG AAC CGT GTG GGT CCT GAC ACG GAG CGC ATC TAT    1680
Val Thr Ser His Gln Asn Arg Val Gly Pro Asp Thr Glu Arg Ile Tyr
545                 550                 555                 560

GAT GAC GAT TTT TTC CAA AAC CTA GAT GGC GTG GCC AAT GCC CTG GAC    1728
Asp Asp Asp Phe Phe Gln Asn Leu Asp Gly Val Ala Asn Ala Leu Asp
                565                 570                 575

AAC GTG GAT GCC CGC ATG TAC ATG GAC CGC CGC TGT GTC TAC TAC CGG    1776
Asn Val Asp Ala Arg Met Tyr Met Asp Arg Arg Cys Val Tyr Tyr Arg
            580                 585                 590

AAG CCA CTG CTG GAG TCA GGC ACA CTG GGC ACC AAA GGC AAT GTG CAG    1824
Lys Pro Leu Leu Glu Ser Gly Thr Leu Gly Thr Lys Gly Asn Val Gln
        595                 600                 605

GTG GTG ATC CCC TTC CTG ACA GAG TCG TAC AGT TCC AGC CAG GAC CCA    1872
Val Val Ile Pro Phe Leu Thr Glu Ser Tyr Ser Ser Ser Gln Asp Pro
    610                 615                 620

CCT GAG AAG TCC ATC CCC ATC TGT ACC CTG AAG AAC TTC CCT AAT GCC    1920
Pro Glu Lys Ser Ile Pro Ile Cys Thr Leu Lys Asn Phe Pro Asn Ala
625                 630                 635                 640

ATC GAG CAC ACC CTG CAG TGG GCT CGG GAT GAG TTT GAA GGC CTC TTC    1968
Ile Glu His Thr Leu Gln Trp Ala Arg Asp Glu Phe Glu Gly Leu Phe
                645                 650                 655

AAG CAG CCA GCA GAA AAT GTC AAC CAG TAC CTC ACA GAC CCC AAG TTT    2016
Lys Gln Pro Ala Glu Asn Val Asn Gln Tyr Leu Thr Asp Pro Lys Phe
            660                 665                 670

GTG GAG CGA ACA CTG CGG CTG GCA GGC ACT CAG CCC TTG GAG GTG CTG    2064
Val Glu Arg Thr Leu Arg Leu Ala Gly Thr Gln Pro Leu Glu Val Leu
        675                 680                 685

GAG GCT GTG CAG CGC AGC CTG GTG CTG CAG CGA CCA CAG ACC TGG GCT    2112
Glu Ala Val Gln Arg Ser Leu Val Leu Gln Arg Pro Gln Thr Trp Ala
    690                 695                 700

GAC TGC GTG ACC TGG GCC TGC CAC CAC TGG CAC ACC CAG TAC TCG AAC    2160
Asp Cys Val Thr Trp Ala Cys His His Trp His Thr Gln Tyr Ser Asn
705                 710                 715                 720

AAC ATC CGG CAG CTG CTG CAC AAC TTC CCT CCT GAC CAG CTC ACA AGC    2208
Asn Ile Arg Gln Leu Leu His Asn Phe Pro Pro Asp Gln Leu Thr Ser
                725                 730                 735

TCA GGA GCG CCG TTC TGG TCT GGG CCC AAA CGC TGT CCA CAC CCG CTC    2256
Ser Gly Ala Pro Phe Trp Ser Gly Pro Lys Arg Cys Pro His Pro Leu
            740                 745                 750

ACC TTT GAT GTC AAC AAT CCC CTG CAT CTG GAC TAT GTG ATG GCT GCT    2304
Thr Phe Asp Val Asn Asn Pro Leu His Leu Asp Tyr Val Met Ala Ala
        755                 760                 765

GCC AAC CTG TTT GCC CAG ACC TAC GGG CTG ACA GGC TCT CAG GAC CGA    2352
Ala Asn Leu Phe Ala Gln Thr Tyr Gly Leu Thr Gly Ser Gln Asp Arg
    770                 775                 780
```

-continued

```
GCT GCT GTG GCC ACA TTC CTG CAG TCT GTG CAG GTC CCC GAA TTC ACC       2400
Ala Ala Val Ala Thr Phe Leu Gln Ser Val Gln Val Pro Glu Phe Thr
785                 790                 795                 800

CCC AAG TCT GGC GTC AAG ATC CAT GTT TCT GAC CAG GAG CTG CAG AGC       2448
Pro Lys Ser Gly Val Lys Ile His Val Ser Asp Gln Glu Leu Gln Ser
                805                 810                 815

GCC AAT GCC TCT GTT GAT GAC AGT CGT CTA GAG GAG CTC AAA GCC ACT       2496
Ala Asn Ala Ser Val Asp Asp Ser Arg Leu Glu Glu Leu Lys Ala Thr
            820                 825                 830

CTG CCC AGC CCA GAC AAG CTC CCT GGA TTC AAG ATG TAC CCC ATT GAC       2544
Leu Pro Ser Pro Asp Lys Leu Pro Gly Phe Lys Met Tyr Pro Ile Asp
        835                 840                 845

TTT GAG AAG GAT GAT GAC AGC AAC TTT CAT ATG GAT TTC ATC GTG GCT       2592
Phe Glu Lys Asp Asp Asp Ser Asn Phe His Met Asp Phe Ile Val Ala
850                 855                 860

GCA TCC AAC CTC CGG GCA GAA AAC TAT GAC ATT CCT TCT GCA GAC CGG       2640
Ala Ser Asn Leu Arg Ala Glu Asn Tyr Asp Ile Pro Ser Ala Asp Arg
865                 870                 875                 880

CAC AAG AGC AAG CTG ATT GCA GGG AAG ATC ATC CCA GCC ATT GCC ACG       2688
His Lys Ser Lys Leu Ile Ala Gly Lys Ile Ile Pro Ala Ile Ala Thr
                885                 890                 895

ACC ACA GCA GCC GTG GTT GGC CTT GTG TGT CTG GAA CTG TAC AAG GTT       2736
Thr Thr Ala Ala Val Val Gly Leu Val Cys Leu Glu Leu Tyr Lys Val
            900                 905                 910

GTG CAG GGG CAC CGA CAG CTT GAC TCC TAC AAG AAT GGT TTC CTC AAC       2784
Val Gln Gly His Arg Gln Leu Asp Ser Tyr Lys Asn Gly Phe Leu Asn
        915                 920                 925

TTG GCC CTG CCT TTC TTT GGT TTC TCT GAA CCC CTT GCC GCA CCA CGT       2832
Leu Ala Leu Pro Phe Phe Gly Phe Ser Glu Pro Leu Ala Ala Pro Arg
    930                 935                 940

CAC CAG TAC TAT AAC CAA GAG TGG ACA TTG TGG GAT CGC TTT GAG GTA       2880
His Gln Tyr Tyr Asn Gln Glu Trp Thr Leu Trp Asp Arg Phe Glu Val
945                 950                 955                 960

CAA GGG CTG CAG CCT AAT GGT GAG GAG ATG ACC CTC AAA CAG TTC CTC       2928
Gln Gly Leu Gln Pro Asn Gly Glu Glu Met Thr Leu Lys Gln Phe Leu
                965                 970                 975

GAC TAT TTT AAG ACA GAG CAC AAA TTA GAG ATC ACC ATG CTG TCC CAG       2976
Asp Tyr Phe Lys Thr Glu His Lys Leu Glu Ile Thr Met Leu Ser Gln
            980                 985                 990

GGC GTG TCC ATG CTC TAT TCC TTC TTC ATG CCA GCT GCC AAG CTC AAG       3024
Gly Val Ser Met Leu Tyr Ser Phe Phe Met Pro Ala Ala Lys Leu Lys
        995                 1000                1005

GAA CGG TTG GAT CAG CCG ATG ACA GAG ATT GTG AGC CGT GTG TCG AAG       3072
Glu Arg Leu Asp Gln Pro Met Thr Glu Ile Val Ser Arg Val Ser Lys
    1010                1015                1020

CGA AAG CTG GGC CGC CAC GTG CGG GCG CTG GTG CTT GAG CTG TGC TGT       3120
Arg Lys Leu Gly Arg His Val Arg Ala Leu Val Leu Glu Leu Cys Cys
1025                1030                1035                1040

AAC GAC GAG AGC GGC GAG GAT GTC GAG GTT CCC TAT GTC CGA TAC ACC       3168
Asn Asp Glu Ser Gly Glu Asp Val Glu Val Pro Tyr Val Arg Tyr Thr
                1045                1050                1055

ATC CGC TG                                                             3176
Ile Arg
```

(2) INFORMATION FOR SEQ ID NO:15:

(i) SEQUENCE CHARACTERISTICS:
        (A) LENGTH: 1058 amino acids
        (B) TYPE: amino acid
        (D) TOPOLOGY: linear (ii) MOLECULE TYPE: protein (xi) SEQUENCE DESCRIPTION: SEQ ID NO:15:

| Met | Ser | Ser | Ser | Pro | Leu | Ser | Lys | Lys | Arg | Arg | Val | Ser | Gly | Pro | Asp |
|---|---|---|---|---|---|---|---|---|---|---|---|---|---|---|---|
| 1 | | | | 5 | | | | | 10 | | | | | 15 | |

Pro Lys Pro Gly Ser Asn Cys Ser Pro Ala Gln Ser Val Leu Ser Glu
             20                  25                  30

Val Pro Ser Val Pro Thr Asn Gly Met Ala Lys Asn Gly Ser Glu Ala
             35                  40                  45

Asp Ile Asp Glu Gly Leu Tyr Ser Arg Gln Leu Tyr Val Leu Gly His
 50                      55                      60

Glu Ala Met Lys Arg Leu Gln Thr Ser Ser Val Leu Val Ser Gly Leu
 65                      70                      75                  80

Arg Gly Leu Gly Val Glu Ile Ala Lys Asn Ile Ile Leu Gly Gly Val
                     85                  90                      95

Lys Ala Val Thr Leu His Asp Gln Gly Thr Ala Gln Trp Ala Asp Leu
             100                 105                 110

Ser Ser Gln Phe Tyr Leu Arg Glu Glu Asp Ile Gly Lys Asn Arg Ala
             115                 120                 125

Glu Val Ser Gln Pro Arg Leu Ala Glu Leu Asn Ser Tyr Val Pro Val
130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                 165                 170                 175

Glu Phe Cys His Asn Arg Gly Ile Lys Leu Val Val Ala Asp Thr Arg
             180                 185                 190

Gly Leu Phe Gly Gln Leu Phe Cys Asp Phe Gly Glu Glu Met Ile Leu
             195                 200                 205

Thr Asp Ser Asn Gly Glu Gln Pro Leu Ser Ala Met Val Ser Met Val
210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
             245                 250                 255

Val Glu Leu Asn Gly Asn Gln Pro Met Glu Ile Lys Val Leu Gly Pro
             260                 265                 270

Tyr Thr Phe Ser Ile Cys Asp Thr Ser Asn Phe Ser Asp Tyr Ile Arg
             275                 280                 285

Gly Gly Ile Val Ser Gln Val Lys Val Pro Lys Lys Ile Ser Phe Lys
             290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
             325                 330                 335

His Gln Phe Cys Ala Gln His Gly Arg Pro Pro Arg Pro Arg Asn Glu
             340                 345                 350

Glu Asp Ala Ala Glu Leu Val Ala Leu Ala Gln Ala Val Asn Ala Arg
             355                 360                 365

Ala Leu Pro Ala Val Gln Gln Asn Asn Leu Asp Glu Asp Leu Ile Arg
             370                 375                 380

Lys Leu Ala Tyr Val Ala Ala Gly Asp Leu Ala Pro Ile Asn Ala Phe
385                 390                 395                 400

-continued

```
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Val Leu Thr Glu Asp Lys Cys Leu Gln Arg Gln
        435                 440                 445
Asn Arg Tyr Asp Gly Gln Val Ala Val Phe Gly Ser Asp Leu Gln Glu
    450                 455                 460
Lys Leu Gly Lys Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Gly Glu
                485                 490                 495
Gly Gly Glu Ile Ile Val Thr Asp Met Asp Thr Ile Glu Lys Ser Asn
            500                 505                 510
Leu Asn Arg Gln Phe Leu Phe Arg Pro Trp Asp Val Thr Lys Leu Lys
        515                 520                 525
Ser Asp Thr Ala Ala Ala Val Arg Gln Met Asn Pro His Ile Arg
    530                 535                 540
Val Thr Ser His Gln Asn Arg Val Gly Pro Asp Thr Glu Arg Ile Tyr
545                 550                 555                 560
Asp Asp Asp Phe Phe Gln Asn Leu Asp Gly Val Ala Asn Ala Leu Asp
                565                 570                 575
Asn Val Asp Ala Arg Met Tyr Met Asp Arg Arg Cys Val Tyr Tyr Arg
            580                 585                 590
Lys Pro Leu Leu Glu Ser Gly Thr Leu Gly Thr Lys Gly Asn Val Gln
        595                 600                 605
Val Val Ile Pro Phe Leu Thr Glu Ser Tyr Ser Ser Ser Gln Asp Pro
    610                 615                 620
Pro Glu Lys Ser Ile Pro Ile Cys Thr Leu Lys Asn Phe Pro Asn Ala
625                 630                 635                 640
Ile Glu His Thr Leu Gln Trp Ala Arg Asp Glu Phe Glu Gly Leu Phe
                645                 650                 655
Lys Gln Pro Ala Glu Asn Val Asn Gln Tyr Leu Thr Asp Pro Lys Phe
            660                 665                 670
Val Glu Arg Thr Leu Arg Leu Ala Gly Thr Gln Pro Leu Glu Val Leu
        675                 680                 685
Glu Ala Val Gln Arg Ser Leu Val Leu Gln Arg Pro Gln Thr Trp Ala
    690                 695                 700
Asp Cys Val Thr Trp Ala Cys His His Trp His Thr Gln Tyr Ser Asn
705                 710                 715                 720
Asn Ile Arg Gln Leu Leu His Asn Phe Pro Pro Asp Gln Leu Thr Ser
                725                 730                 735
Ser Gly Ala Pro Phe Trp Ser Gly Pro Lys Arg Cys Pro His Pro Leu
            740                 745                 750
Thr Phe Asp Val Asn Asn Pro Leu His Leu Asp Tyr Val Met Ala Ala
        755                 760                 765
Ala Asn Leu Phe Ala Gln Thr Tyr Gly Leu Thr Gly Ser Gln Asp Arg
    770                 775                 780
Ala Ala Val Ala Thr Phe Leu Gln Ser Val Gln Val Pro Glu Phe Thr
785                 790                 795                 800
Pro Lys Ser Gly Val Lys Ile His Val Ser Asp Gln Glu Leu Gln Ser
                805                 810                 815
```

-continued

```
Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
            835                 840                 845

Phe Glu Lys Asp Asp Asp Ser Asn Phe His Met Asp Phe Ile Val Ala
850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
            915                 920                 925

Leu Ala Leu Pro Phe Phe Gly Phe Ser Glu Pro Leu Ala Ala Pro Arg
            930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
            995                 1000                1005

Glu Arg Leu Asp Gln Pro Met Thr Glu Ile Val Ser Arg Val Ser Lys
            1010                1015                1020

Arg Lys Leu Gly Arg His Val Arg Ala Leu Val Leu Glu Leu Cys Cys
1025                1030                1035                1040

Asn Asp Glu Ser Gly Glu Asp Val Glu Val Pro Tyr Val Arg Tyr Thr
                1045                1050                1055

Ile Arg (2) INFORMATION FOR SEQ ID NO:16:

(i) SEQUENCE CHARACTERISTICS:
        (A) LENGTH: 458 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..456

(xi) SEQUENCE DESCRIPTION: SEQ ID NO:16:

ATG TCG ACC CCG GCC CGG AGG AGG CTC ATG CGG GAT TTC AAG CGG TTA       48
Met Ser Thr Pro Ala Arg Arg Arg Leu Met Arg Asp Phe Lys Arg Leu
 1               5                  10                  15

CAA GAG GAC CCA CCT GTG GGT GTC AGT GGC GCA CCA TCT GAA AAC AAC       96
Gln Glu Asp Pro Pro Val Gly Val Ser Gly Ala Pro Ser Glu Asn Asn
                20                  25                  30

ATC ATG CAG TGG AAT GCA GTT ATA TTT GGA CCA GAA GGG ACA CCT TTT      144
Ile Met Gln Trp Asn Ala Val Ile Phe Gly Pro Glu Gly Thr Pro Phe
            35                  40                  45

GAA GAT GGT ACT TTT AAA CTA GTA ATA GAA TTT TCT GAA GAA TAT CCA      192
Glu Asp Gly Thr Phe Lys Leu Val Ile Glu Phe Ser Glu Glu Tyr Pro
        50                  55                  60
```

```
AAT AAA CCA CCA ACT GTT AGG TTT TTA TCC AAA ATG TTT CAT CCA AAT      240
Asn Lys Pro Pro Thr Val Arg Phe Leu Ser Lys Met Phe His Pro Asn
 65          70                  75                  80

GTG TAT GCT GAT GGT AGC ATA TGT TTA GAT ATC CTT CAG AAT CGA TGG      288
Val Tyr Ala Asp Gly Ser Ile Cys Leu Asp Ile Leu Gln Asn Arg Trp
                 85                  90                  95

AGT CCA ACA TAT GAT GTA TCT TCT ATC TTA ACA TCA ATT CAG TCT CTG      336
Ser Pro Thr Tyr Asp Val Ser Ser Ile Leu Thr Ser Ile Gln Ser Leu
            100                 105                 110

CTG GAT GAA CCG AAT CCT AAC AGT CCA GCC AAT AGC CAG GCA GCA CAG      384
Leu Asp Glu Pro Asn Pro Asn Ser Pro Ala Asn Ser Gln Ala Ala Gln
        115                 120                 125

CTT TAT CAG GAA AAC AAA CGA GAA TAT GAG AAA AGA GTT TCG GCC ATT      432
Leu Tyr Gln Glu Asn Lys Arg Glu Tyr Glu Lys Arg Val Ser Ala Ile
130                 135                 140

GTT GAA CAA AGC TGG AAT GAT TCA TA                                   458
Val Glu Gln Ser Trp Asn Asp Ser
145                 150
```

(2) INFORMATION FOR SEQ ID NO:17:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:17:

```
Met Ser Thr Pro Ala Arg Arg Arg Leu Met Arg Asp Phe Lys Arg Leu
 1               5                  10                  15

Gln Glu Asp Pro Pro Val Gly Val Ser Gly Ala Pro Ser Glu Asn Asn
                 20                  25                  30

Ile Met Gln Trp Asn Ala Val Ile Phe Gly Pro Glu Gly Thr Pro Phe
            35                  40                  45

Glu Asp Gly Thr Phe Lys Leu Val Ile Glu Phe Ser Glu Glu Tyr Pro
        50                  55                  60

Asn Lys Pro Pro Thr Val Arg Phe Leu Ser Lys Met Phe His Pro Asn
 65                  70                  75                  80

Val Tyr Ala Asp Gly Ser Ile Cys Leu Asp Ile Leu Gln Asn Arg Trp
                 85                  90                  95

Ser Pro Thr Tyr Asp Val Ser Ser Ile Leu Thr Ser Ile Gln Ser Leu
            100                 105                 110

Leu Asp Glu Pro Asn Pro Asn Ser Pro Ala Asn Ser Gln Ala Ala Gln
        115                 120                 125

Leu Tyr Gln Glu Asn Lys Arg Glu Tyr Glu Lys Arg Val Ser Ala Ile
130                 135                 140

Val Glu Gln Ser Trp Asn Asp Ser
145                 150
```

(2) INFORMATION FOR SEQ ID NO:18:

(i) SEQUENCE CHARACTERISTICS:
        (A) LENGTH: 476 base pairs
        (B) TYPE: nucleic acid
        (C) STRANDEDNESS: both
        (D) TOPOLOGY: linear (ii) MOLECULE TYPE: cDNA (ix) FEATURE:

```
          (A) NAME/KEY: CDS
          (B) LOCATION: 1..474

(xi) SEQUENCE DESCRIPTION: SEQ ID NO:18:

ATG GCG CGC TTT GAG GAT CCA ACA CGG CGA CCC TAC AAG CTA CCT GAT      48
Met Ala Arg Phe Glu Asp Pro Thr Arg Arg Pro Tyr Lys Leu Pro Asp
 1               5                  10                  15

CTG TGC ACG GAA CTG AAC ACT TCA CTG CAA GAC ATA GAA ATA ACC TGT      96
Leu Cys Thr Glu Leu Asn Thr Ser Leu Gln Asp Ile Glu Ile Thr Cys
             20                  25                  30

GTA TAT TGC AAG ACA GTA TTG GAA CTT ACA GAG GTA TTT GAA TTT GCA     144
Val Tyr Cys Lys Thr Val Leu Glu Leu Thr Glu Val Phe Glu Phe Ala
         35                  40                  45

TTT AAA GAT TTA TTT GTG GTG TAT AGA GAC AGT ATA CCG CAT GCT GCA     192
Phe Lys Asp Leu Phe Val Val Tyr Arg Asp Ser Ile Pro His Ala Ala
     50                  55                  60

TGC CAT AAA TGT ATA GAT TTT TAT TCT AGA ATT AGA GAA TTA AGA CAT     240
Cys His Lys Cys Ile Asp Phe Tyr Ser Arg Ile Arg Glu Leu Arg His
 65                  70                  75                  80

TAT TCA GAC TCT GTG TAT GGA GAC ACA TTG GAA AAA CTA ACT AAC ACT     288
Tyr Ser Asp Ser Val Tyr Gly Asp Thr Leu Glu Lys Leu Thr Asn Thr
                 85                  90                  95

GGG TTA TAC AAT TTA TTA ATA AGG TGC CTG CGG TGC CAG AAA CCG TTG     336
Gly Leu Tyr Asn Leu Leu Ile Arg Cys Leu Arg Cys Gln Lys Pro Leu
            100                 105                 110

AAT CCA GCA GAA AAA CTT AGA CAC CTT AAT GAA AAA CGA CGA TTT CAC     384
Asn Pro Ala Glu Lys Leu Arg His Leu Asn Glu Lys Arg Arg Phe His
        115                 120                 125

AAC ATA GCT GGG CAC TAT AGA GGC CAG TGC CAT TCG TGC TGC AAC CGA     432
Asn Ile Ala Gly His Tyr Arg Gly Gln Cys His Ser Cys Cys Asn Arg
    130                 135                 140

GCA CGA CAG GAA CGA CTC CAA CGA CGC AGA GAA ACA CAA GTA             474
Ala Arg Gln Glu Arg Leu Gln Arg Arg Arg Glu Thr Gln Val
145                 150                 155

TA                                                                  476

(2) INFORMATION FOR SEQ ID NO:19:

(i) SEQUENCE CHARACTERISTICS:
          (A) LENGTH: 158 amino acids
          (B) TYPE: amino acid
          (D) TOPOLOGY: linear (ii) MOLECULE TYPE: protein (xi) SEQUENCE DESCRIPTION: SEQ ID NO:19:

Met Ala Arg Phe Glu Asp Pro Thr Arg Arg Pro Tyr Lys Leu Pro Asp
 1               5                  10                  15

Leu Cys Thr Glu Leu Asn Thr Ser Leu Gln Asp Ile Glu Ile Thr Cys
             20                  25                  30

Val Tyr Cys Lys Thr Val Leu Glu Leu Thr Glu Val Phe Glu Phe Ala
         35                  40                  45

Phe Lys Asp Leu Phe Val Val Tyr Arg Asp Ser Ile Pro His Ala Ala
     50                  55                  60

Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
            100                 105                 110
```

```
Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
        130                 135                 140

Ala Arg Gln Glu Arg Leu Gln Arg Arg Glu Thr Gln Val
145                 150                 155
```

(2) INFORMATION FOR SEQ ID NO:20:

(i) SEQUENCE CHARACTERISTICS:
        (A) LENGTH: 2624 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..2622

(xi) SEQUENCE DESCRIPTION: SEQ ID NO:20:

```
TCA GGA GAA CCT CAG TCT GAC GAC ATT GAA GCT AGC CGA ATG AAG CGA         48
Ser Gly Glu Pro Gln Ser Asp Asp Ile Glu Ala Ser Arg Met Lys Arg
 1               5                  10                  15

GCA GCT GCA AAG CAT CTA ATA GAA CGC TAC TAC CAC CAG TTA ACT GAG         96
Ala Ala Ala Lys His Leu Ile Glu Arg Tyr Tyr His Gln Leu Thr Glu
                20                  25                  30

GGC TGT GGA AAT GAA GCC TGC ACG AAT GAG TTT TGT GCT TCC TGT CCA        144
Gly Cys Gly Asn Glu Ala Cys Thr Asn Glu Phe Cys Ala Ser Cys Pro
            35                  40                  45

ACT TTT CTT CGT ATG GAT AAT AAT GCA GCA GCT ATT AAA GCC CTC GAG        192
Thr Phe Leu Arg Met Asp Asn Asn Ala Ala Ala Ile Lys Ala Leu Glu
        50                  55                  60

CTT TAT AAG ATT AAT GCA AAA CTC TGT GAT CCT CAT CCC TCC AAG AAA        240
Leu Tyr Lys Ile Asn Ala Lys Leu Cys Asp Pro His Pro Ser Lys Lys
65                  70                  75                  80

GGA GCA AGC TCA GCT TAC CTT GAG AAC TCG AAA GGT GCC CCC AAC AAC        288
Gly Ala Ser Ser Ala Tyr Leu Glu Asn Ser Lys Gly Ala Pro Asn Asn
                85                  90                  95

TCC TGC TCT GAG ATA AAA ATG AAC AAG AAA GGC GCT AGA ATT GAT TTT        336
Ser Cys Ser Glu Ile Lys Met Asn Lys Lys Gly Ala Arg Ile Asp Phe
            100                 105                 110

AAA GAT GTG ACT TAC TTA ACA GAA GAG AAG GTA TAT GAA ATT CTT GAA        384
Lys Asp Val Thr Tyr Leu Thr Glu Glu Lys Val Tyr Glu Ile Leu Glu
        115                 120                 125

TTA TGT AGA GAA AGA GAG GAT TAT TCC CCT TTA ATC CGT GTT ATT GGA        432
Leu Cys Arg Glu Arg Glu Asp Tyr Ser Pro Leu Ile Arg Val Ile Gly
    130                 135                 140

AGA GTT TTT TCT AGT GCT GAG GCA TTG GTA CAG AGC TTC CGG AAA GTT        480
Arg Val Phe Ser Ser Ala Glu Ala Leu Val Gln Ser Phe Arg Lys Val
145                 150                 155                 160

AAA CAA CAC ACC AAG GAA GAA CTG AAA TCT CTT CAA GCA AAA GAT GAA        528
Lys Gln His Thr Lys Glu Glu Leu Lys Ser Leu Gln Ala Lys Asp Glu
                165                 170                 175

GAC AAA GAT GAA GAT GAA AAG GAA AAA GCT GCA TGT TCT GCT GCT GCT        576
Asp Lys Asp Glu Asp Glu Lys Glu Lys Ala Ala Cys Ser Ala Ala Ala
            180                 185                 190

ATG GAA GAA GAC TCA GAA GCA TCT TCC TCA AGG ATA GGT GAT AGC TCA        624
Met Glu Glu Asp Ser Glu Ala Ser Ser Ser Arg Ile Gly Asp Ser Ser
        195                 200                 205
```

-continued

| | |
|---|---|
| CAG GGA GAC AAC AAT TTG CAA AAA TTA GGC CCT GAT GAT GTG TCT GTG<br>Gln Gly Asp Asn Asn Leu Gln Lys Leu Gly Pro Asp Asp Val Ser Val<br>210                              215                         220 | 672 |
| GAT ATT GAT GCC ATT AGA AGG GTC TAC ACC AGA TTG CTC TCT AAT GAA<br>Asp Ile Asp Ala Ile Arg Arg Val Tyr Thr Arg Leu Leu Ser Asn Glu<br>225                           230                         235                   240 | 720 |
| AAA ATT GAA ACT GCC TTT CTC AAT GCA CTT GTA TAT TTG TCA CCT AAC<br>Lys Ile Glu Thr Ala Phe Leu Asn Ala Leu Val Tyr Leu Ser Pro Asn<br>                         245                         250                       255 | 768 |
| GTG GAA TGT GAC TTG ACG TAT CAC AAT GTA TAC TCT CGA GAT CCT AAT<br>Val Glu Cys Asp Leu Thr Tyr His Asn Val Tyr Ser Arg Asp Pro Asn<br>                     260                         265                       270 | 816 |
| TAT CTG AAT TTG TTC ATT ATC GGA ATG GAG AAT AGA AAT CTC CAC AGT<br>Tyr Leu Asn Leu Phe Ile Ile Gly Met Glu Asn Arg Asn Leu His Ser<br>         275                         280                         285 | 864 |
| CCT GAA TAT CTG GAA ATG GCT TTG CCA TTA TTT TGC AAA GCG ATG AGC<br>Pro Glu Tyr Leu Glu Met Ala Leu Pro Leu Phe Cys Lys Ala Met Ser<br>290                              295                         300 | 912 |
| AAG CTA CCC CTT GCA GCC CAA GGA AAA CTG ATC AGA CTG TGG TCT AAA<br>Lys Leu Pro Leu Ala Ala Gln Gly Lys Leu Ile Arg Leu Trp Ser Lys<br>305                           310                         315                   320 | 960 |
| TAC AAT GCA GAC CAG ATT CGG AGA ATG ATG GAG ACA TTT CAG CAA CTT<br>Tyr Asn Ala Asp Gln Ile Arg Arg Met Met Glu Thr Phe Gln Gln Leu<br>                         325                         330                       335 | 1008 |
| ATT ACT TAT AAA GTC ATA AGC AAT GAA TTT AAC AGT CGA AAT CTA GTG<br>Ile Thr Tyr Lys Val Ile Ser Asn Glu Phe Asn Ser Arg Asn Leu Val<br>                   340                         345                       350 | 1056 |
| AAT GAA TTT AAC AGT CGA AAT CTA GTG AAT GAT GAT GAT GCC ATT GTT<br>Asn Glu Phe Asn Ser Arg Asn Leu Val Asn Asp Asp Asp Ala Ile Val<br>               355                         360                       365 | 1104 |
| GCT GCT TCG AAG TGC TTG AAA ATG GTT TAC TAT GCA AAT GTA GTG GGA<br>Ala Ala Ser Lys Cys Leu Lys Met Val Tyr Tyr Ala Asn Val Val Gly<br>370                              375                         380 | 1152 |
| GGG GAA GTG GAC ACA AAT CAC AAT GAA GAA GAT GAT GAA GAG CCC ATC<br>Gly Glu Val Asp Thr Asn His Asn Glu Glu Asp Asp Glu Glu Pro Ile<br>385                              390                         395                   400 | 1200 |
| CCT GAG TCC AGC GAG CTG ACA CTT CAG GAA CTT TTG GGA GAA GAA AGA<br>Pro Glu Ser Ser Glu Leu Thr Leu Gln Glu Leu Leu Gly Glu Glu Arg<br>                         405                         410                       415 | 1248 |
| AGA AAC AAG AAA GGT CTT CGA GTG GAC CCC CTG GAA ACT GAA CTT GGT<br>Arg Asn Lys Lys Gly Leu Arg Val Asp Pro Leu Glu Thr Glu Leu Gly<br>                   420                         425                       430 | 1296 |
| GTT AAA ACC CTG GAT TGT CGA AAA CCA CTT ATC CCT TTT GAA GAG TTT<br>Val Lys Thr Leu Asp Cys Arg Lys Pro Leu Ile Pro Phe Glu Glu Phe<br>               435                         440                       445 | 1344 |
| ATT AAT GAA CCA CTG AAT GAG GTT CTA GAA ATG GAT AAA GAT TAT ACT<br>Ile Asn Glu Pro Leu Asn Glu Val Leu Glu Met Asp Lys Asp Tyr Thr<br>450                              455                         460 | 1392 |
| TTT TTC AAA GTA GAA ACA GAG AAC AAA TTC TCT TTT ATG ACA TGT CCC<br>Phe Phe Lys Val Glu Thr Glu Asn Lys Phe Ser Phe Met Thr Cys Pro<br>465                              470                         475                   480 | 1440 |
| TTT ATA TTG AAT GCT GTC ACA AAG AAT TTG GGA TTA TAT TAT GAC AAT<br>Phe Ile Leu Asn Ala Val Thr Lys Asn Leu Gly Leu Tyr Tyr Asp Asn<br>                         485                         490                       495 | 1488 |
| AGA ATT CGC ATG TAC AGT GAA CGA AGA ATC ACT GTT CTC TAC AGC TTA<br>Arg Ile Arg Met Tyr Ser Glu Arg Arg Ile Thr Val Leu Tyr Ser Leu<br>                   500                         505                       510 | 1536 |
| GTT CAA GGA CAG CAG TTG AAT CCA TAT TTG AGA CTC AAA GTT AGA CGT<br>Val Gln Gly Gln Gln Leu Asn Pro Tyr Leu Arg Leu Lys Val Arg Arg<br>               515                         520                       525 | 1584 |

```
GAC CAT ATC ATA GAT GAT GCA CTT GTC CGG CTA GAG ATG ATC GCT ATG    1632
Asp His Ile Ile Asp Asp Ala Leu Val Arg Leu Glu Met Ile Ala Met
        530                 535                 540

GAA AAT CCT GCA GAC TTG AAG AAG CAG TTG TAT GTG GAA TTT GAA GGA    1680
Glu Asn Pro Ala Asp Leu Lys Lys Gln Leu Tyr Val Glu Phe Glu Gly
545                 550                 555                 560

GAA CAA GGA GTT GAT GAG GGA GGT GTT TCC AAA GAA TTT TTT CAG CTG    1728
Glu Gln Gly Val Asp Glu Gly Gly Val Ser Lys Glu Phe Phe Gln Leu
                565                 570                 575

GTT GTG GAG GAA ATC TTC AAT CCA GAT ATT GGT ATG TTC ACA TAC GAT    1776
Val Val Glu Glu Ile Phe Asn Pro Asp Ile Gly Met Phe Thr Tyr Asp
            580                 585                 590

GAA TCT ACA AAA TTG TTT TGG TTT AAT CCA TCT TCT TTT GAA ACA GAG    1824
Glu Ser Thr Lys Leu Phe Trp Phe Asn Pro Ser Ser Phe Glu Thr Glu
        595                 600                 605

GGT CAG TTT ACT CTG ATT GGC ATA GTA CTG GGT CTG GCT ATT TAC AAT    1872
Gly Gln Phe Thr Leu Ile Gly Ile Val Leu Gly Leu Ala Ile Tyr Asn
    610                 615                 620

AAC TGT ATA CTG GAT GTA CAT TTT CCC ATG GTT GTC TAC AGG AAG CTA    1920
Asn Cys Ile Leu Asp Val His Phe Pro Met Val Val Tyr Arg Lys Leu
625                 630                 635                 640

ATG GGG AAA AAA GGA CTT TTC GTC GAC TTG GGA GAC TCT CAC CCA GTT    1968
Met Gly Lys Lys Gly Leu Phe Val Asp Leu Gly Asp Ser His Pro Val
                645                 650                 655

CTA TAT CAG AGT TTA AAA GAT TTA TTG GAG TAT GTT GGG AAT GTG GAA    2016
Leu Tyr Gln Ser Leu Lys Asp Leu Leu Glu Tyr Val Gly Asn Val Glu
            660                 665                 670

GAT GAC ATG ATG ATC ACT TTC CAG ATA TCA CAG ACA AAT CTT TTT GGT    2064
Asp Asp Met Met Ile Thr Phe Gln Ile Ser Gln Thr Asn Leu Phe Gly
        675                 680                 685

AAC CCA ATG ATG TAT GAT CTA AAG GAA AAT GGT GAT AAA ATT CCA ATT    2112
Asn Pro Met Met Tyr Asp Leu Lys Glu Asn Gly Asp Lys Ile Pro Ile
    690                 695                 700

ACA AAT GAA AAC AGG AAG GAA TTT GTC AAT CTT TAT TCT GAC TAC ATT    2160
Thr Asn Glu Asn Arg Lys Glu Phe Val Asn Leu Tyr Ser Asp Tyr Ile
705                 710                 715                 720

CTC AAT AAA TCA GTA GAA AAA CAG TTC AAG GCT TTT CGG AGA GGT TTT    2208
Leu Asn Lys Ser Val Glu Lys Gln Phe Lys Ala Phe Arg Arg Gly Phe
                725                 730                 735

CAT ATG GTG ACC AAT GAA TCT CCC TTA AAG TAC TTA TTC AGA CCA GAA    2256
His Met Val Thr Asn Glu Ser Pro Leu Lys Tyr Leu Phe Arg Pro Glu
            740                 745                 750

GAA ATT GAA TTG CTT ATA TGT GGA AGC CGC AAT CTA GAT TTC CAA GCA    2304
Glu Ile Glu Leu Leu Ile Cys Gly Ser Arg Asn Leu Asp Phe Gln Ala
        755                 760                 765

CTA GAA GAA ACT ACA GAA TAT GAC GGT GGC TAT ACC AGG GAC TCT GTT    2352
Leu Glu Glu Thr Thr Glu Tyr Asp Gly Gly Tyr Thr Arg Asp Ser Val
    770                 775                 780

CTG ATT AGG GAG TTC TGG GAA ATC GTT CAT TCA TTT ACA GAT GAA CAG    2400
Leu Ile Arg Glu Phe Trp Glu Ile Val His Ser Phe Thr Asp Glu Gln
785                 790                 795                 800

AAA AGA CTC TTC TTG CAG TTT ACA ACG GGC ACA GAC AGA GCA CCT GTG    2448
Lys Arg Leu Phe Leu Gln Phe Thr Thr Gly Thr Asp Arg Ala Pro Val
                805                 810                 815

GGA GGA CTA GGA AAA TTA AAG ATG ATT ATA GCC AAA AAT GGC CCA GAC    2496
Gly Gly Leu Gly Lys Leu Lys Met Ile Ile Ala Lys Asn Gly Pro Asp
            820                 825                 830

ACA GAA AGG TTA CCT ACA TCT CAT ACT TGC TTT AAT GTG CTT TTA CTT    2544
Thr Glu Arg Leu Pro Thr Ser His Thr Cys Phe Asn Val Leu Leu Leu
```

```
                835                 840                 845
CCG GAA TAC TCA AGC AAA GAA AAA CTT AAA GAG AGA TTG TTG AAG GCC         2592
Pro Glu Tyr Ser Ser Lys Glu Lys Leu Lys Glu Arg Leu Leu Lys Ala
    850                 855                 860

ATC ACG TAT GCC AAA GGA TTT GGC ATG CTG TA                              2624
Ile Thr Tyr Ala Lys Gly Phe Gly Met Leu
865                 870
```

(2) INFORMATION FOR SEQ ID NO:21:

(i) SEQUENCE CHARACTERISTICS:
        (A) LENGTH: 874 amino acids
        (B) TYPE: amino acid
        (D) TOPOLOGY: linear (ii) MOLECULE TYPE: protein (xi) SEQUENCE DESCRIPTION: SEQ ID NO:21:

```
Ser Gly Glu Pro Gln Ser Asp Asp Ile Glu Ala Ser Arg Met Lys Arg
 1               5                  10                  15

Ala Ala Ala Lys His Leu Ile Glu Arg Tyr Tyr His Gln Leu Thr Glu
                20                  25                  30

Gly Cys Gly Asn Glu Ala Cys Thr Asn Glu Phe Cys Ala Ser Cys Pro
            35                  40                  45

Thr Phe Leu Arg Met Asp Asn Asn Ala Ala Ala Ile Lys Ala Leu Glu
        50                  55                  60

Leu Tyr Lys Ile Asn Ala Lys Leu Cys Asp Pro His Pro Ser Lys Lys
65                  70                  75                  80

Gly Ala Ser Ser Ala Tyr Leu Glu Asn Ser Lys Gly Ala Pro Asn Asn
                85                  90                  95

Ser Cys Ser Glu Ile Lys Met Asn Lys Lys Gly Ala Arg Ile Asp Phe
            100                 105                 110

Lys Asp Val Thr Tyr Leu Thr Glu Glu Lys Val Tyr Glu Ile Leu Glu
        115                 120                 125

Leu Cys Arg Glu Arg Glu Asp Tyr Ser Pro Leu Ile Arg Val Ile Gly
    130                 135                 140

Arg Val Phe Ser Ser Ala Glu Ala Leu Val Gln Ser Phe Arg Lys Val
145                 150                 155                 160

Lys Gln His Thr Lys Glu Glu Leu Lys Ser Leu Gln Ala Lys Asp Glu
                165                 170                 175

Asp Lys Asp Glu Asp Glu Lys Glu Lys Ala Ala Cys Ser Ala Ala Ala
            180                 185                 190

Met Glu Glu Asp Ser Glu Ala Ser Ser Ser Arg Ile Gly Asp Ser Ser
        195                 200                 205

Gln Gly Asp Asn Asn Leu Gln Lys Leu Gly Pro Asp Asp Val Ser Val
    210                 215                 220

Asp Ile Asp Ala Ile Arg Arg Val Tyr Thr Arg Leu Leu Ser Asn Glu
225                 230                 235                 240

Lys Ile Glu Thr Ala Phe Leu Asn Ala Leu Val Tyr Leu Ser Pro Asn
                245                 250                 255

Val Glu Cys Asp Leu Thr Tyr His Asn Val Tyr Ser Arg Asp Pro Asn
            260                 265                 270

Tyr Leu Asn Leu Phe Ile Ile Gly Met Glu Asn Arg Asn Leu His Ser
        275                 280                 285

Pro Glu Tyr Leu Glu Met Ala Leu Pro Leu Phe Cys Lys Ala Met Ser
    290                 295                 300
```

```
Lys Leu Pro Leu Ala Ala Gln Gly Lys Leu Ile Arg Leu Trp Ser Lys
305                 310                 315                 320

Tyr Asn Ala Asp Gln Ile Arg Arg Met Met Glu Thr Phe Gln Gln Leu
            325                 330                 335

Ile Thr Tyr Lys Val Ile Ser Asn Glu Phe Asn Ser Arg Asn Leu Val
                340                 345                 350

Asn Glu Phe Asn Ser Arg Asn Leu Val Asn Asp Asp Ala Ile Val
            355                 360                 365

Ala Ala Ser Lys Cys Leu Lys Met Val Tyr Ala Asn Val Val Gly
    370                 375                 380

Gly Glu Val Asp Thr Asn His Asn Glu Glu Asp Glu Glu Pro Ile
385                 390                 395                 400

Pro Glu Ser Ser Glu Leu Thr Leu Gln Glu Leu Leu Gly Glu Glu Arg
                405                 410                 415

Arg Asn Lys Lys Gly Leu Arg Val Asp Pro Leu Glu Thr Glu Leu Gly
            420                 425                 430

Val Lys Thr Leu Asp Cys Arg Lys Pro Leu Ile Pro Phe Glu Glu Phe
    435                 440                 445

Ile Asn Glu Pro Leu Asn Glu Val Leu Glu Met Asp Lys Asp Tyr Thr
450                 455                 460

Phe Phe Lys Val Glu Thr Glu Asn Lys Phe Ser Phe Met Thr Cys Pro
465                 470                 475                 480

Phe Ile Leu Asn Ala Val Thr Lys Asn Leu Gly Leu Tyr Tyr Asp Asn
            485                 490                 495

Arg Ile Arg Met Tyr Ser Glu Arg Arg Ile Thr Val Leu Tyr Ser Leu
                500                 505                 510

Val Gln Gly Gln Gln Leu Asn Pro Tyr Leu Arg Leu Lys Val Arg Arg
    515                 520                 525

Asp His Ile Ile Asp Asp Ala Leu Val Arg Leu Glu Met Ile Ala Met
        530                 535                 540

Glu Asn Pro Ala Asp Leu Lys Lys Gln Leu Tyr Val Glu Phe Glu Gly
545                 550                 555                 560

Glu Gln Gly Val Asp Glu Gly Gly Val Ser Lys Glu Phe Phe Gln Leu
            565                 570                 575

Val Val Glu Glu Ile Phe Asn Pro Asp Ile Gly Met Phe Thr Tyr Asp
                580                 585                 590

Glu Ser Thr Lys Leu Phe Trp Phe Asn Pro Ser Ser Phe Glu Thr Glu
    595                 600                 605

Gly Gln Phe Thr Leu Ile Gly Ile Val Leu Gly Leu Ala Ile Tyr Asn
610                 615                 620

Asn Cys Ile Leu Asp Val His Phe Pro Met Val Val Tyr Arg Lys Leu
625                 630                 635                 640

Met Gly Lys Lys Gly Leu Phe Val Asp Leu Gly Asp Ser His Pro Val
            645                 650                 655

Leu Tyr Gln Ser Leu Lys Asp Leu Leu Glu Tyr Val Gly Asn Val Glu
                660                 665                 670

Asp Asp Met Met Ile Thr Phe Gln Ile Ser Gln Thr Asn Leu Phe Gly
    675                 680                 685

Asn Pro Met Met Tyr Asp Leu Lys Glu Asn Gly Asp Lys Ile Pro Ile
690                 695                 700

Thr Asn Glu Asn Arg Lys Glu Phe Val Asn Leu Tyr Ser Asp Tyr Ile
705                 710                 715                 720

Leu Asn Lys Ser Val Glu Lys Gln Phe Lys Ala Phe Arg Arg Gly Phe
```

```
                    725                 730                 735
His Met Val Thr Asn Glu Ser Pro Leu Lys Tyr Leu Phe Arg Pro Glu
            740                 745                 750

Glu Ile Glu Leu Leu Ile Cys Gly Ser Arg Asn Leu Asp Phe Gln Ala
            755                 760                 765

Leu Glu Glu Thr Thr Glu Tyr Asp Gly Gly Tyr Thr Arg Asp Ser Val
            770                 775                 780

Leu Ile Arg Glu Phe Trp Glu Ile Val His Ser Phe Thr Asp Glu Gln
785                 790                 795                 800

Lys Arg Leu Phe Leu Gln Phe Thr Thr Gly Thr Asp Arg Ala Pro Val
                805                 810                 815

Gly Gly Leu Gly Lys Leu Lys Met Ile Ile Ala Lys Asn Gly Pro Asp
                820                 825                 830

Thr Glu Arg Leu Pro Thr Ser His Thr Cys Phe Asn Val Leu Leu Leu
                835                 840                 845

Pro Glu Tyr Ser Ser Lys Glu Lys Leu Lys Glu Arg Leu Leu Lys Ala
            850                 855                 860

Ile Thr Tyr Ala Lys Gly Phe Gly Met Leu
865                 870
```

(2) INFORMATION FOR SEQ ID NO:22:

(i) SEQUENCE CHARACTERISTICS:
        (A) LENGTH: 1181 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1179

(xi) SEQUENCE DESCRIPTION: SEQ ID NO:22:

```
ATG GAG GAG CCG CAG TCA GAT CCT AGC GTC GAG CCC CCT CTG AGT CAG      48
Met Glu Glu Pro Gln Ser Asp Pro Ser Val Glu Pro Pro Leu Ser Gln
 1               5                  10                  15

GAA ACA TTT TCA GAC CTA TGG AAA CTA CTT CCT GAA AAC AAC GTT CTG      96
Glu Thr Phe Ser Asp Leu Trp Lys Leu Leu Pro Glu Asn Asn Val Leu
                20                  25                  30

TCC CCC TTG CCG TCC CAA GCA ATG GAT GAT TTG ATG CTG TCC CCG GAC     144
Ser Pro Leu Pro Ser Gln Ala Met Asp Asp Leu Met Leu Ser Pro Asp
            35                  40                  45

GAT ATT GAA CAA TGG TTC ACT GAA GAC CCA GGT CCA GAT GAA GCT CCC     192
Asp Ile Glu Gln Trp Phe Thr Glu Asp Pro Gly Pro Asp Glu Ala Pro
        50                  55                  60

AGA ATG CCA GAG GCT GCT CCC CCC GTG GCC CCT GCA CCA GCA GCT CCT     240
Arg Met Pro Glu Ala Ala Pro Pro Val Ala Pro Ala Pro Ala Ala Pro
 65                  70                  75                  80

ACA CCG GCG GCC CCT GCA CCA GCC CCC TCC TGG CCC CTG TCA TCT TCT     288
Thr Pro Ala Ala Pro Ala Pro Ala Pro Ser Trp Pro Leu Ser Ser Ser
                    85                  90                  95

GTC CCT TCC CAG AAA ACC TAC CAG GGC AGC TAC GGT TTC CGT CTG GGC     336
Val Pro Ser Gln Lys Thr Tyr Gln Gly Ser Tyr Gly Phe Arg Leu Gly
                100                 105                 110

TTC TTG CAT TCT GGG ACA GCC AAG TCT GTG ACT TGC ACG TAC TCC CCT     384
Phe Leu His Ser Gly Thr Ala Lys Ser Val Thr Cys Thr Tyr Ser Pro
            115                 120                 125

GCC CTC AAC AAG ATG TTT TGC CAA CTG GCC AAG ACC TGC CCT GTG CAG     432
```

```
Ala Leu Asn Lys Met Phe Cys Gln Leu Ala Lys Thr Cys Pro Val Gln
        130                 135                 140

CTG TGG GTT GAT TCC ACA CCC CCG CCC GGC ACC CGC GTC CGC GCC ATG       480
Leu Trp Val Asp Ser Thr Pro Pro Pro Gly Thr Arg Val Arg Ala Met
145                 150                 155                 160

GCC ATC TAC AAG CAG TCA CAG CAC ATG ACG GAG GTT GTG AGG CGC TGC       528
Ala Ile Tyr Lys Gln Ser Gln His Met Thr Glu Val Val Arg Arg Cys
                165                 170                 175

CCC CAC CAT GAG CGC TGC TCA GAT AGC GAT GGT CTG GCC CCT CCT CAG       576
Pro His His Glu Arg Cys Ser Asp Ser Asp Gly Leu Ala Pro Pro Gln
            180                 185                 190

CAT CTT ATC CGA GTG GAA GGA AAT TTG CGT GTG GAG TAT TTG GAT GAC       624
His Leu Ile Arg Val Glu Gly Asn Leu Arg Val Glu Tyr Leu Asp Asp
        195                 200                 205

AGA AAC ACT TTT CGA CAT AGT GTG GTG GTG CCC TAT GAG CCG CCT GAG       672
Arg Asn Thr Phe Arg His Ser Val Val Val Pro Tyr Glu Pro Pro Glu
210                 215                 220

GTT GGC TCT GAC TGT ACC ACC ATC CAC TAC AAC TAC ATG TGT AAC AGT       720
Val Gly Ser Asp Cys Thr Thr Ile His Tyr Asn Tyr Met Cys Asn Ser
225                 230                 235                 240

TCC TGC ATG GGC GGC ATG AAC CGG AGG CCC ATC CTC ACC ATC ATC ACA       768
Ser Cys Met Gly Gly Met Asn Arg Arg Pro Ile Leu Thr Ile Ile Thr
                245                 250                 255

CTG GAA GAC TCC AGT GGT AAT CTA CTG GGA CGG AAC AGC TTT GAG GTG       816
Leu Glu Asp Ser Ser Gly Asn Leu Leu Gly Arg Asn Ser Phe Glu Val
            260                 265                 270

CGT GTT TGT GCC TGT CCT GGG AGA GAC CGG CGC ACA GAG GAA GAG AAT       864
Arg Val Cys Ala Cys Pro Gly Arg Asp Arg Arg Thr Glu Glu Glu Asn
        275                 280                 285

CTC CGC AAG AAA GGG GAG CCT CAC CAC GAG CTG CCC CCA GGG AGC ACT       912
Leu Arg Lys Lys Gly Glu Pro His His Glu Leu Pro Pro Gly Ser Thr
290                 295                 300

AAG CGA GCA CTG CCC AAC AAC ACC AGC TCC TCT CCC CAG CCA AAG AAG       960
Lys Arg Ala Leu Pro Asn Asn Thr Ser Ser Ser Pro Gln Pro Lys Lys
305                 310                 315                 320

AAA CCA CTG GAT GGA GAA TAT TTC ACC CTT CAG ATC CGT GGG CGT GAG      1008
Lys Pro Leu Asp Gly Glu Tyr Phe Thr Leu Gln Ile Arg Gly Arg Glu
                325                 330                 335

CGC TTC GAG ATG TTC CGA GAG CTG AAT GAG GCC TTG GAA CTC AAG GAT      1056
Arg Phe Glu Met Phe Arg Glu Leu Asn Glu Ala Leu Glu Leu Lys Asp
            340                 345                 350

GCC CAG GCT GGG AAG GAG CCA GGG GGG AGC AGG GCT CAC TCC AGC CAC      1104
Ala Gln Ala Gly Lys Glu Pro Gly Gly Ser Arg Ala His Ser Ser His
        355                 360                 365

CTG AAG TCC AAA AAG GGT CAG TCT ACC TCC CGC CAT AAA AAA CTC ATG      1152
Leu Lys Ser Lys Lys Gly Gln Ser Thr Ser Arg His Lys Lys Leu Met
370                 375                 380

TTC AAG ACA GAA GGG CCT GAC TCA GAC TG                               1181
Phe Lys Thr Glu Gly Pro Asp Ser Asp
385                 390
```

(2) INFORMATION FOR SEQ ID NO:23:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:23:

-continued

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
             85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
            290                 295                 300

Lys Arg Ala Leu Pro Asn Asn Thr Ser Ser Pro Gln Pro Lys Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
            370                 375                 380

Phe Lys Thr Glu Gly Pro Asp Ser Asp
385                 390
```

(2) INFORMATION FOR SEQ ID NO:24:

(i) SEQUENCE CHARACTERISTICS:

(A) LENGTH: 897 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..894

(xi) SEQUENCE DESCRIPTION: SEQ ID NO:24:

```
ATT GCG GCG GCG CCA GAG CTG CTG GAG CGC TCG GGG TCC CCG GGC GGC        48
Ile Ala Ala Ala Pro Glu Leu Leu Glu Arg Ser Gly Ser Pro Gly Gly
 1               5                  10                  15

GGC GGC GGC GCA GAG GAG GAG GCA GGC GGC GGC CCC GGT GGC TCC CCC        96
Gly Gly Gly Ala Glu Glu Glu Ala Gly Gly Gly Pro Gly Gly Ser Pro
             20                  25                  30

CCG GAC GGT GCG CGG CCC GGC CCG TCT CGC GAA CTC GCG GTG GTC GCG       144
Pro Asp Gly Ala Arg Pro Gly Pro Ser Arg Glu Leu Ala Val Val Ala
         35                  40                  45

CGG CCC CGC GCT GCT CCG ACC CCG GGC CCC TCC GCC GCC GCC ATG GCT       192
Arg Pro Arg Ala Ala Pro Thr Pro Gly Pro Ser Ala Ala Ala Met Ala
 50                  55                  60

CGG CCG CTA GTG CCC AGC TCG CAG AAG GCG CTG CTG CTG GAG CTC AAG       240
Arg Pro Leu Val Pro Ser Ser Gln Lys Ala Leu Leu Leu Glu Leu Lys
 65                  70                  75                  80

GGG CTG CAG GAA GAG CCG GTC GAG GGA TTC CGC GTG ACA CTG GTG GAC       288
Gly Leu Gln Glu Glu Pro Val Glu Gly Phe Arg Val Thr Leu Val Asp
                 85                  90                  95

GAG GGC GAT CTA TAC AAC TGG GAG GTG GCC ATT TTC GGG CCC CCC AAC       336
Glu Gly Asp Leu Tyr Asn Trp Glu Val Ala Ile Phe Gly Pro Pro Asn
            100                 105                 110

ACC TAC TAC GAG GGC GGC TAC TTC AAG GCG CGC CTC AAG TTC CCC ATC       384
Thr Tyr Tyr Glu Gly Gly Tyr Phe Lys Ala Arg Leu Lys Phe Pro Ile
        115                 120                 125

GAC TAC CCA TAC TCT CCA CCA GCC TTT CGG TTC CTG ACC AAG ATG TGG       432
Asp Tyr Pro Tyr Ser Pro Pro Ala Phe Arg Phe Leu Thr Lys Met Trp
130                 135                 140

CAC CCT AAC ATC TAC GAG ACG GGG GAC GTG TGT ATC TCC ATC CTC CAC       480
His Pro Asn Ile Tyr Glu Thr Gly Asp Val Cys Ile Ser Ile Leu His
145                 150                 155                 160

CCG CCG GTG GAC GAC CCC CAG AGC GGG GAG CTG CCC TCA GAG AGG TGG       528
Pro Pro Val Asp Asp Pro Gln Ser Gly Glu Leu Pro Ser Glu Arg Trp
                165                 170                 175

AAC CCC ACG CAG AAC GTC AGG ACC ATT CTC CTG AGT GTG ATC TCC CTC       576
Asn Pro Thr Gln Asn Val Arg Thr Ile Leu Leu Ser Val Ile Ser Leu
            180                 185                 190

CTG AAC GAG CCC AAC ACC TTC TCG CCC GCA AAC GTG GAC GCC TCC GTG       624
Leu Asn Glu Pro Asn Thr Phe Ser Pro Ala Asn Val Asp Ala Ser Val
        195                 200                 205

ATG TAC AGG AAG TGG AAA GAG AGC AAG GGG AAG GAT CGG GAG TAC ACA       672
Met Tyr Arg Lys Trp Lys Glu Ser Lys Gly Lys Asp Arg Glu Tyr Thr
    210                 215                 220

GAC ATC ATC CGG AAG CAG GTC CTG GGG ACC AAG GTG GAC GCG GAG CGT       720
Asp Ile Ile Arg Lys Gln Val Leu Gly Thr Lys Val Asp Ala Glu Arg
225                 230                 235                 240

GAC GGC GTG AAG GTG CCC ACC ACG CTG GCC GAG TAC TGC GTG AAG ACC       768
Asp Gly Val Lys Val Pro Thr Thr Leu Ala Glu Tyr Cys Val Lys Thr
                245                 250                 255

AAG GCG CCG GCG CCC GAC GAG GGC TCA GAC CTC TTC TAC GAC GAC TAC       816
Lys Ala Pro Ala Pro Asp Glu Gly Ser Asp Leu Phe Tyr Asp Asp Tyr
```

```
                    260                 265                 270
TAC GAG GAC GGC GAG GTG GAG GAG GAG GCC GAC AGC TGC TTC GGG GAC        864
Tyr Glu Asp Gly Glu Val Glu Glu Glu Ala Asp Ser Cys Phe Gly Asp
                    275                 280                 285

GAT GAG GAT GAC TCT GGC ACG GAG GAG TCC TGA                            897
Asp Glu Asp Asp Ser Gly Thr Glu Glu Ser
                290                 295
```

(2) INFORMATION FOR SEQ ID NO:25:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO:25:

```
Ile Ala Ala Ala Pro Glu Leu Leu Glu Arg Ser Gly Ser Pro Gly Gly
 1               5                  10                  15

Gly Gly Gly Ala Glu Glu Glu Ala Gly Gly Gly Pro Gly Gly Ser Pro
                20                  25                  30

Pro Asp Gly Ala Arg Pro Gly Pro Ser Arg Glu Leu Ala Val Val Ala
                35                  40                  45

Arg Pro Arg Ala Ala Pro Thr Pro Gly Pro Ser Ala Ala Ala Met Ala
        50                  55                  60

Arg Pro Leu Val Pro Ser Ser Gln Lys Ala Leu Leu Glu Leu Lys
 65                  70                  75                  80

Gly Leu Gln Glu Glu Pro Val Glu Gly Phe Arg Val Thr Leu Val Asp
                85                  90                  95

Glu Gly Asp Leu Tyr Asn Trp Glu Val Ala Ile Phe Gly Pro Pro Asn
                100                 105                 110

Thr Tyr Tyr Glu Gly Gly Tyr Phe Lys Ala Arg Leu Lys Phe Pro Ile
                115                 120                 125

Asp Tyr Pro Tyr Ser Pro Pro Ala Phe Arg Phe Leu Thr Lys Met Trp
        130                 135                 140

His Pro Asn Ile Tyr Glu Thr Gly Asp Val Cys Ile Ser Ile Leu His
145                 150                 155                 160

Pro Pro Val Asp Asp Pro Gln Ser Gly Glu Leu Pro Ser Glu Arg Trp
                165                 170                 175

Asn Pro Thr Gln Asn Val Arg Thr Ile Leu Leu Ser Val Ile Ser Leu
                180                 185                 190

Leu Asn Glu Pro Asn Thr Phe Ser Pro Ala Asn Val Asp Ala Ser Val
                195                 200                 205

Met Tyr Arg Lys Trp Lys Glu Ser Lys Gly Lys Asp Arg Glu Tyr Thr
        210                 215                 220

Asp Ile Ile Arg Lys Gln Val Leu Gly Thr Lys Val Asp Ala Glu Arg
225                 230                 235                 240

Asp Gly Val Lys Val Pro Thr Thr Leu Ala Glu Tyr Cys Val Lys Thr
                245                 250                 255

Lys Ala Pro Ala Pro Asp Glu Gly Ser Asp Leu Phe Tyr Asp Asp Tyr
                260                 265                 270

Tyr Glu Asp Gly Glu Val Glu Glu Glu Ala Asp Ser Cys Phe Gly Asp
                275                 280                 285

Asp Glu Asp Asp Ser Gly Thr Glu Glu Ser
                290                 295
```

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CTACTAATAG GTAGAAGCGG TGG                                            23

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGTAAACCAA AGCACCGACA GGG                                            23

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

GCGCGCAAGC TTATGTCCAG CTCGCCGCTG TCCAAG                              36

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:29:

GCGCGCGGAT CCTCAGCGGA TGGTGTATCG GACATA                              36

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:30:

GCGCGCAAGC TTATGTCGAC CCCGGCCCGG AGGAGG                              36

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:31:

GCGCGCGAAT TCTTATGAAT CATTCCAGCT TTGTTC                      36

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:32:

GCGCGCAAGC TTATGGCGCG CTTTGAGGAT CCAACA                      36

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:33:

GCGCGCGAAT TCTTATACTT GTGTTTCTCT GCGTCG                      36

(2) INFORMATION FOR SEQ ID NO:34:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:34:

GCGCGCAAGC TTTCAGGACC TCAGTCTGAC GAC                           33

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:35:

GCGCGCGGAT CCTTACAGCA TGCCAAATCC TTTGGC                      36

(2) INFORMATION FOR SEQ ID NO:36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:36:

GCGCGCGAAT TCGCCATGGA GGAGCCGCAG TCAGATCCT                                39

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:37:

GCGCGCAAGC TTTCAGTCTG AGTCAGGCCC TTCTGT                                   36

(2) INFORMATION FOR SEQ ID NO:38:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Pro Val Gly Asp Asp Leu Phe His Trp Xaa
1               5                   10

(2) INFORMATION FOR SEQ ID NO:39:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Ile Thr Leu Ala Pro Ser Trp
1               5

(2) INFORMATION FOR SEQ ID NO:40:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

TCGACGGACA TGCCCGGGCA TGTCCC                                              26

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TCGCAGGGAC ATGCCCGGGC ATGTCCG                                           27

(2) INFORMATION FOR SEQ ID NO:42:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TCGACCACGT GGC                                                          13

(2) INFORMATION FOR SEQ ID NO:43:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

TCGAGCCACG TGG                                                          13

(2) INFORMATION FOR SEQ ID NO:44:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

TCGACGGGGC GGGC                                                         14

(2) INFORMATION FOR SEQ ID NO:45:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

TCGAGCCCGC CCCG                                                         14